(12) United States Patent
Rosen et al.

(10) Patent No.: US 8,740,767 B2
(45) Date of Patent: Jun. 3, 2014

(54) INTRA-VAGINAL DEVICES AND METHODS FOR TREATING FECAL INCONTINENCE

(71) Applicant: Pelvalon, Inc., Sunnyvale, CA (US)

(72) Inventors: Miles Harris Rosen, Palo Alto, CA (US); Steven Lawrence Herbowy, Palo Alto, CA (US); Jacob Samuel Brenner, Philadelphia, PA (US)

(73) Assignee: Pelvalon, Inc., Sunnyvale, CA (US)

( * ) Notice: Subject to any disclaimer, the term of this patent is extended or adjusted under 35 U.S.C. 154(b) by 0 days.

(21) Appl. No.: 13/679,528

(22) Filed: Nov. 16, 2012

(65) Prior Publication Data

US 2013/0144112 A1    Jun. 6, 2013

Related U.S. Application Data

(63) Continuation of application No. 13/625,683, filed on Sep. 24, 2012, which is a continuation-in-part of application No. 13/635,598, filed as application No. PCT/US2011/028691 on Mar. 16, 2011.

(60) Provisional application No. 61/314,335, filed on Mar. 16, 2010, provisional application No. 61/367,418, filed on Jul. 25, 2010, provisional application No. 61/538,095, filed on Sep. 22, 2011, provisional application No. 61/704,433, filed on Sep. 21, 2012.

(51) Int. Cl.
    *A61F 2/00* (2006.01)
(52) U.S. Cl.
    USPC ............................................. 600/29; 600/37

(58) Field of Classification Search
    USPC ................ 600/29–32, 37; 128/834–836, 885, 128/DIG. 25
    See application file for complete search history.

(56) References Cited

U.S. PATENT DOCUMENTS

| | | | |
|---|---|---|---|
| 186,469 A | 1/1877 | Fowler |
| 1,282,881 A | 10/1918 | Landis |
| 2,475,071 A | 7/1949 | Thomas |
| 2,638,093 A | 12/1952 | George |
| 3,554,184 A | 1/1971 | Habib |
| 3,646,929 A | 3/1972 | Bonnar |
| 3,675,656 A | 7/1972 | Hakim |
| 3,705,575 A | 12/1972 | Edwards |
| 3,709,215 A | 1/1973 | Richmond |
| 3,797,478 A | 3/1974 | Walsh et al. |
| 3,831,583 A | 8/1974 | Edmunds, Jr. et al. |

(Continued)

FOREIGN PATENT DOCUMENTS

| | | |
|---|---|---|
| DE | 2438691 A1 | 8/1974 |
| EP | 0068318 A1 | 1/1983 |

(Continued)

OTHER PUBLICATIONS

Sokol, A, Shveiky, D. "Clinical Anatomy of the Vulva, Vagina, Lower Pelvis, and Perineum." Global Library of Women's Medicine, (ISSN: 1756-2228) 2008; DOI 10.3843/GLOWM.10000. Web. Dec. 23, 2013.*

(Continued)

*Primary Examiner* — Charles A Marmor, II
*Assistant Examiner* — Carrie R Dorna
(74) *Attorney, Agent, or Firm* — Fish & Richardson P.C.

(57) ABSTRACT

Devices and methods for intra-vaginal bowel control.

16 Claims, 70 Drawing Sheets

(56) References Cited

U.S. PATENT DOCUMENTS

| | | |
|---|---|---|
| 3,841,304 A | 10/1974 | Jones |
| 3,866,611 A | 2/1975 | Baumrucker |
| 3,882,852 A | 5/1975 | Sinnreich |
| 3,903,894 A | 9/1975 | Rosen et al. |
| 4,019,499 A | 4/1977 | Fitzgerald |
| 4,031,886 A | 6/1977 | Morhenn |
| 4,428,365 A | 1/1984 | Hakky |
| 4,587,954 A | 5/1986 | Haber |
| 4,669,478 A | 6/1987 | Robertson |
| 4,686,985 A | 8/1987 | Lottick |
| 4,786,276 A | 11/1988 | Haber |
| 4,823,814 A | 4/1989 | Drogendijk et al. |
| 4,846,818 A | 7/1989 | Keldahl et al. |
| 4,854,990 A | 8/1989 | David |
| 4,946,449 A | 8/1990 | Davis, Jr. |
| 4,981,470 A | 1/1991 | Bombeck, IV |
| 5,007,894 A | 4/1991 | Enhorning |
| 5,041,077 A | 8/1991 | Kulick |
| 5,147,301 A | 9/1992 | Ruvio |
| 5,224,494 A | 7/1993 | Enhorning |
| 5,306,226 A | 4/1994 | Salama |
| 5,370,690 A | 12/1994 | Barrett |
| 5,474,518 A | 12/1995 | Farrer Velazquez |
| 5,520,606 A | 5/1996 | Schoolman et al. |
| 5,545,176 A | 8/1996 | Murtfeldt |
| 5,593,443 A | 1/1997 | Carter et al. |
| 5,603,685 A | 2/1997 | Tutrone, Jr. |
| 5,611,768 A * | 3/1997 | Tutrone, Jr. ............ 600/29 |
| 5,702,421 A | 12/1997 | Schneidt |
| 5,733,230 A | 3/1998 | Sawchuck et al. |
| 5,884,629 A | 3/1999 | O'Brien |
| 6,013,023 A | 1/2000 | Klingenstein |
| 6,030,338 A | 2/2000 | Benderev |
| 6,048,306 A | 4/2000 | Spielberg |
| 6,090,038 A | 7/2000 | Zunker et al. |
| 6,090,098 A | 7/2000 | Zunker et al. |
| 6,096,057 A | 8/2000 | Klingenstein |
| 6,110,099 A | 8/2000 | Benderev |
| 6,135,945 A | 10/2000 | Sultan |
| 6,142,928 A | 11/2000 | Zunker et al. |
| 6,216,698 B1 | 4/2001 | Regula |
| 6,319,191 B1 | 11/2001 | Sayet et al. |
| 6,428,467 B1 | 8/2002 | Benderev |
| 6,470,890 B1 | 10/2002 | Diokno et al. |
| 6,482,145 B1 | 11/2002 | Forsell |
| 6,503,190 B1 | 1/2003 | Ulmsten et al. |
| 6,558,370 B2 | 5/2003 | Moser |
| 6,569,078 B2 | 5/2003 | Ishikawa et al. |
| 6,645,137 B2 | 11/2003 | Ulmsten et al. |
| 6,676,594 B1 | 1/2004 | Zunker et al. |
| 6,682,473 B1 | 1/2004 | Matsuura et al. |
| 6,723,040 B2 | 4/2004 | Brady |
| 6,752,754 B1 | 6/2004 | Feng et al. |
| 6,770,025 B2 | 8/2004 | Zunker |
| 6,786,861 B1 | 9/2004 | Pretorius |
| 6,808,485 B2 | 10/2004 | Zunker |
| 6,843,766 B1 | 1/2005 | Nemir et al. |
| 6,913,573 B1 | 7/2005 | Viscomi et al. |
| 6,915,165 B2 | 7/2005 | Forsell |
| 6,939,289 B2 | 9/2005 | Zunker et al. |
| 6,976,950 B2 | 12/2005 | Connors et al. |
| 7,074,178 B2 | 7/2006 | Connors et al. |
| 7,083,569 B2 | 8/2006 | Boulanger et al. |
| 7,144,391 B1 | 12/2006 | Kreutz et al. |
| 7,235,044 B2 | 6/2007 | Forsell |
| 7,258,661 B2 | 8/2007 | Davies et al. |
| 7,306,586 B2 | 12/2007 | Beaufore et al. |
| 7,311,661 B2 | 12/2007 | Heinrich |
| 7,360,544 B2 | 4/2008 | Levien |
| 7,445,598 B2 | 11/2008 | Orban, III |
| 7,540,876 B2 | 6/2009 | Connors et al. |
| 7,553,273 B2 | 6/2009 | Ferguson et al. |
| 7,628,155 B2 | 12/2009 | Carey |
| 7,628,156 B2 | 12/2009 | Astani et al. |
| 7,658,196 B2 | 2/2010 | Ferreri et al. |
| 7,673,631 B2 | 3/2010 | Astani et al. |
| 7,691,051 B2 | 4/2010 | Connors et al. |
| 7,695,427 B2 | 4/2010 | Kugler et al. |
| 7,717,892 B2 | 5/2010 | Bartning et al. |
| 7,722,583 B2 | 5/2010 | Kim et al. |
| 7,771,344 B2 | 8/2010 | Ziv |
| 7,771,346 B2 | 8/2010 | Burton et al. |
| 7,775,215 B2 | 8/2010 | Hassler, Jr. et al. |
| 7,775,966 B2 | 8/2010 | Dlugos et al. |
| 7,794,385 B2 | 9/2010 | Rosenblatt |
| 7,819,821 B2 | 10/2010 | Forte et al. |
| 7,828,713 B2 | 11/2010 | Ziv et al. |
| 7,828,714 B2 | 11/2010 | Feng et al. |
| 7,828,715 B2 | 11/2010 | Haverfield |
| 7,828,716 B2 | 11/2010 | Burton et al. |
| 7,844,342 B2 | 11/2010 | Dlugos, Jr. et al. |
| 7,892,163 B2 | 2/2011 | Bartning et al. |
| 7,927,270 B2 | 4/2011 | Dlugos et al. |
| 7,927,320 B2 | 4/2011 | Goldwasser et al. |
| 2006/0025798 A1 | 2/2006 | Cook et al. |
| 2006/0211911 A1 | 9/2006 | Jao et al. |
| 2008/0033231 A1* | 2/2008 | Bartning et al. ............ 600/29 |
| 2009/0111671 A1 | 4/2009 | Campbell et al. |
| 2009/0192346 A1 | 7/2009 | Rosenblatt |
| 2009/0216071 A1 | 8/2009 | Zipper |
| 2011/0015474 A1 | 1/2011 | Forsell |
| 2013/0012764 A1 | 1/2013 | Herbowy et al. |

FOREIGN PATENT DOCUMENTS

| | | |
|---|---|---|
| EP | 1518514 A2 | 3/2005 |
| EP | 1587464 B1 | 8/2007 |
| EP | 1587465 B1 | 11/2007 |
| EP | 1609440 B1 | 7/2008 |
| EP | 1734895 B | 7/2008 |
| EP | 1734892 B1 | 3/2011 |
| EP | 1990023 B1 | 9/2012 |
| FR | 2843700 A1 | 2/2004 |
| GB | 2352181 A | 1/2001 |
| WO | WO93/16659 A1 | 9/1993 |
| WO | WO96/01084 A1 | 1/1996 |
| WO | WO01/45487 A2 | 6/2001 |
| WO | WO02/053235 A2 | 7/2002 |
| WO | WO02/098323 A1 | 12/2002 |
| WO | WO2005/082276 A1 | 9/2005 |
| WO | WO2009/046996 A2 | 4/2009 |
| WO | WO2009/046997 A2 | 4/2009 |
| WO | WO2009/060437 A2 | 5/2009 |
| WO | WO2011/008167 A1 | 1/2011 |

OTHER PUBLICATIONS

Viera et al.; Practical use of the pessary; Am Fam Physician; 61(9); pp. 2719-2726; May 1, 2000 (downloaded Mar. 8, 2013 from: http://www.aafp.org/afp/2000/0501/p2719.html?printable=afp).

Rosen et al.; U.S. Appl. No. 13/679,484 entitled "Intra-Vaginal Devices and Methods for Treating Fecal Incontinence," filed Nov. 16, 2012.

Rosen et al.; U.S. Appl. No. 13/625,683 entitled "Intra-Vaginal Devices and Methods for Treating Fecal Incontinence," filed Sep. 24, 2012.

* cited by examiner

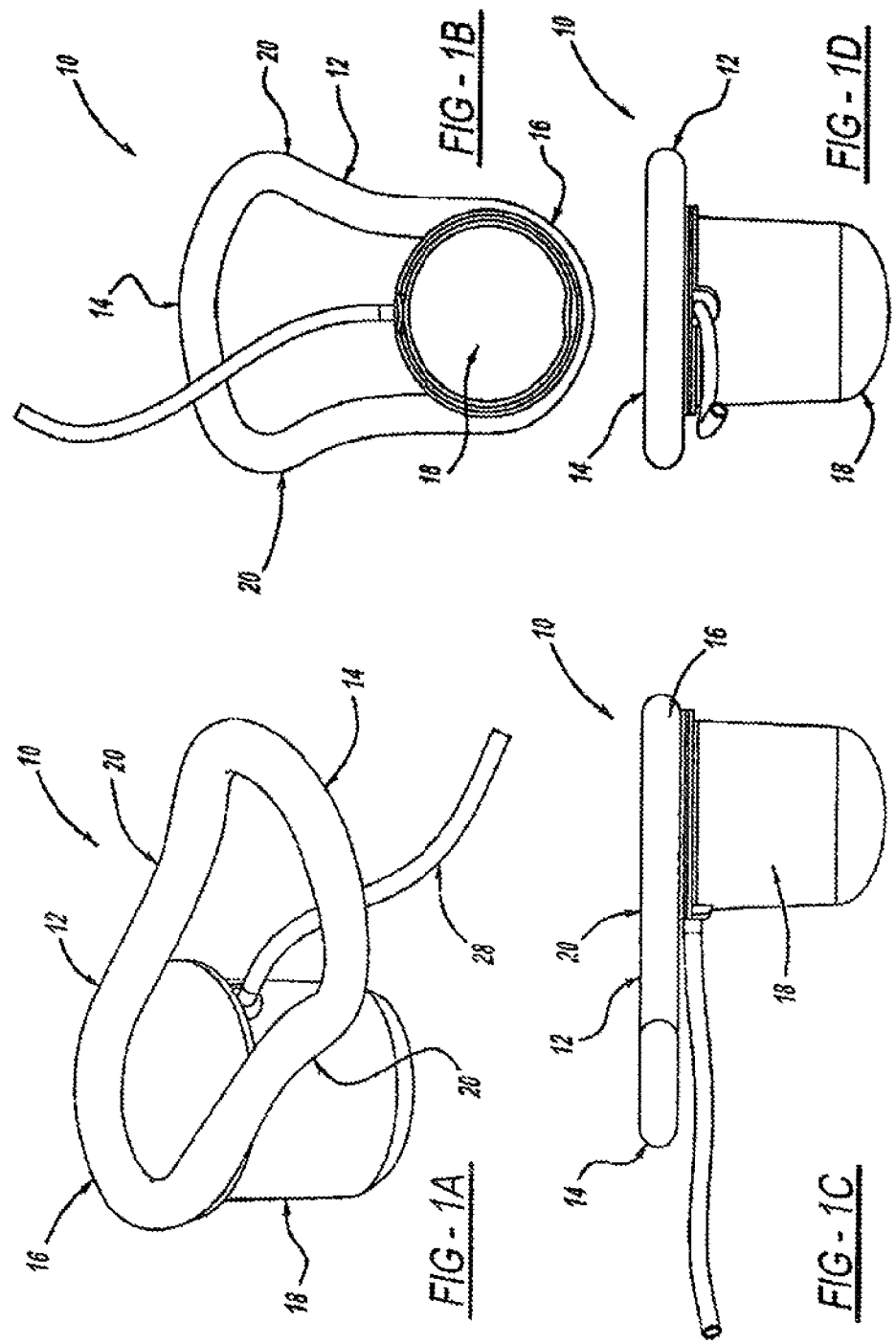

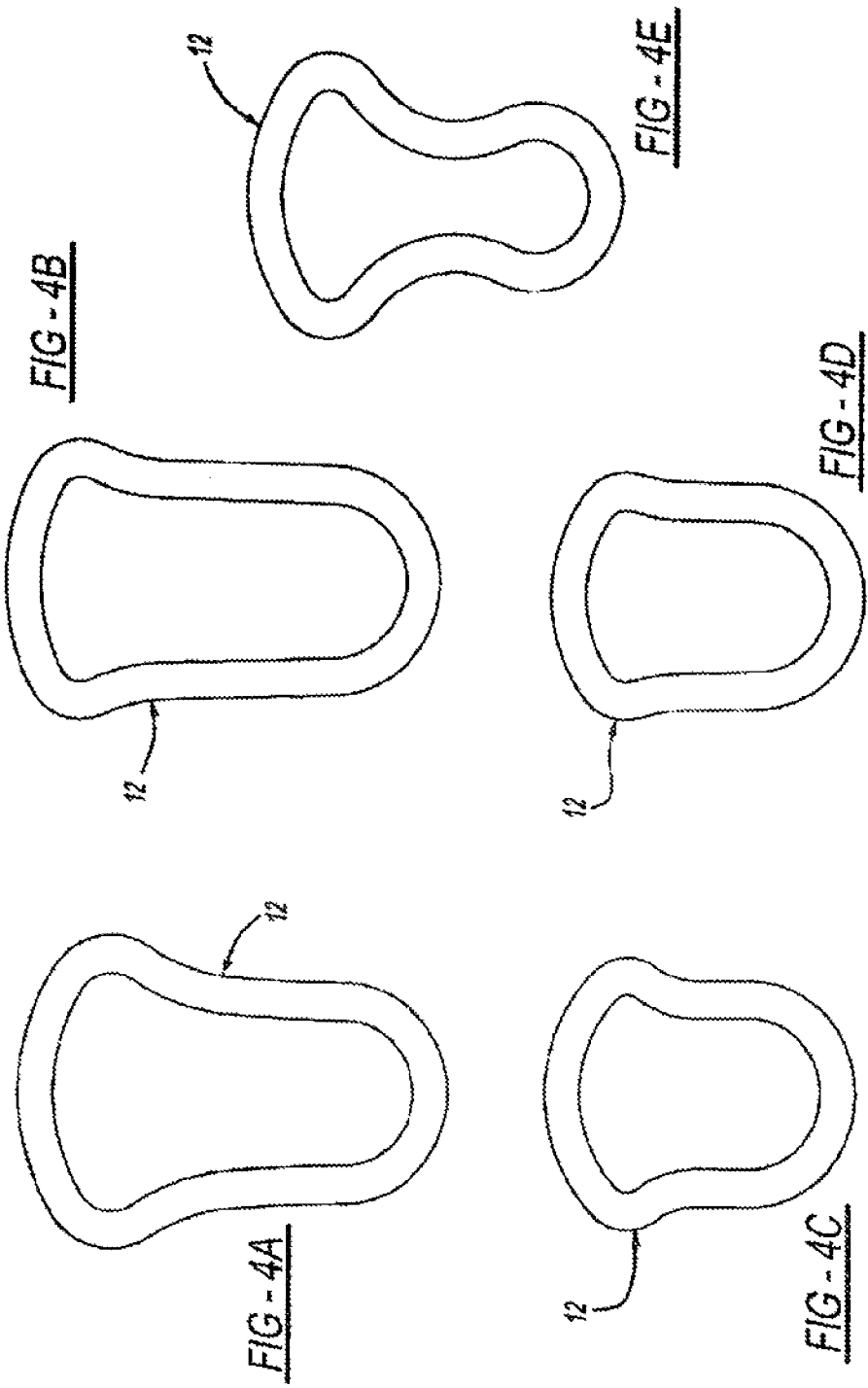

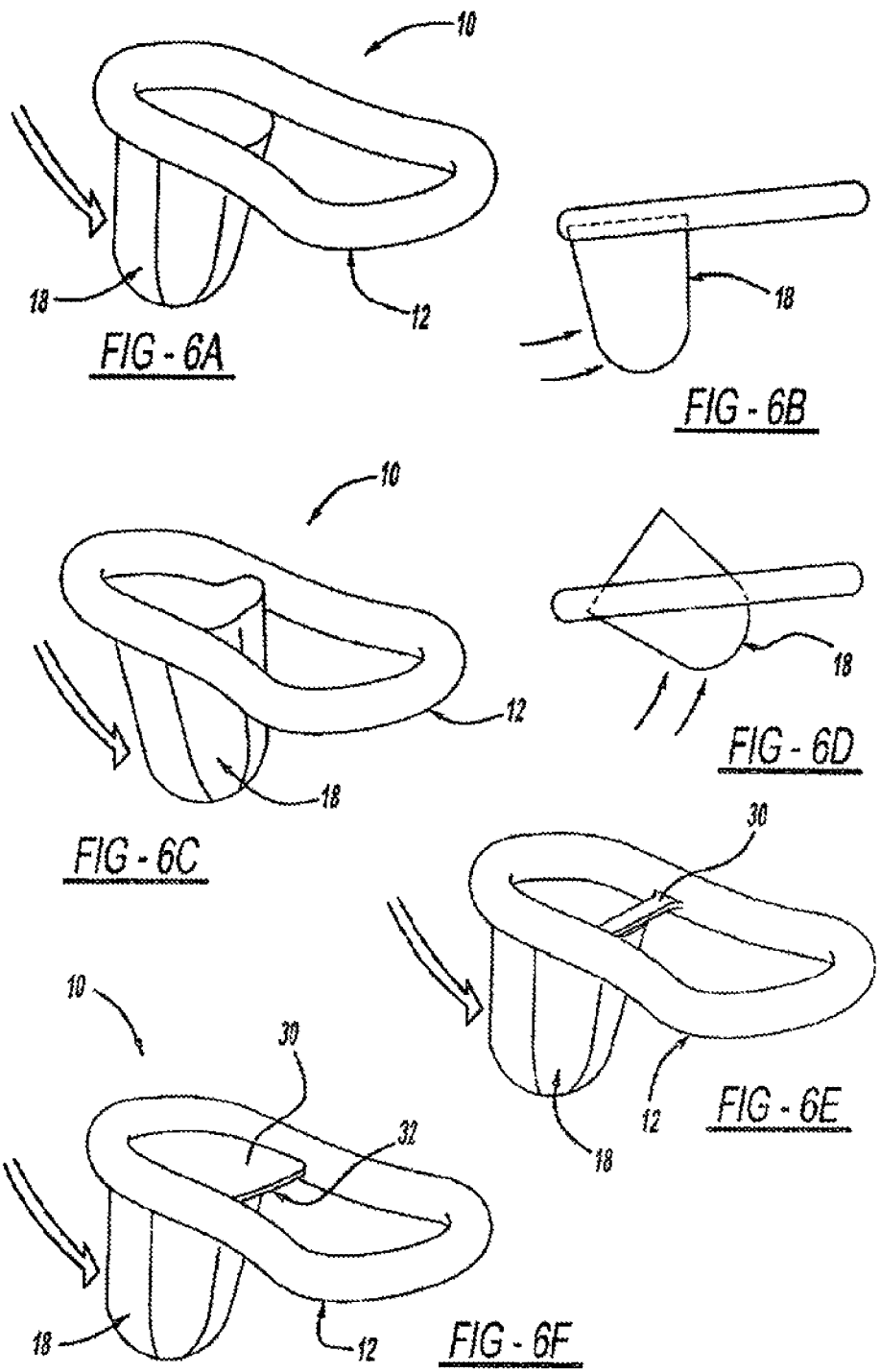

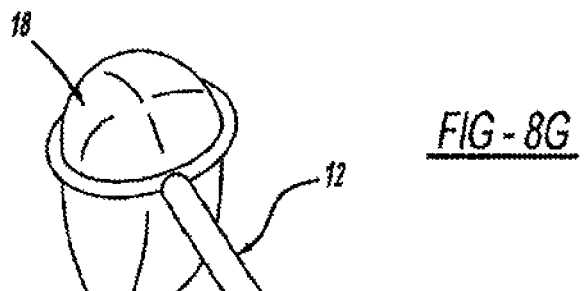
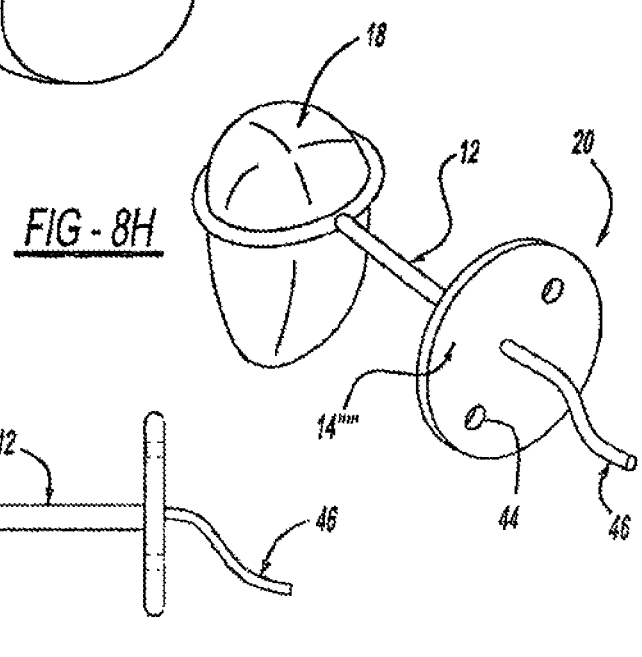
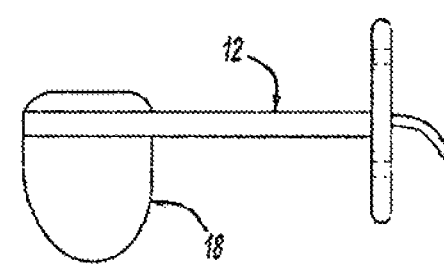
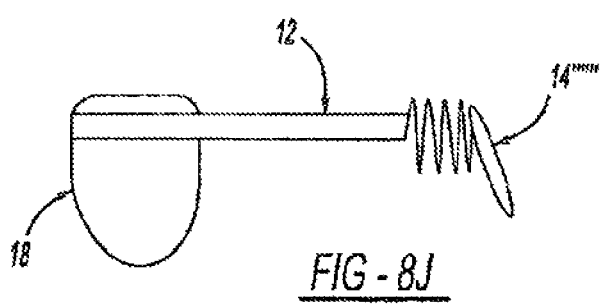

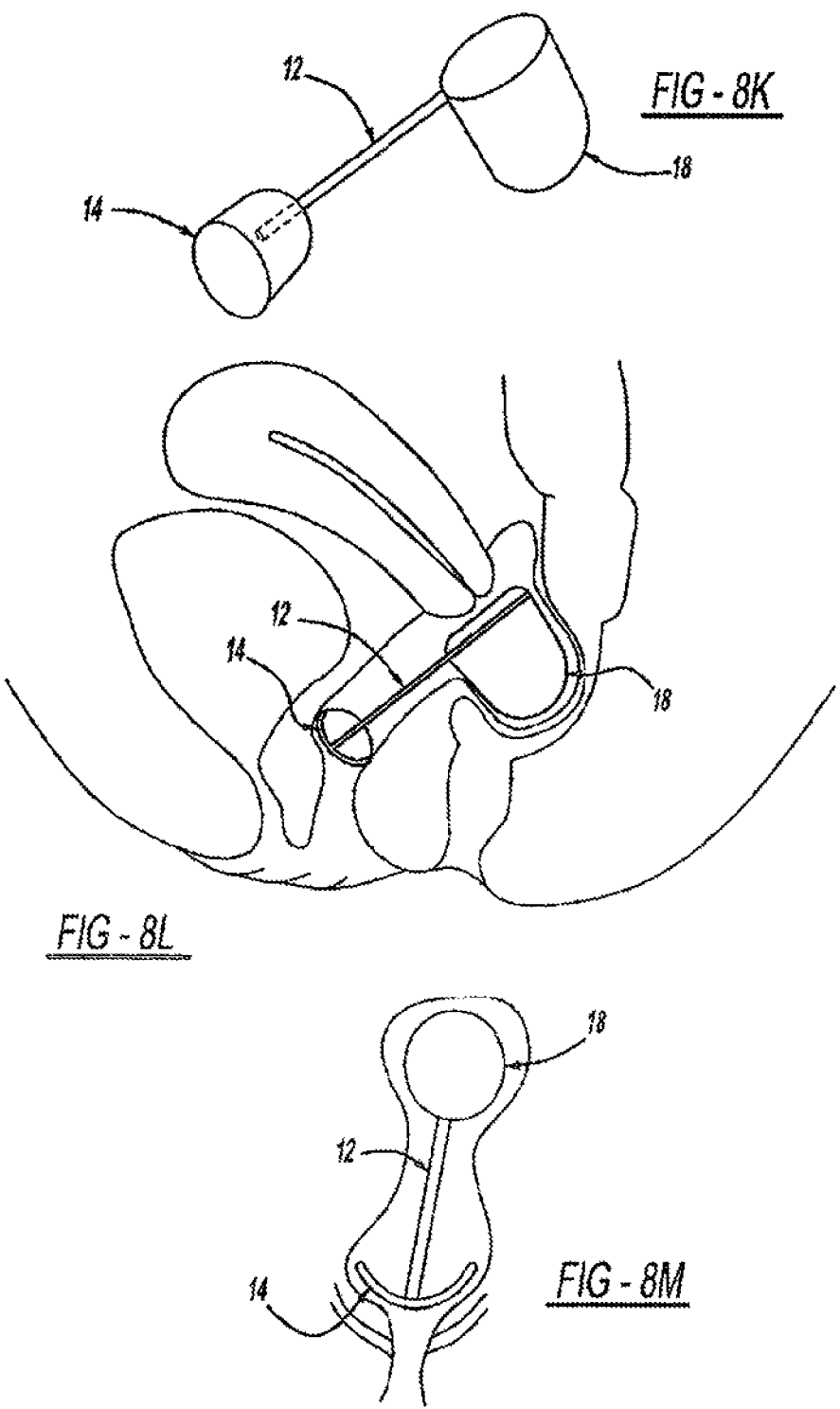

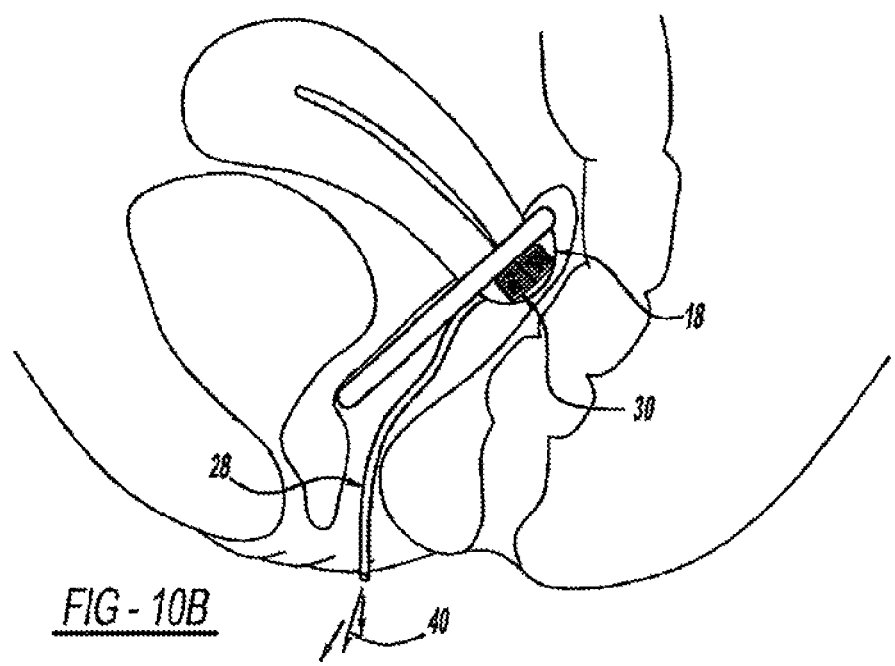
FIG - 10B
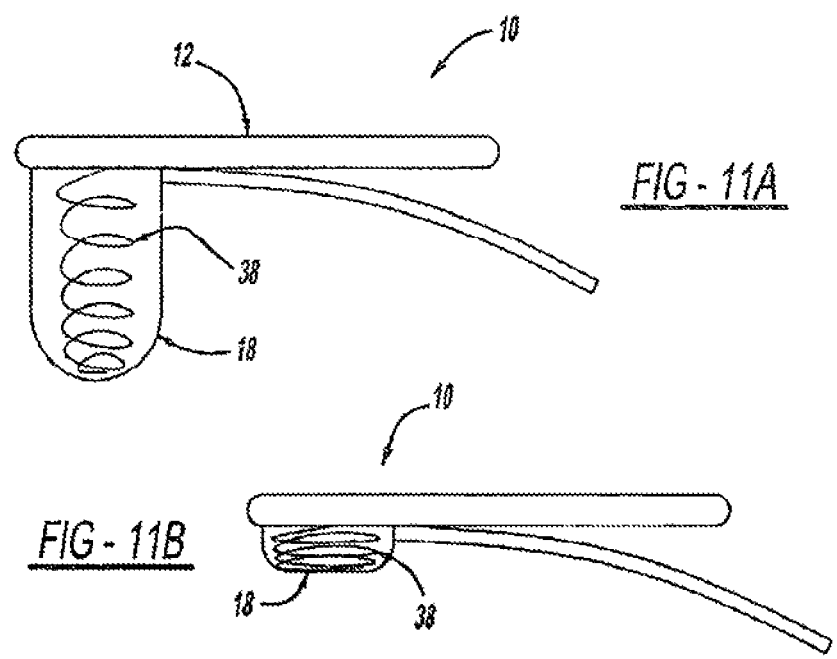
FIG - 11A
FIG - 11B

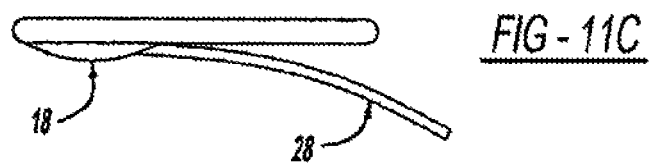
FIG - 11C
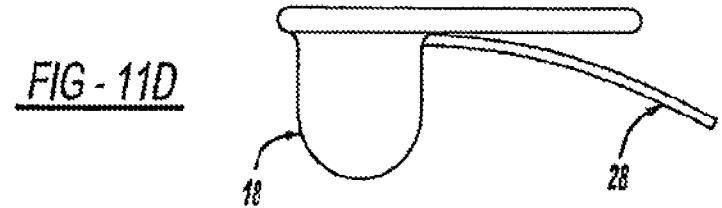
FIG - 11D
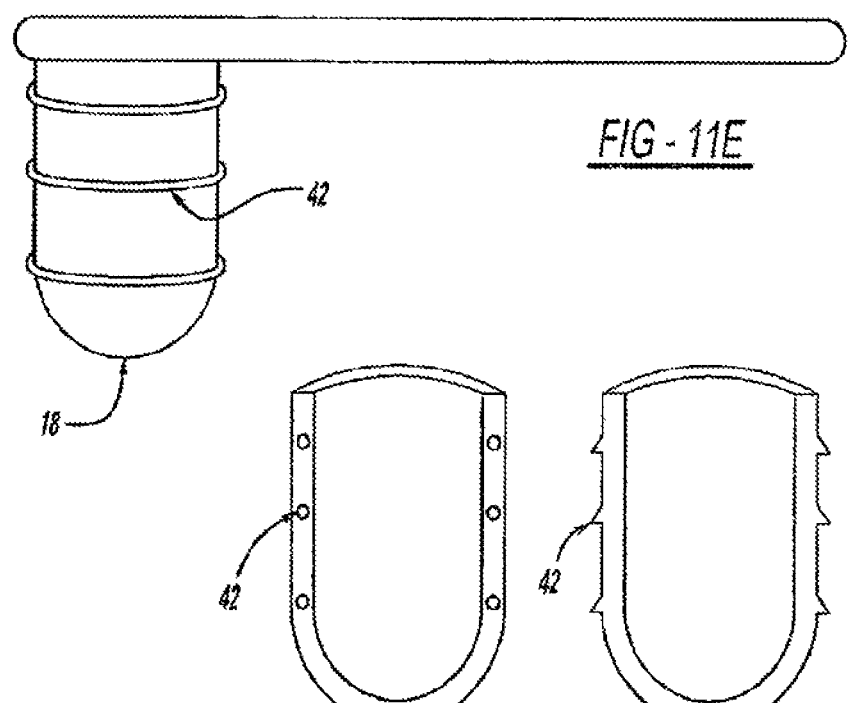
FIG - 11E
FIG - 11F

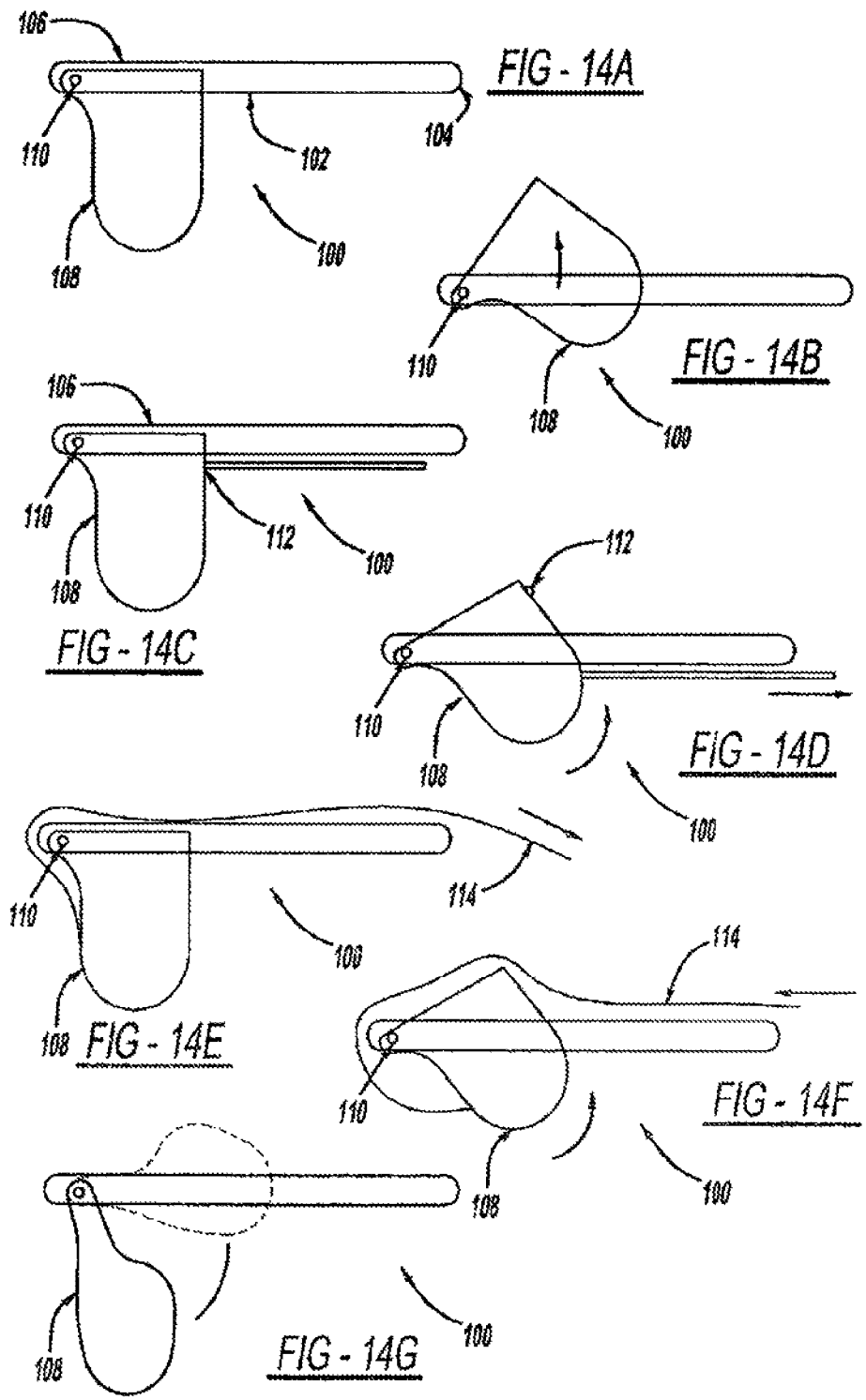

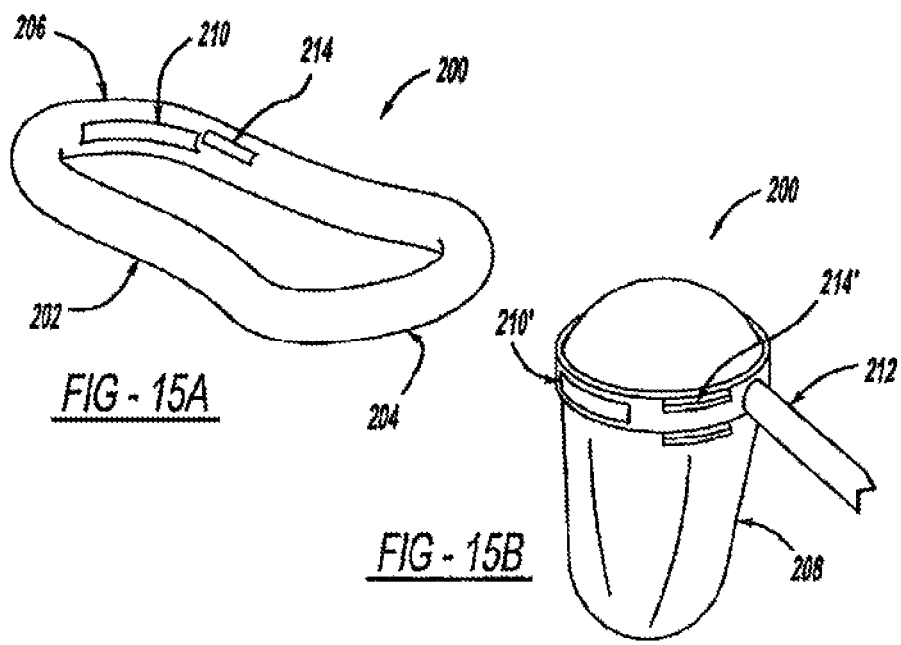
FIG - 15A
FIG - 15B
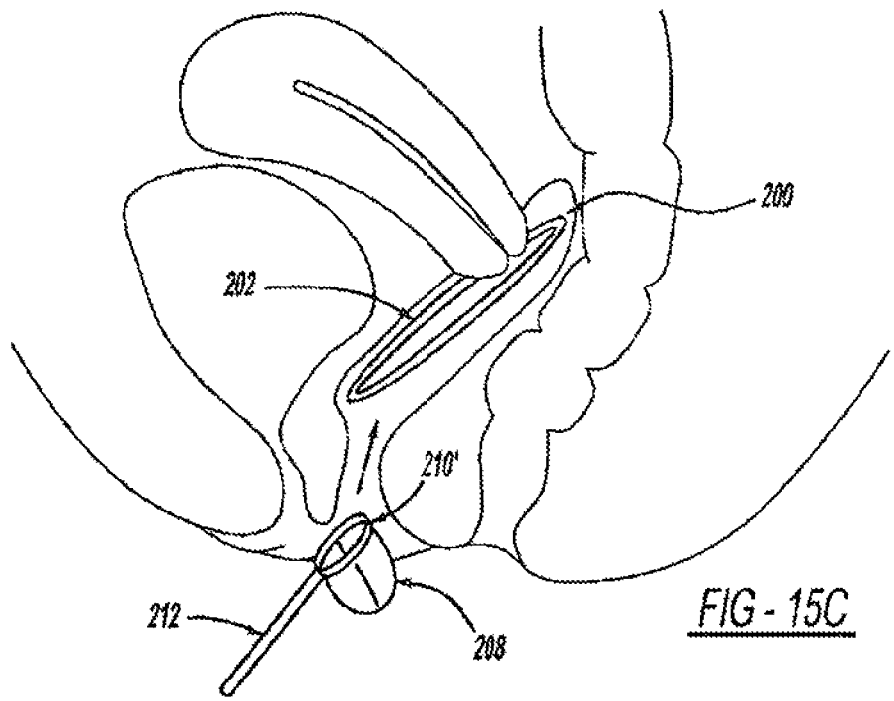
FIG - 15C

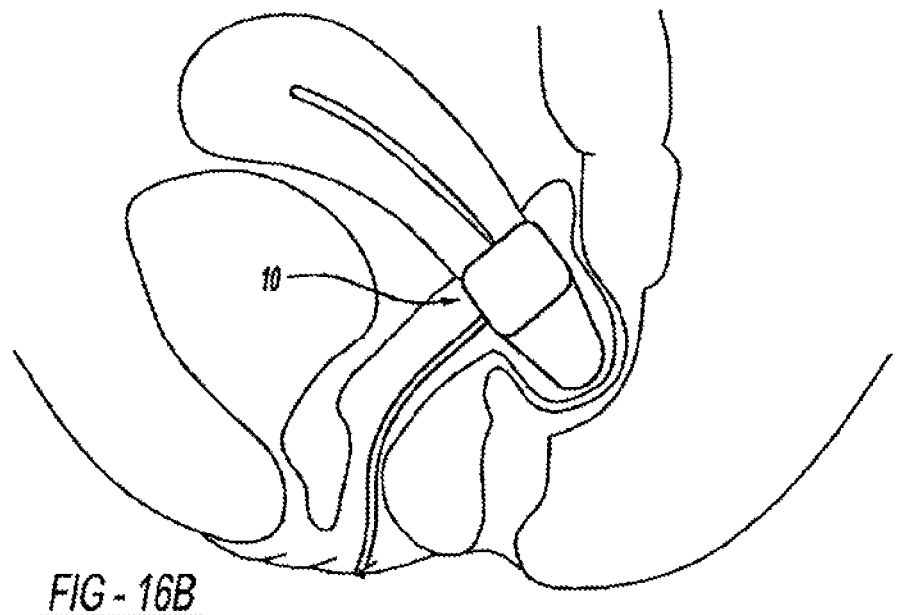
FIG - 16B
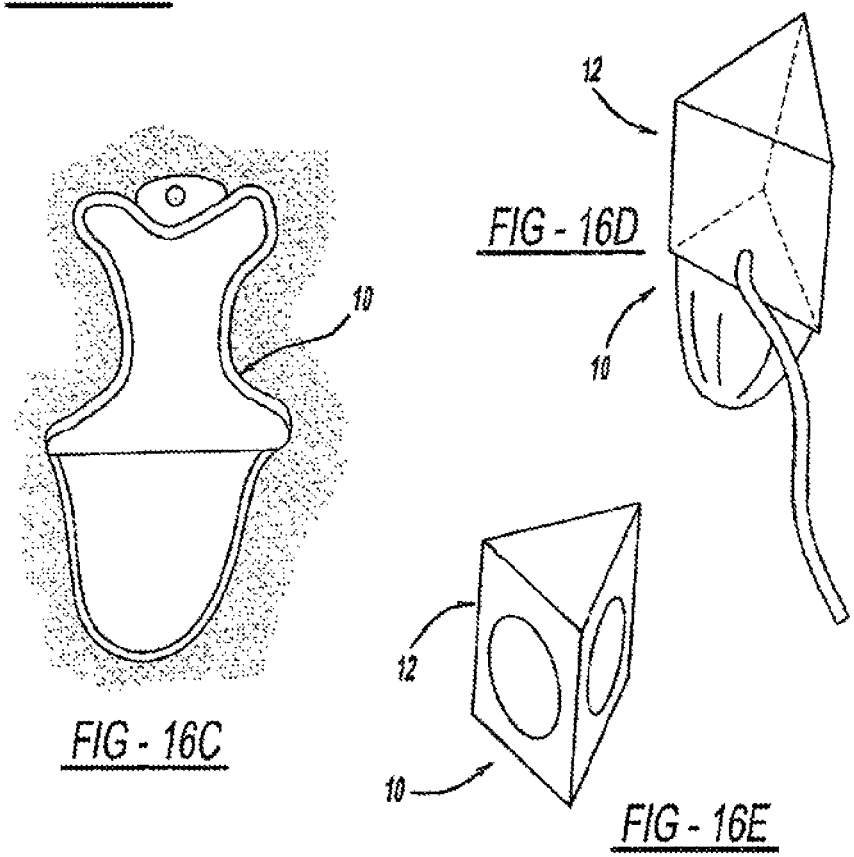
FIG - 16C
FIG - 16D
FIG - 16E

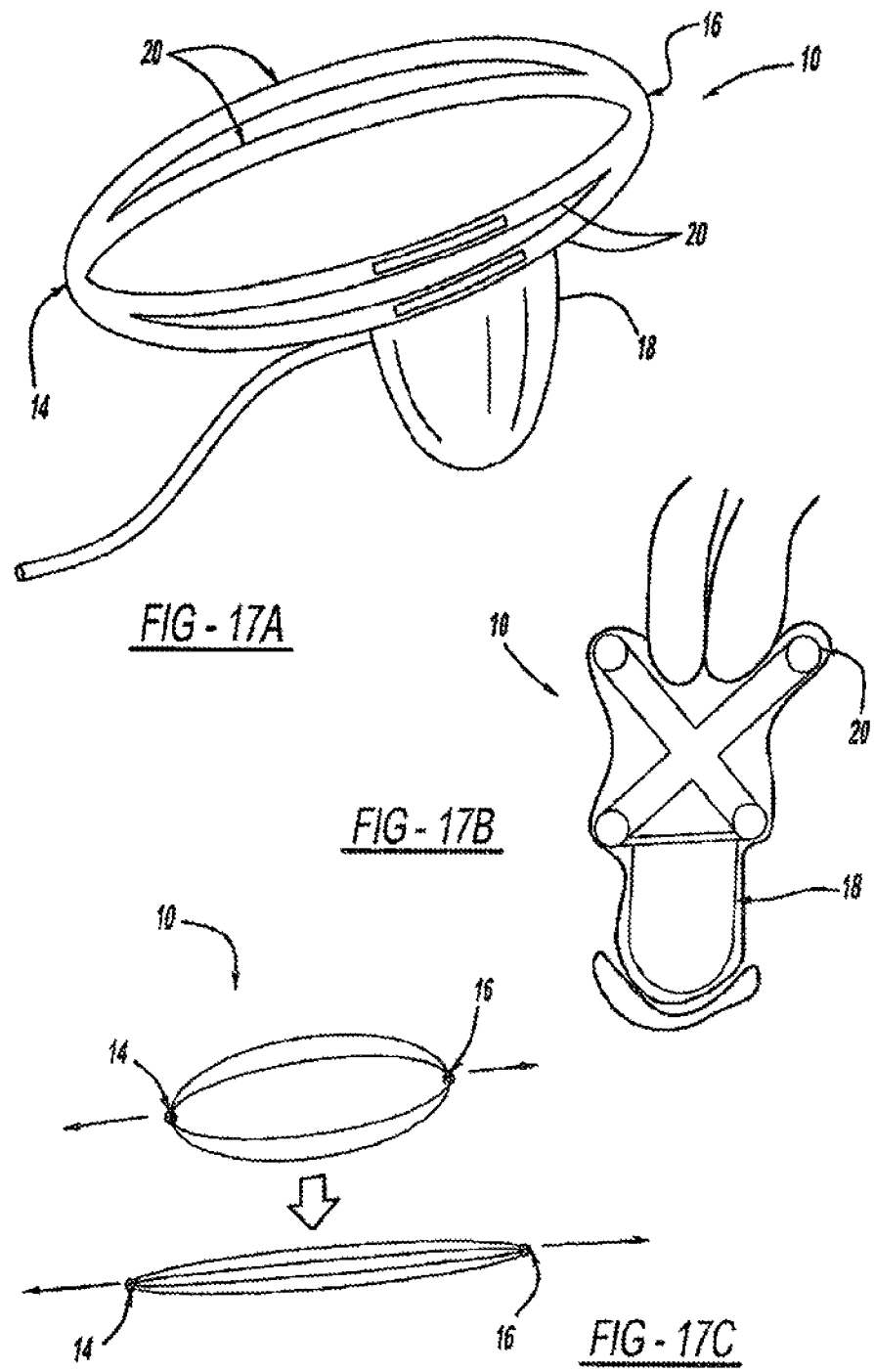

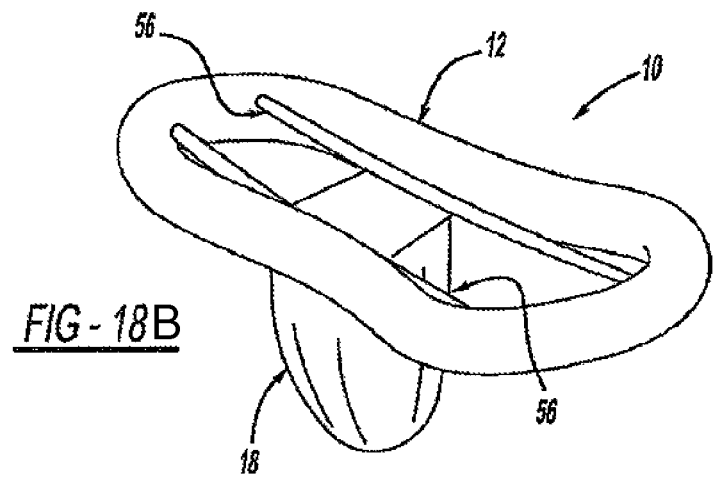
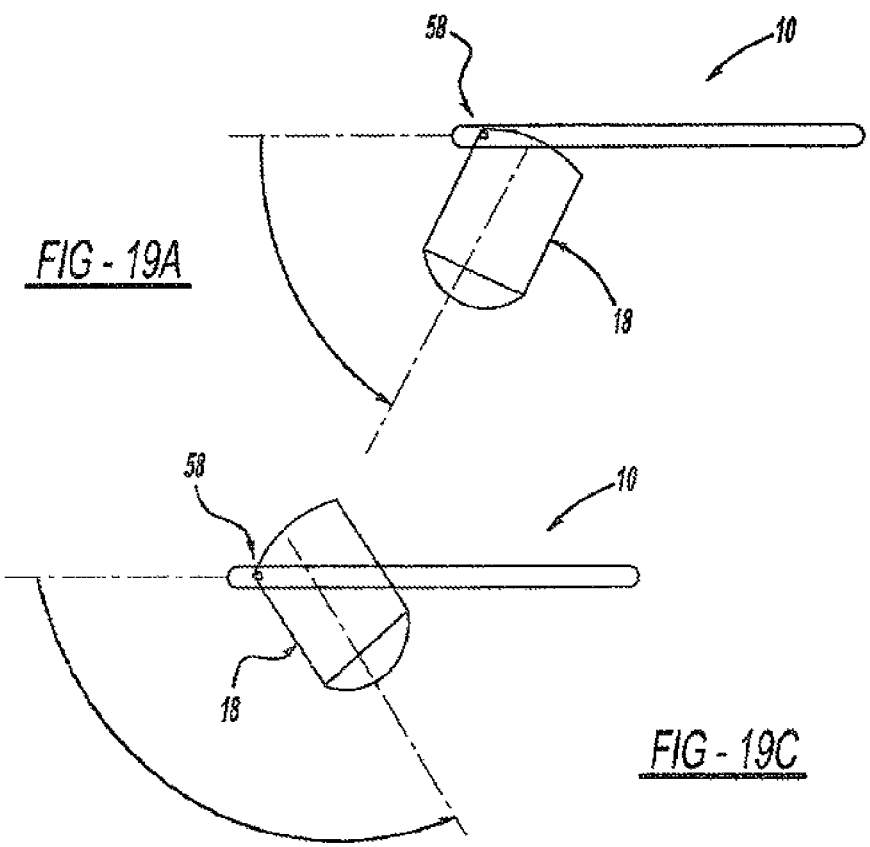

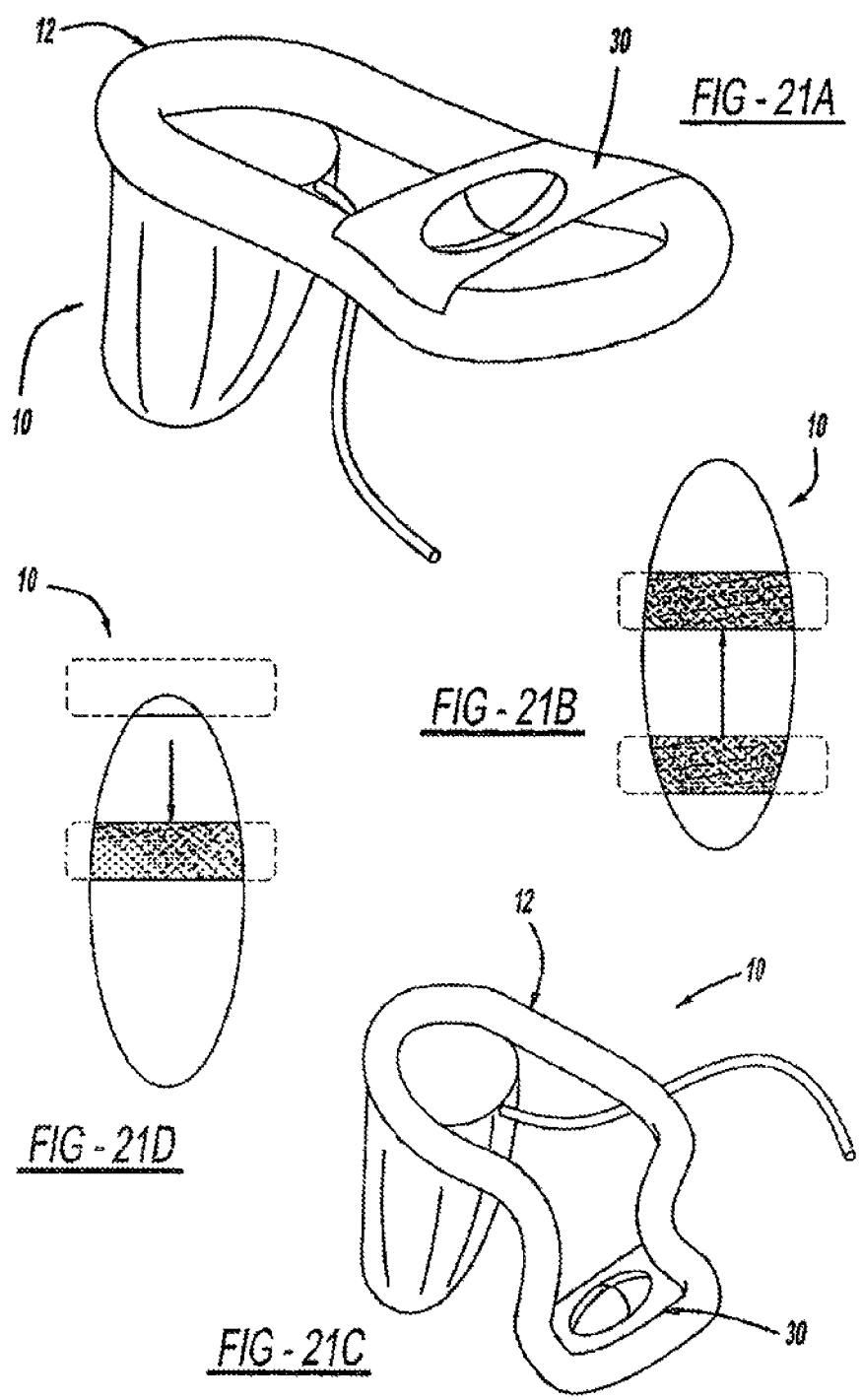

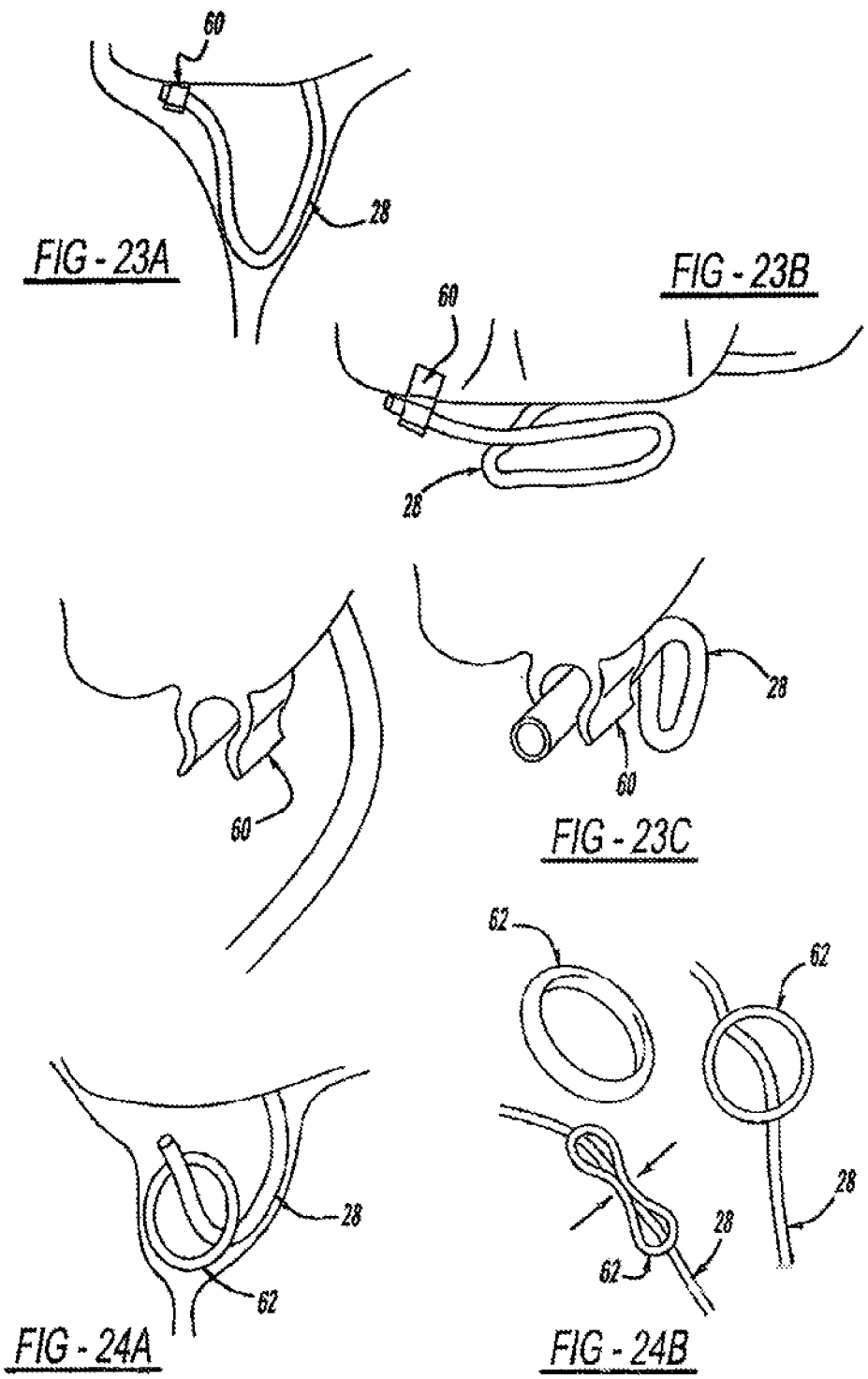

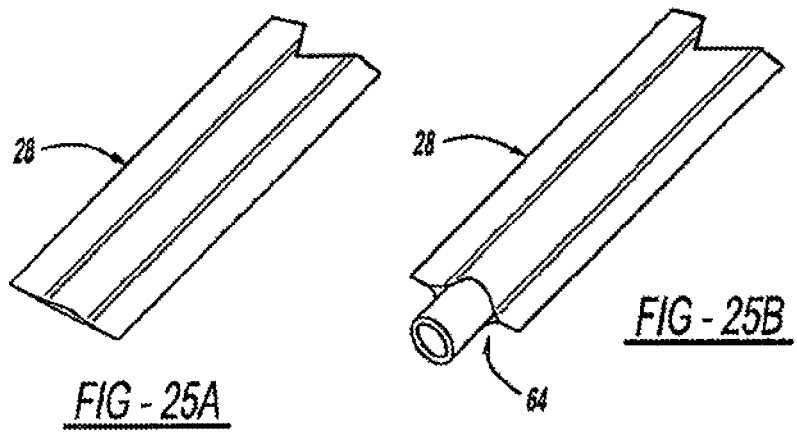
FIG - 25A
FIG - 25B
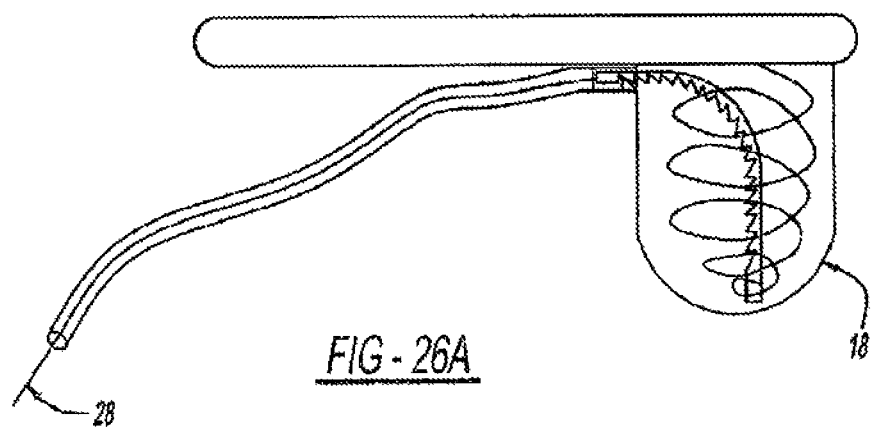
FIG - 26A
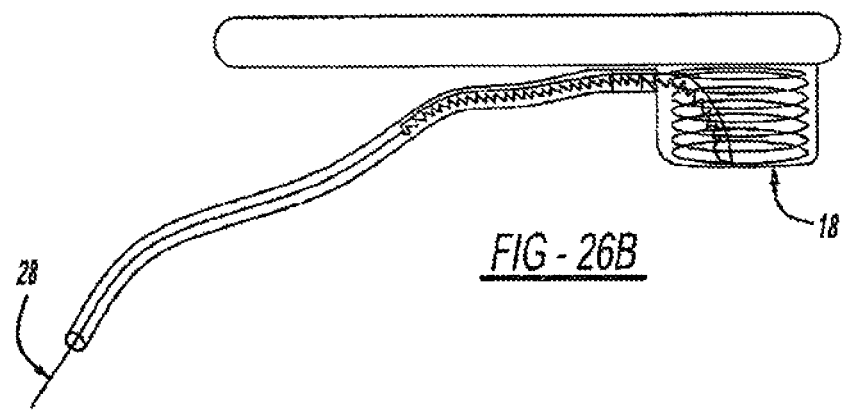
FIG - 26B

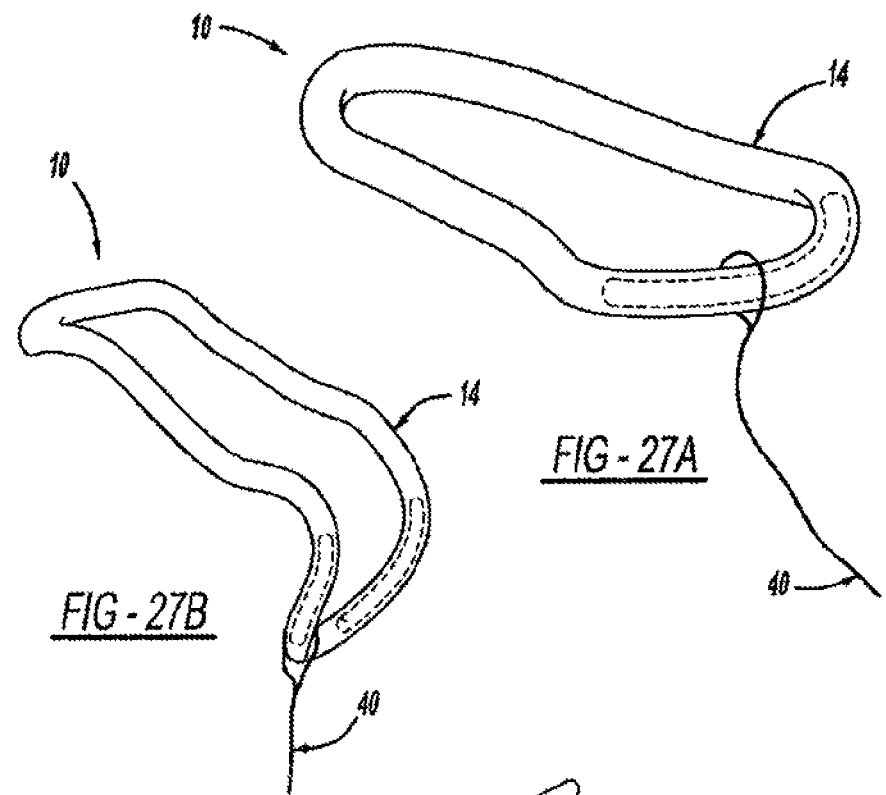
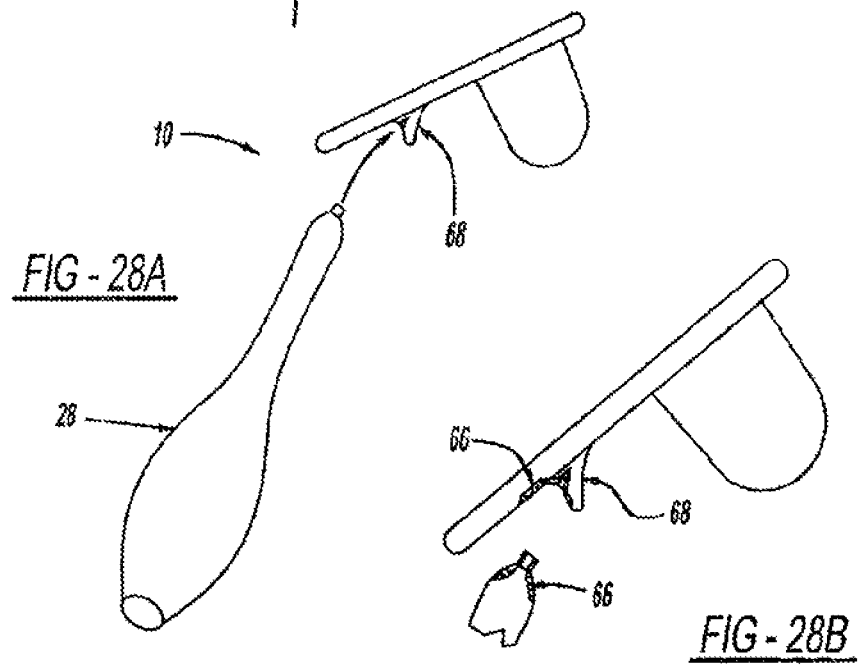

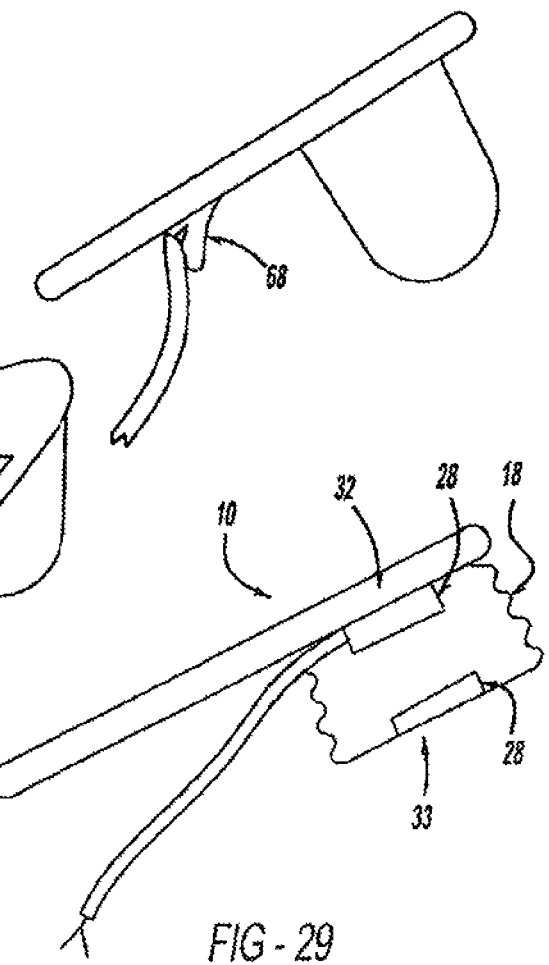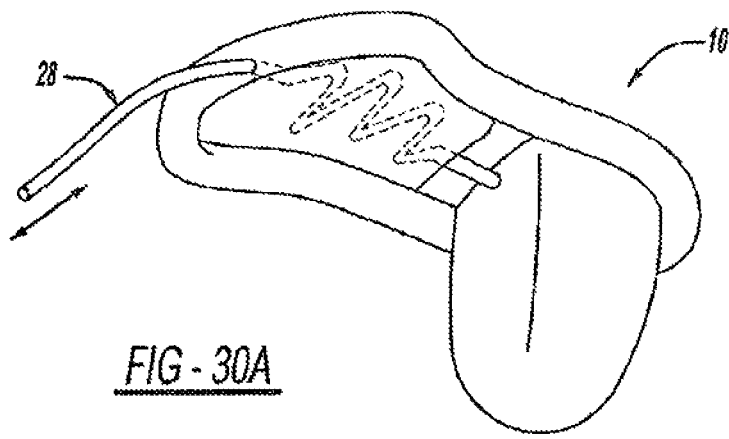

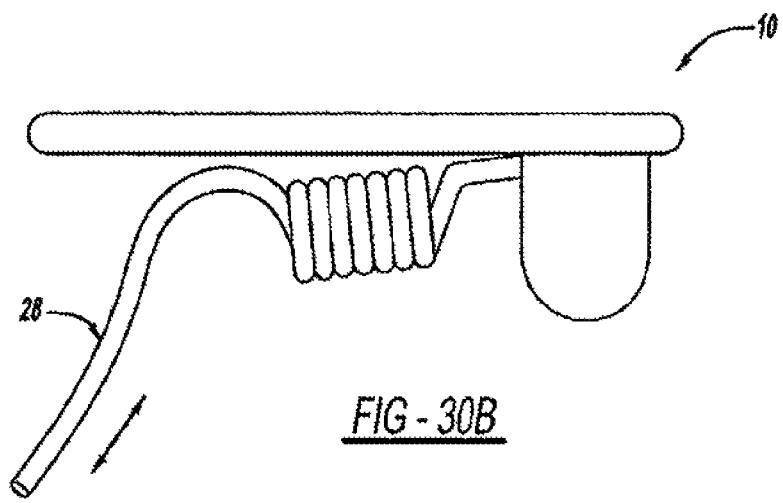
FIG - 30B
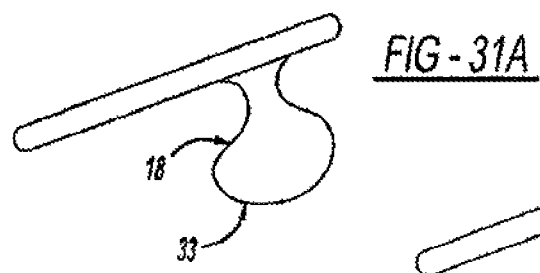
FIG - 31A
FIG - 31B
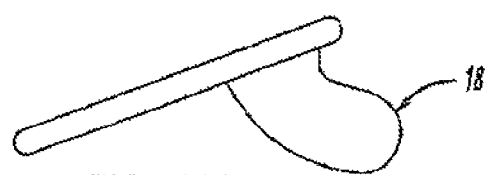
FIG - 31C
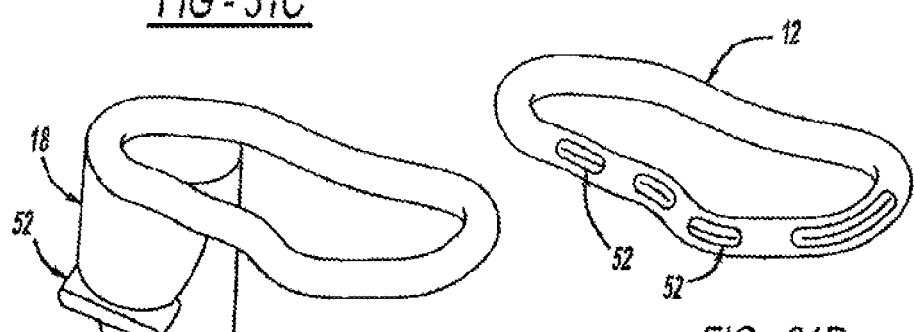
FIG - 31E
FIG - 31D

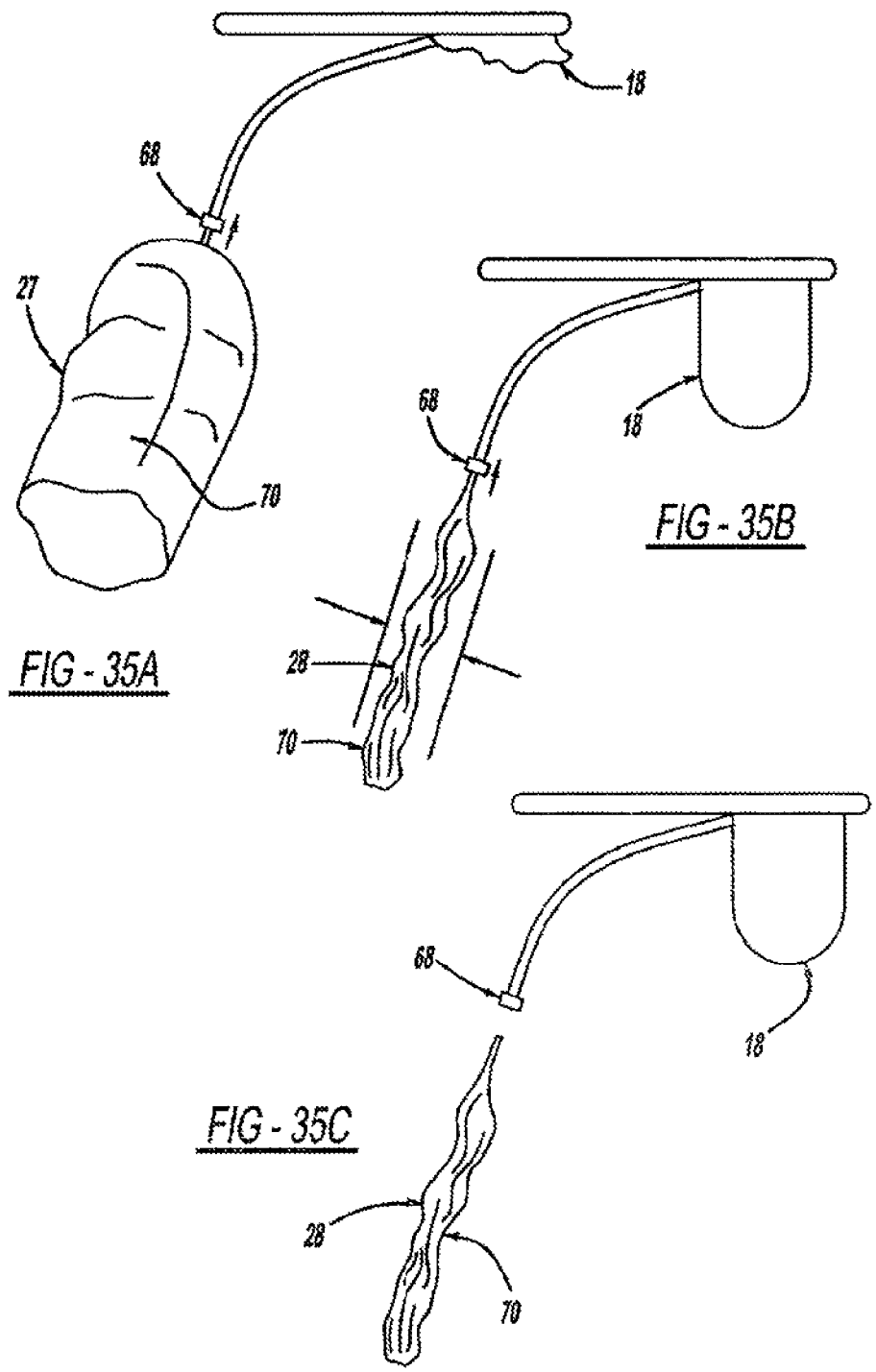

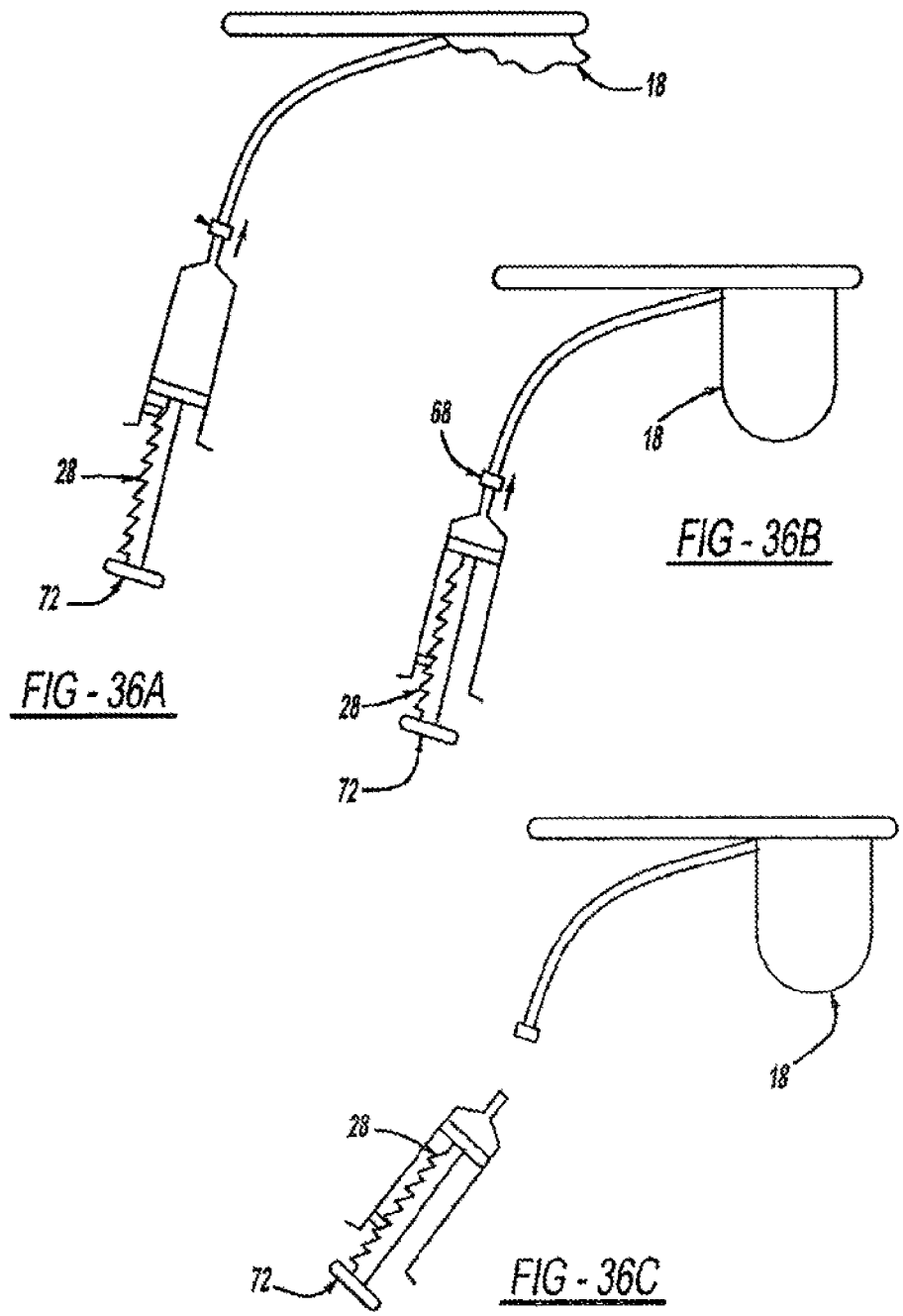

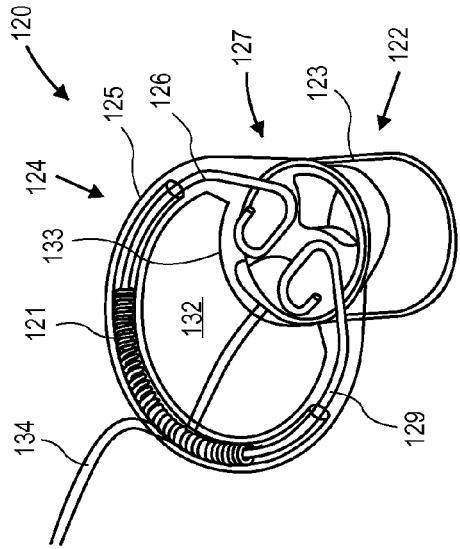
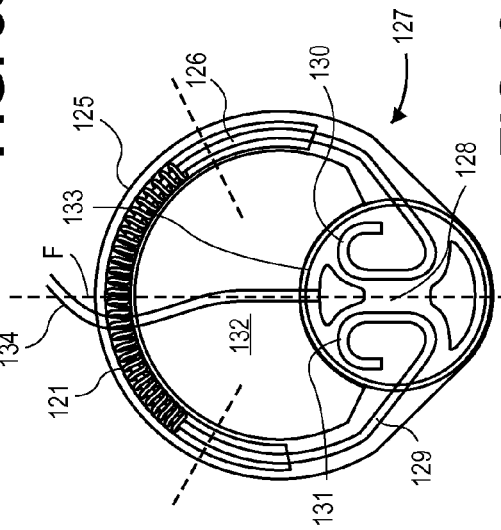
FIG. 38A
FIG. 38B
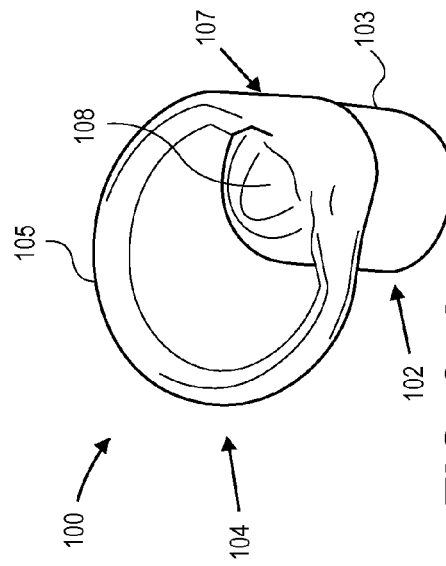
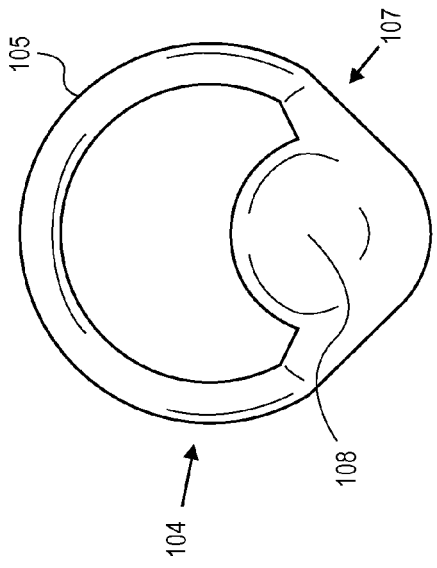
FIG. 37A
FIG. 37B

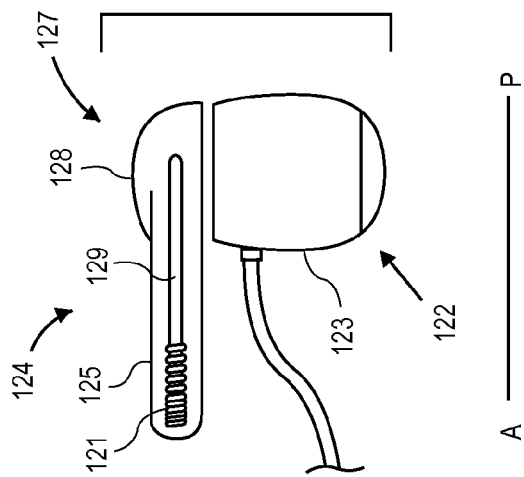
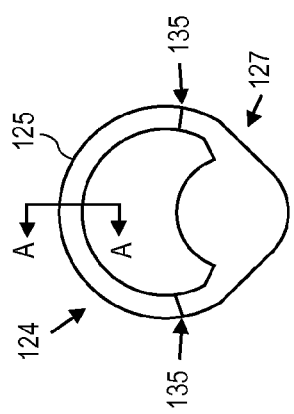
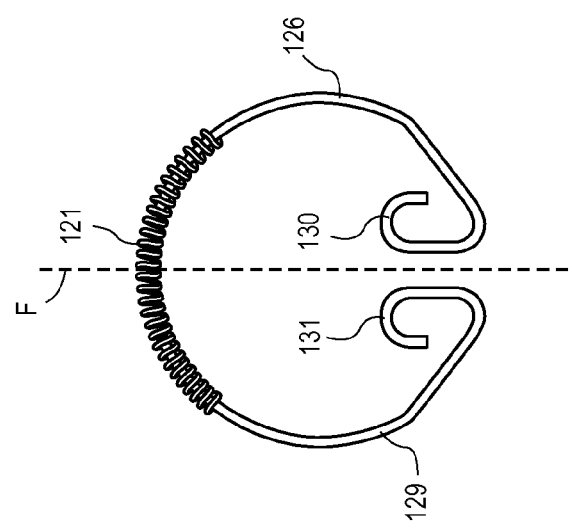
FIG. 38F
FIG. 38D
FIG. 38E
FIG. 38C

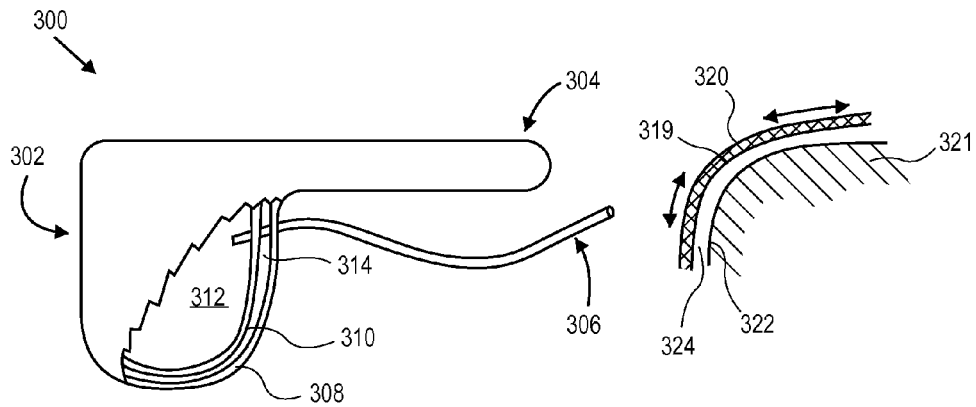
FIG. 49  FIG. 50
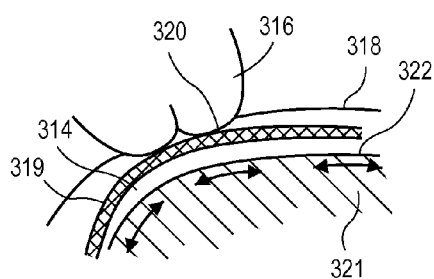
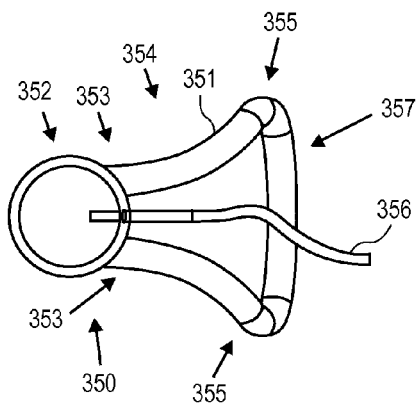
FIG. 51  FIG. 52A
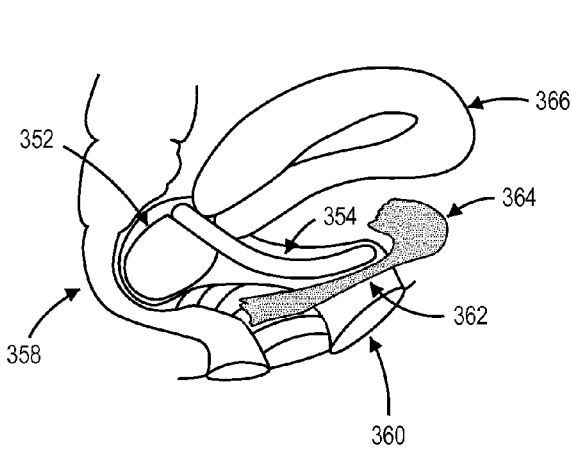
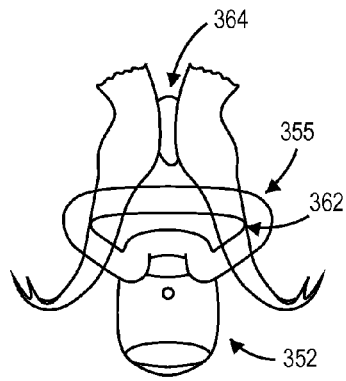
FIG. 52B  FIG. 52C

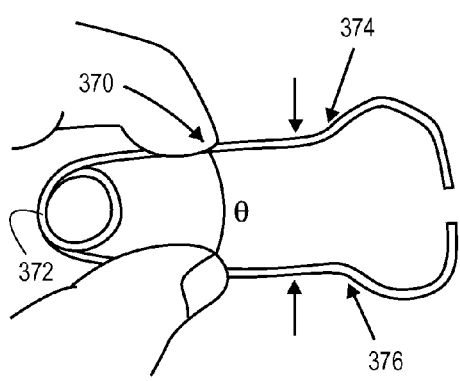
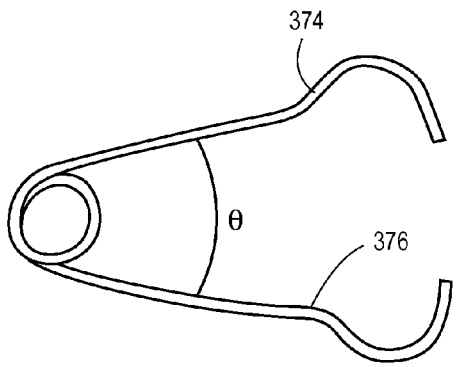
FIG. 53A        FIG. 53B
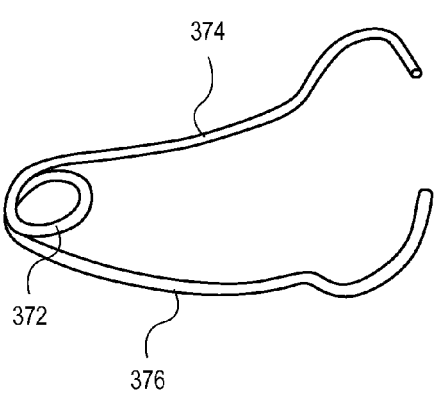
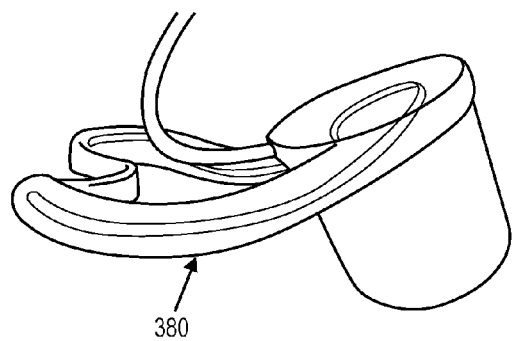
FIG. 53C        FIG. 53D
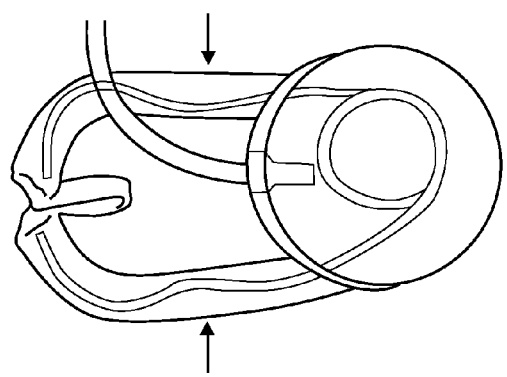
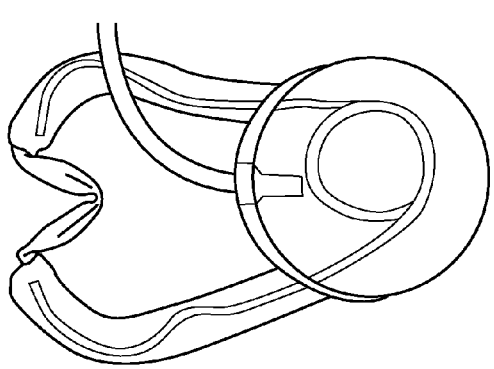
FIG. 53E        FIG. 53F

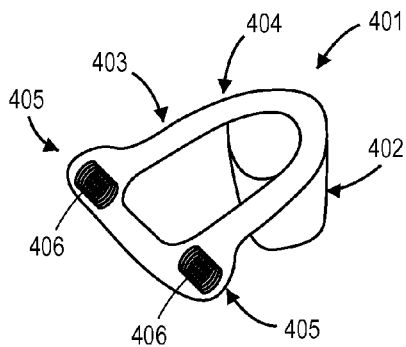
FIG. 56
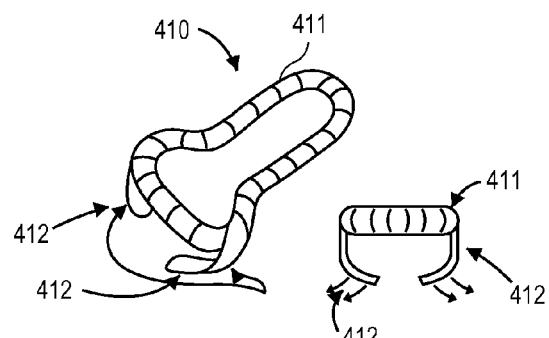
FIG. 57A  FIG. 57B
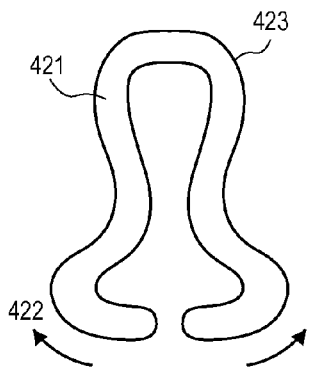
FIG. 58
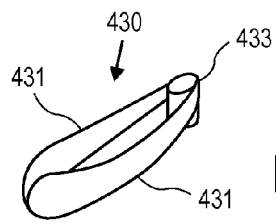
FIG. 59A
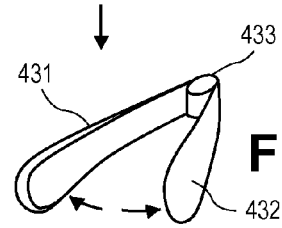
FIG. 59B
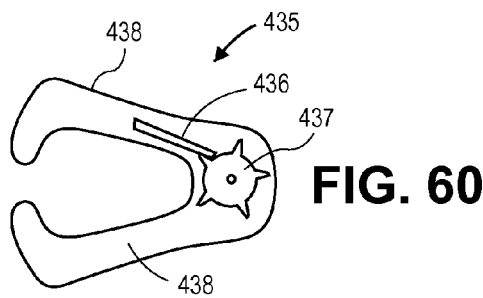
FIG. 60
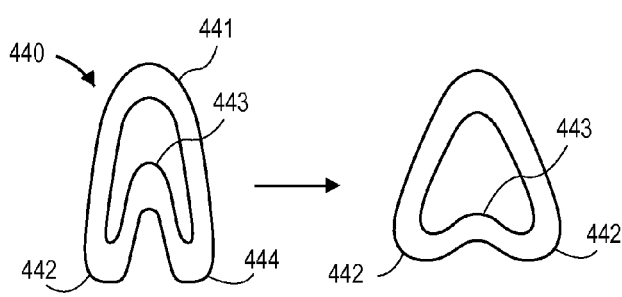
FIG. 61A  FIG. 61B

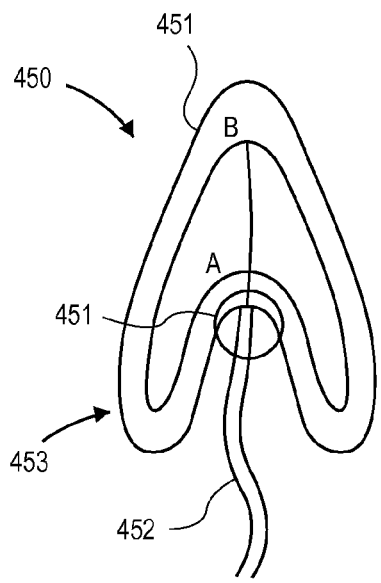
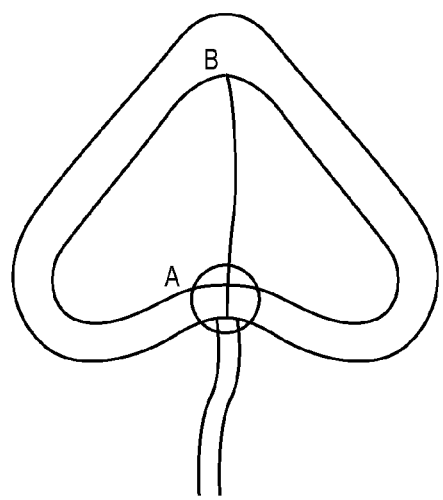
FIG. 62A  FIG. 62B
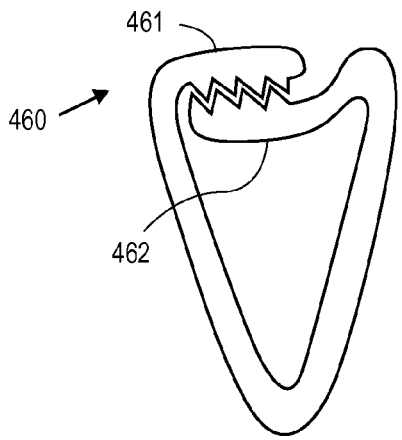
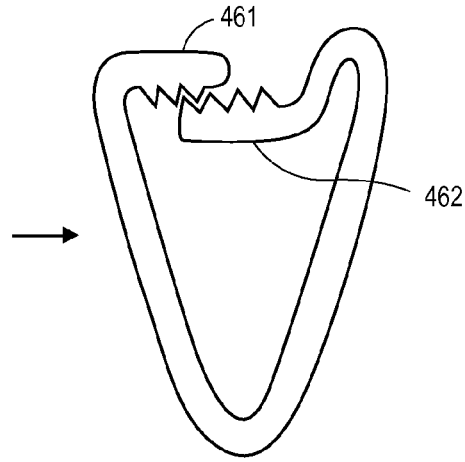
FIG. 63A  FIG. 63B
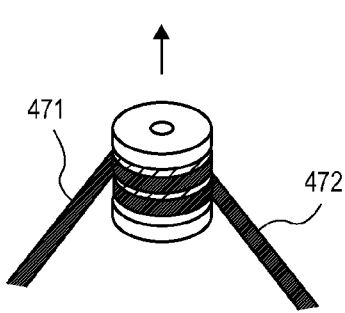
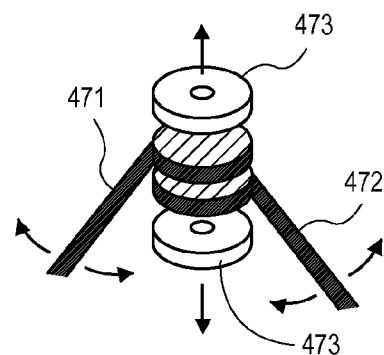
FIG. 64A  FIG. 64B

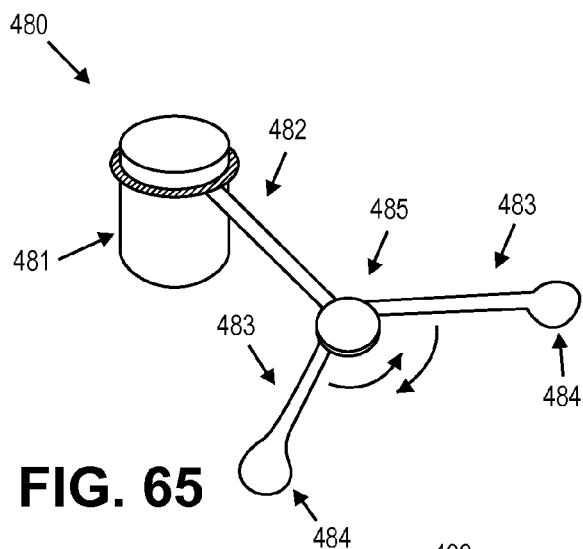
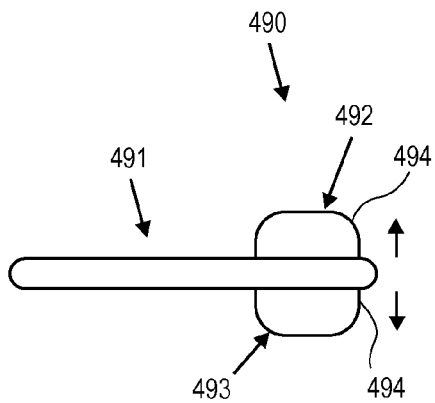
FIG. 65
FIG. 66A
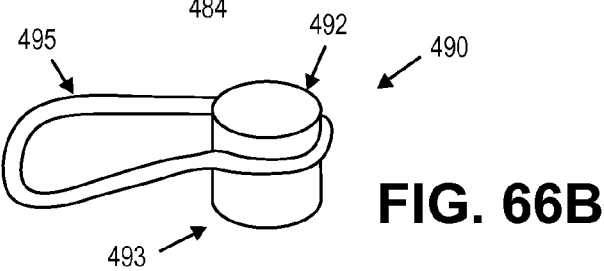
FIG. 66B
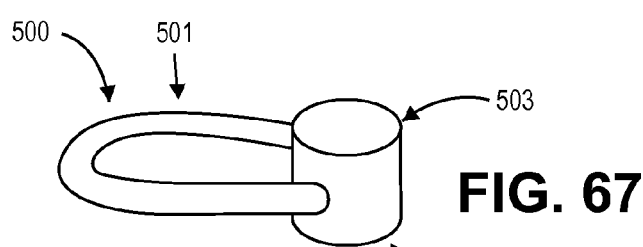
FIG. 67
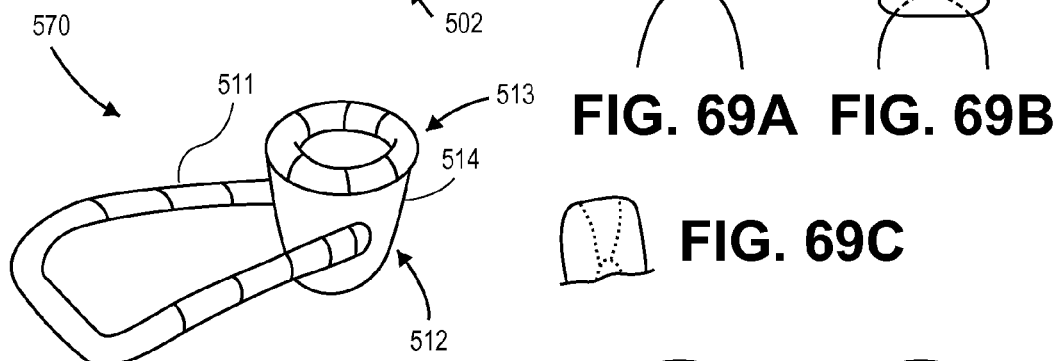
FIG. 68
FIG. 69A    FIG. 69B
FIG. 69C
FIG. 69D    FIG. 69E

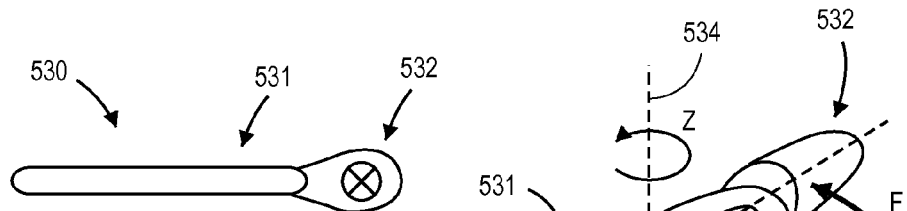
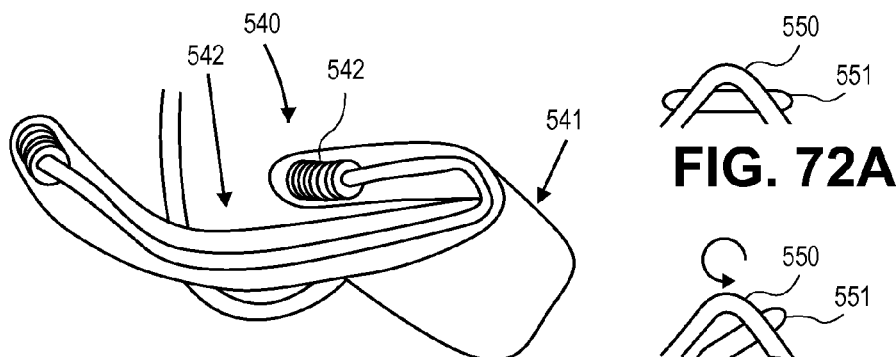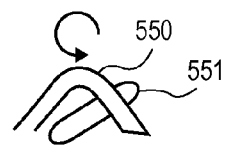
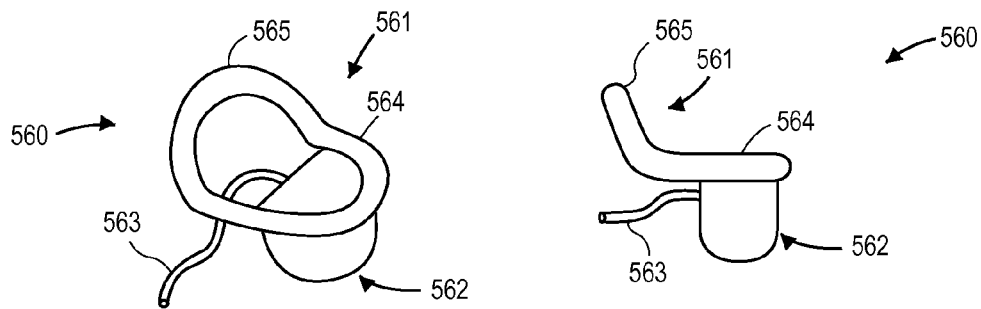
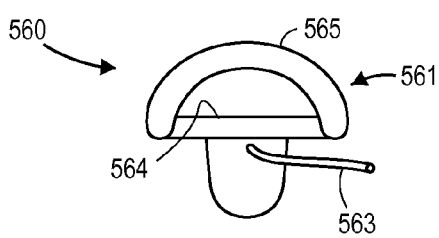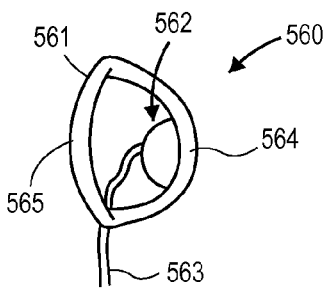

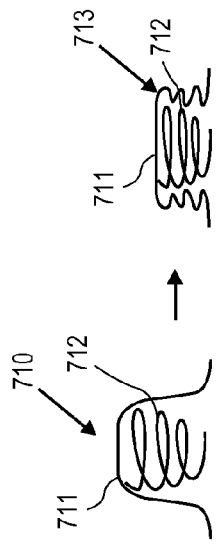
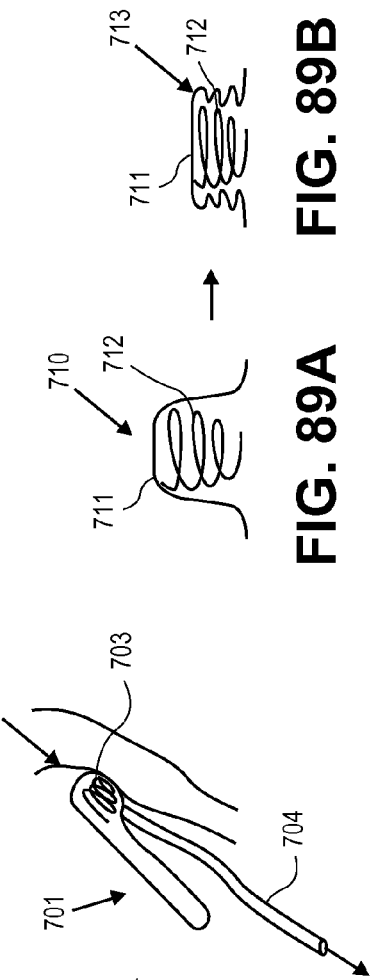
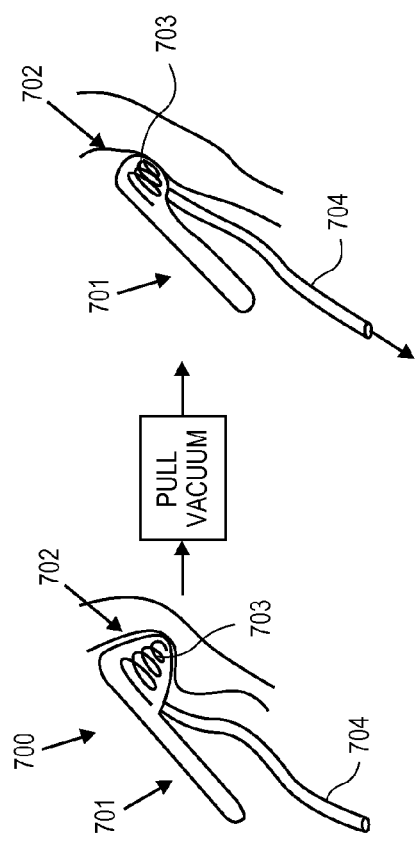
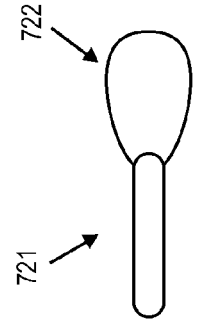
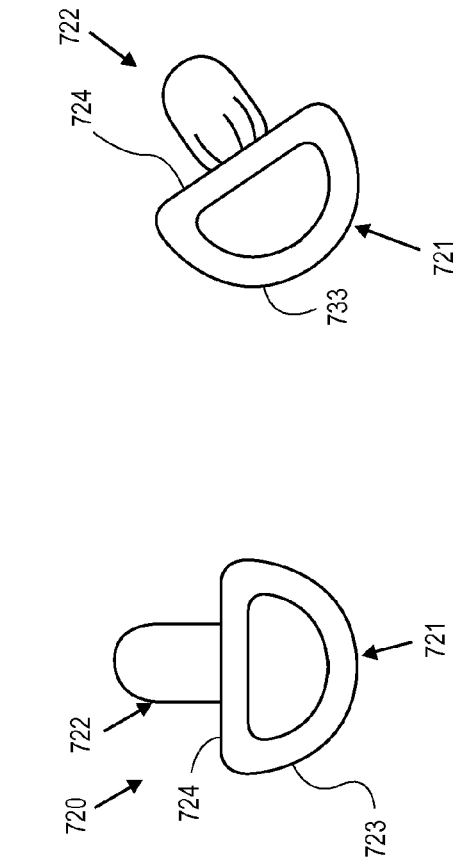

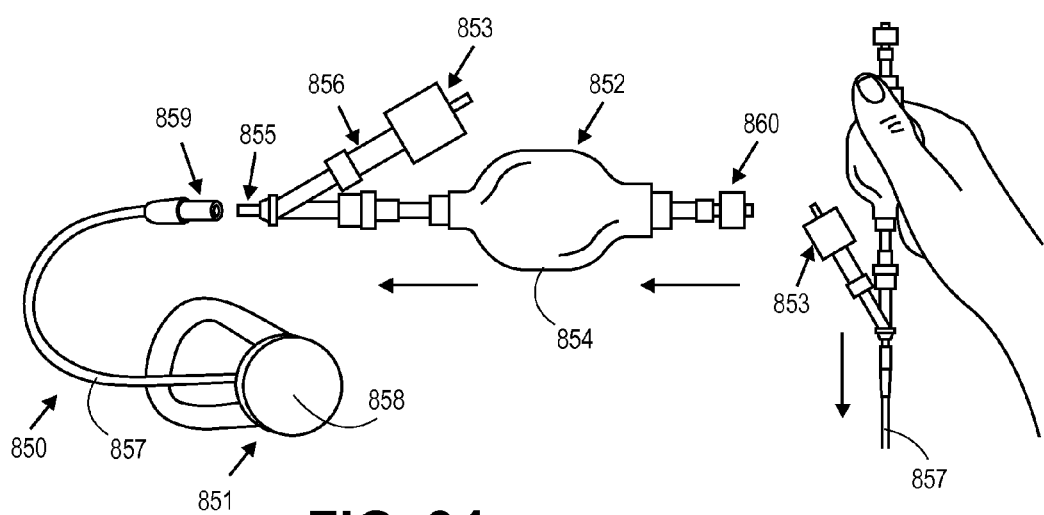
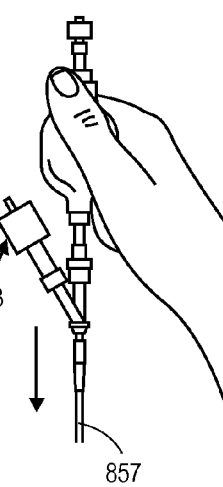
FIG. 94
FIG. 95
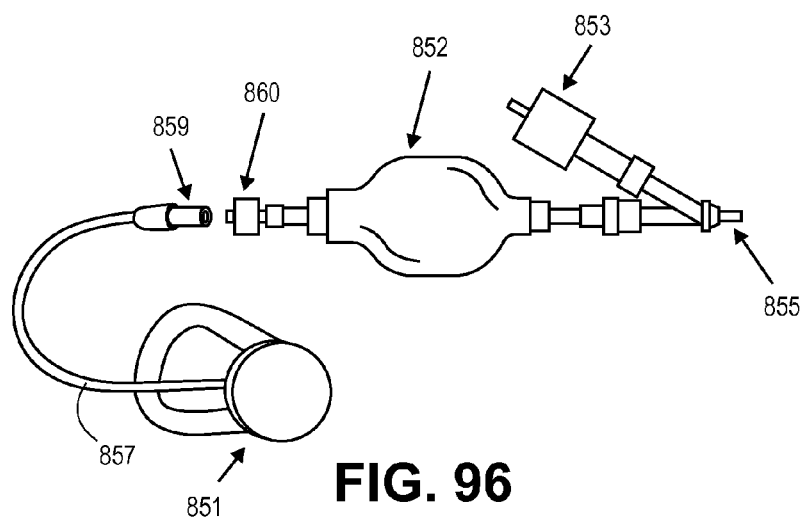
FIG. 96

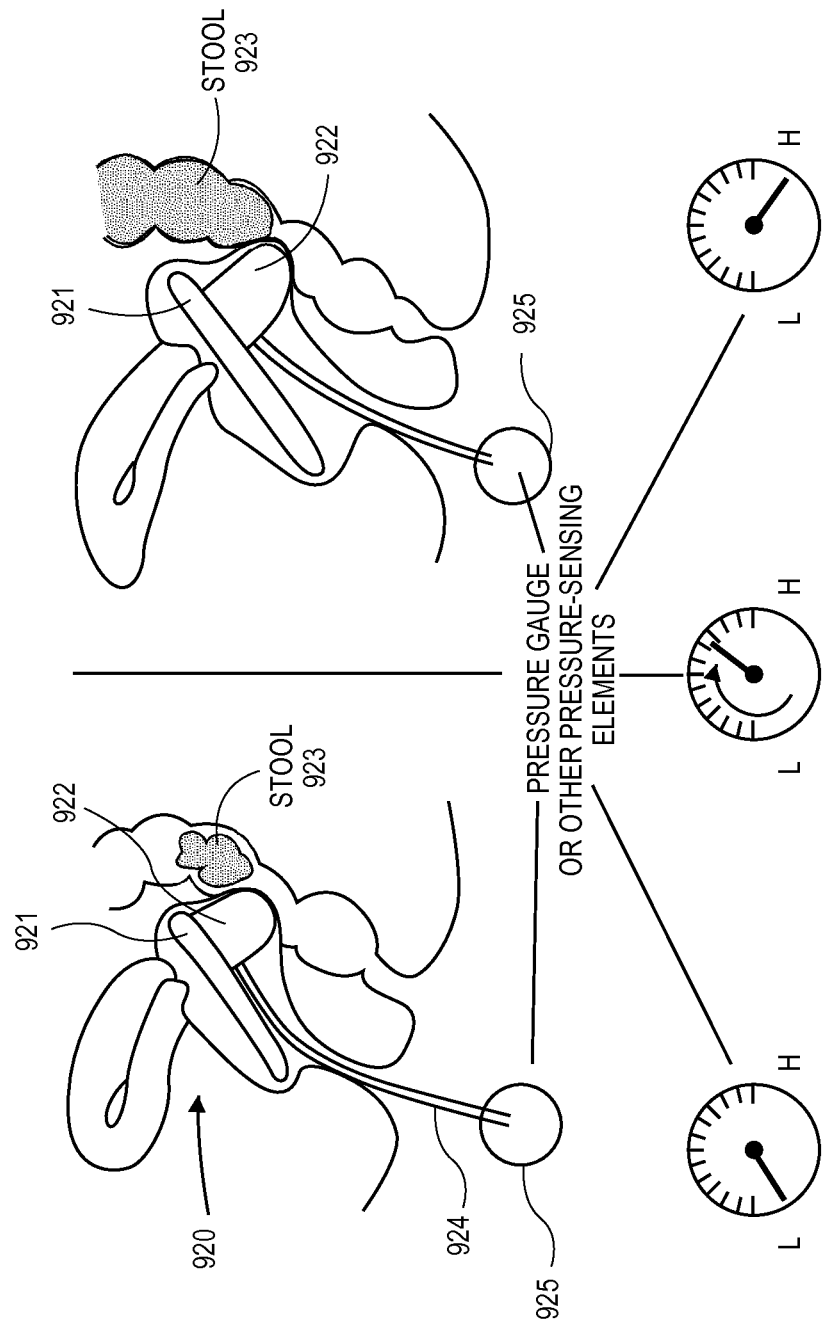

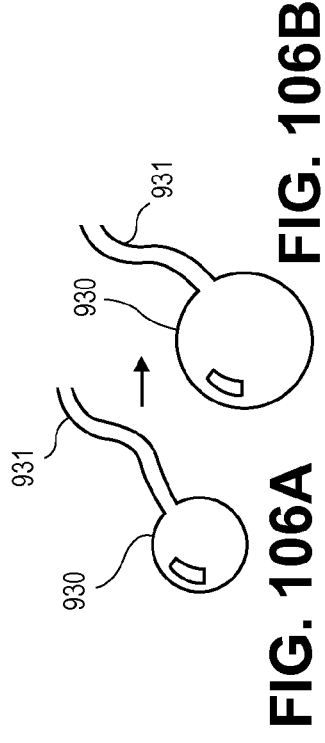
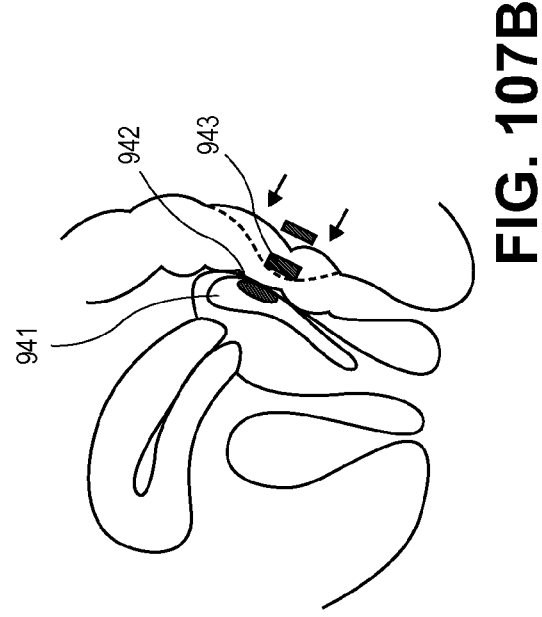
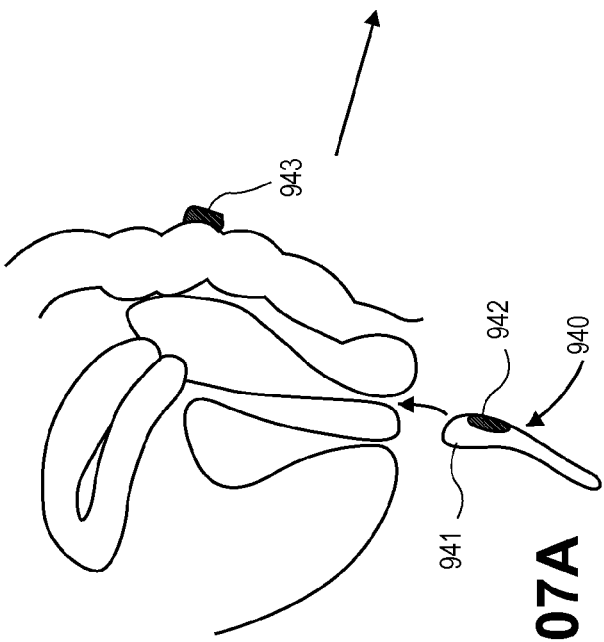

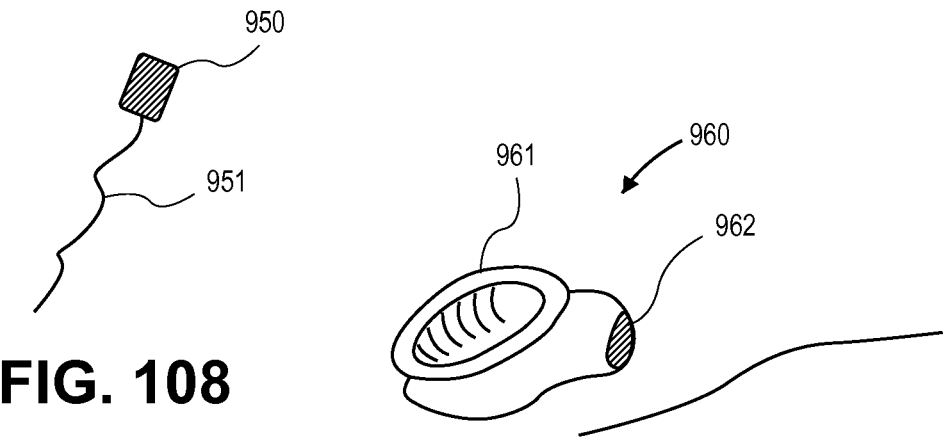
FIG. 108
FIG. 109
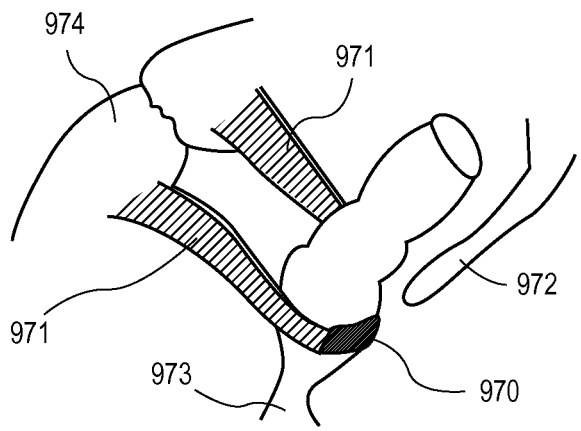
FIG. 110
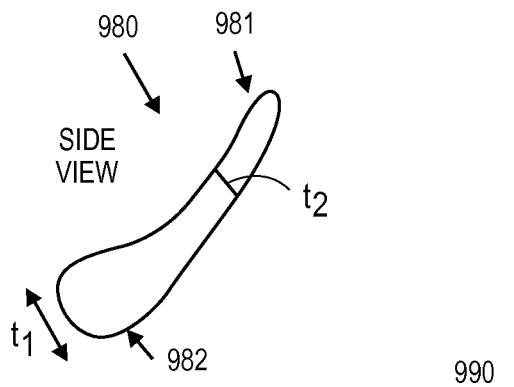
FIG. 111A
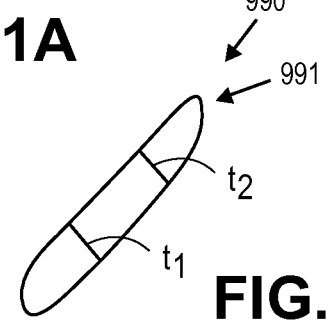
FIG. 111B
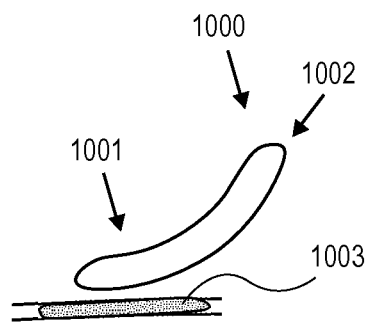
FIG. 112

INTRA-VAGINAL DEVICES AND METHODS FOR TREATING FECAL INCONTINENCE

CROSS REFERENCE TO RELATED APPLICATIONS

This application is a continuation of pending U.S. Application No. 13/625,683, filed Sep. 24, 2012, which is a continuation-in-part of pending U.S. application Ser. No. 13/635,598 filed on Sep. 17, 2012, which is a national phase application of International Application No. PCT/US2011/028691, filed Mar. 16, 2011, which claims the priority of U.S. Provisional Application No. 61/314,335 filed Mar. 16, 2010 and U.S. Provisional Application No. 61/367,418 filed Jul. 25, 2010. Said application Ser. No. 13/625,683 also claims priority to U.S. Provisional Application No. 61/538,095 filed Sep. 22, 2011 and to U.S. Provisional Application No. 61/704,433 filed Sep. 21, 2012.

All of the aforementioned applications are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Fecal incontinence (FI) is one of the most common health problems in women. The prevalence of FI is not well understood, primarily because the stigma surrounding the condition and the lack of viable treatments have deterred many women from seeking medical care. Recent general population surveys indicate the prevalence of FI at 9% to 12% and as high as 24% in older women. These studies have also shown that, although prevalence increases somewhat with age, younger women have surprisingly high prevalence rates. The condition is both physically limiting and emotionally devastating. Those afflicted are often forced to withdraw from social and professional activities and often face problems in their private personal relationships.

The cause of FI is multifactorial and not completely understood. Often times, women with FI have a history of damage to the pelvic floor stemming from pregnancy and childbirth. Damage can involve the internal and external anal sphincters, pelvic floor muscles, and associated nerves (e.g., pudendal nerve). Puerperal damage to these structures may not manifest until later in life, possibly due to age-related changes in rectal sensation, compliance, and volume, in addition to further weakening of the sphincters and pelvic floor muscles. Many women with FI have multiple defects in their continence system, making effective treatment particularly difficult.

Existing treatments for FI have had limited success. Conservative medical management, such as dietary modification, antimotility agents, and biofeedback, has not been very effective. Overlapping sphincter repair is one of the most common surgical approaches. However, long-term success rates have been less than 40% and the procedure is usually only applicable for certain, repairable sphincter defects. The implantable artificial bowel sphincter (American Medical System's Acticon® Neosphincter) is a surgical device that gives the patient dynamic control of the opening and closing of the anorectal canal. This mechanism of dynamic control has shown effectiveness; however, the high morbidity related to its invasive nature has greatly limited its applicability. Such surgical interventions also require inpatient hospitalization and prolonged recovery. Recently, sacral nerve stimulation (SNS) has been used to treat FI. Its mechanism is not fully understood and is applicable to patients willing to undergo a permanent, surgical implant. Injectable bulking agents, such as dextranomer in stabilised hyaluronic acid, have been used to treat FI, but they have shown limited efficacy over longer durations. Without viable treatments available, most FI patients are resigned to coping with the condition by using products such as pads and adult diapers.

An intra-vaginal device adapted to control stool passage through the rectum could provide a new way of treating FI in women.

U.S. Patent App. Pub. No. 2006/0211911 to Jao, et al. ("Jao") discloses a vaginal insert having a cylindrical front projection 11 and head 20. In use, and as shown in FIG. 6, a user, holding head 20, inserts the cylindrical front projection 11 into the vagina 30 to push the rectovaginal septum 50 outward against the rectum 40, thereby guiding accumulated excrement 70 back to the rectum 40. In general, Jao describes a device that is repeatedly and manually inserted and manipulated to aid in the removal of accumulated stool, and fails to describe occluding the rectum to prevent the passage of stool.

U.S. Pat. No. 6,013,023 to Klingenstein ("Klingenstein") generally describes a device to control fecal incontinence. Klingenstein includes an embodiment with stabilizing features disposed external to the vagina, which can be uncomfortable and cumbersome for patients. Klingenstein also describes an embodiment without external stabilizing features. This design, however, is not adapted for stability in the vagina in the expanded and unexpanded states of the device. This is problematic when trying to repeatedly and reliably control the expansion of the expandable component. An additional drawback to Klingenstein is that his device is not designed and configured to allow slack in the vaginal tissue to effectively occlude the rectum. Additional deficiencies of the Klingenstein disclosure are set forth herein.

A class of products generally referred to as pessaries have been typically used and indicated for the treatment of pelvic organ prolapse. In this regard pessaries are positioned intra-vaginally to support organs, such as the uterus, from prolapsing into the vaginal canal. There are also a variety of other intra-vaginal devices that have been used for birth control, urinary incontinence, and other conditions. These devices have a variety of shapes. Some have the ability to expand, but no pessaries are indicated for the treatment of FI and the deficiencies of these devices will be set forth below.

A need exists for an effective intra-vaginal device adapted to stably and comfortably occlude the rectum to control stool passage for treating fecal incontinence.

SUMMARY OF THE DISCLOSURE

One aspect of the disclosure is an intravaginal device for the control of passage of stool in an adult human female user, the device comprising an occluding portion; and the device being sized and configured to maintain position and stability through engagement of internal vaginal anatomy during a first state wherein the occluding portion is not extended and a second state wherein the occluding portion extends to at least partially occlude the rectum.

In some embodiments the device is sized and configured to at least partially occlude the user's rectum proximal to the perineal body.

In some embodiments the device comprises a stabilizing portion to which the occluding portion is secured.

In some embodiments the device includes a control element that allows the user to control the extension.

One aspect of the disclosure is an intravaginal device for the control of passage of stool in an adult human female user, the device comprising an occluding portion; and the device being sized and configured to maintain position and stability through engagement of internal vaginal anatomy during a first state wherein the occluding portion is not extended and a second state wherein the occluding portion extends to at least partially occlude the rectum; wherein said device is sized and configured to fit entirely proximal to the inferior pubic ramus.

In some embodiments the device is sized and configured so that the distal portion of the device is disposed in the anterior portion of the vagina adjacent the pubic symphysis when the device is in the first and second states. The device can be configured so that the distal portion of the device fits in the notch formed near the pubic symphysis.

In some embodiments the device is sized and configured to fit between the areas of the ischiopubic ramus and posterior formix.

One aspect of the disclosure is an intravaginal device for the control of passage of stool in an adult human female user, the device comprising an occluding portion; and a stabilizing portion supporting the occluding portion; and the device being sized and configured to maintain position and stability through engagement of internal vaginal anatomy during a first state wherein the occluding portion is not extended and a second state wherein the occluding portion extends to at least partially occlude the rectum; wherein the stabilizing portion is flattened to have a thickness relatively less than the length of the occluding portion.

In some embodiments the stabilizing portions flattens in the proximity of the occluding portion.

In some embodiments the occluding portion extends from the stabilizing body at an angle between about 45 degrees and about 135 degrees from the stabilizing body.

In some embodiments the stabilizing portion has a generally rounded proximal end.

In some embodiments the ratio of the thickness of the stabilizing portion to the extension length of the occluding portion is less than about ⅔.

In some embodiments the thickness of the stabilizing portion is less than about 2.5 cm.

In some embodiments the thickness of the stabilizing portion is less than about 2.5 cm in the proximity of the occluding portion.

One aspect of the disclosure is an intravaginal device for the control of passage of stool in an adult human female user, the device comprising an occluding portion; and the device being sized and configured to maintain position and stability through engagement of internal vaginal anatomy during a first state wherein the occluding portion is not extended and a second state wherein the occluding portion extends to at least partially occlude the rectum; wherein a lateral span of the device is greater than the width of the occluding portion.

One aspect of the disclosure is an intravaginal device for the control of passage of stool in an adult human female user, the device comprising an occluding portion; and the device being sized and configured to maintain position and stability through engagement of internal vaginal anatomy during a first state wherein the occluding portion is not extended and a second state wherein the occluding portion extends to at least partially occlude the rectum; wherein said occluding portion is disposed on a proximal half of the device.

One aspect of the disclosure is an intravaginal device for the control of passage of stool in an adult human female user, the device comprising: an occluding portion; and the device being sized and configured to maintain position and stability through engagement of internal vaginal anatomy during a first state wherein the occluding portion is not extended and a second state wherein the occluding portion extends to press against the rectovaginal septum to at least partially occlude the rectum; and a cushioning portion.

In some embodiments the cushioning portion is located proximally on the device to be in the proximity of the cervix.

In some embodiments the cushioning portion is located opposite the occluding portion.

BRIEF DESCRIPTION OF THE DRAWINGS

FIGS. 1A-1D are perspective, bottom, side, and front views of an exemplary intra-vaginal device.

FIGS. 4A-4E are top views of exemplary stabilizing body sizes.

FIGS. 6A-6D show an exemplary application of force to the expanding member, and FIGS. 6E-6F show the expanding member with a supportive member.

FIGS. 8A-8M show alternative stabilizing body and anterior end shapes.

FIGS. 10A-10B are side views of an exemplary device with a spring in the expandable member.

FIGS. 11A-11B are side views of an exemplary device with a spring in the expandable member.

FIGS. 11C-11D are side views of an exemplary device showing one method of operating the inflation mechanism.

FIGS. 11E-11F show views of an exemplary expandable member with reinforcements.

FIGS. 14A-14G are side views of an exemplary device.

FIGS. 15A-15G are views of an exemplary device.

FIGS. 16A-16E are views of an exemplary device with grips or suction mechanisms.

FIGS. 17A-17B are views of an exemplary device fitting with the cervix.

FIGS. 17C-17E are side views of an exemplary device collapsing and expanding.

FIGS. 18A-18B are perspective views of an adjustable expandable member.

FIGS. 19A-19D are views of an exemplary expandable member being adjustable angularly both in and out of the body.

FIGS. 21A-21D are perspective views and top views of an exemplary device.

FIGS. 23A-23C are views of exemplary latching mechanisms.

FIGS. 24A-24B are views of exemplary attaching mechanisms for maintaining the exemplary inflation mechanism in the vagina.

FIGS. 25A-25B are views of an exemplary inflation mechanism as a tube.

FIGS. 26A-26B are side views of a device with active contraction.

FIGS. 27A-27B are perspective views of a device with irreversible removal.

FIG. 28A is a side view of an external inflation mechanism.

FIGS. 28B-28D are views of a device with a mechanism for directing the inflation mechanism to a valve.

FIG. 29 is a side view of an electromagnetic inflation mechanism.

FIGS. 30A-30B are views of a device with a retractable inflatable mechanism.

FIGS. 31A-31C are views of different shaped expandable members.

FIGS. 31D-31G are views of a device with suction mechanisms.

FIGS. 35A-35C are side views of a device with a single use reservoir.

FIGS. 36A-36C are side views of a device with a single use syringe.

FIGS. 37A-42B illustrate views of an exemplary intra-vaginal device for the control of stool passage.

FIG. 49 illustrates an exemplary device and an exemplary occluding portion.

FIGS. 50 and 51 illustrate a first and second layer that are adapted to move with respect to one another.

FIGS. 52A-C illustrate an exemplary device and its positioning within a vagina.

FIGS. 53A-82D illustrate exemplary intra-vaginal devices and exemplary components thereof.

FIGS. 88A-88B illustrate an exemplary intra-vaginal device for the control of stool passage.

FIGS. 89A-B illustrate an exemplary occluding portion.

FIGS. 90A-C illustrate an exemplary intra-vaginal device for the control of stool passage.

FIGS. 94-96 illustrate an exemplary occlusion control device and its method of use.

FIGS. 105A-B illustrate an exemplary device that includes a pressure gauge.

FIGS. 106A-B illustrate an exemplary tactile indicator.

FIGS. 107A-B illustrate an exemplary device that utilizes magnetic force to occlude the rectum.

FIG. 108 illustrates an exemplary intra-vaginal magnetic device with a handling portion.

FIG. 109 illustrates an exemplary diaphragm-like device.

FIG. 110 illustrates an exemplary way to secure a magnet in place.

FIG. 111A-B illustrate exemplary stabilizing portions.

FIG. 112 illustrates an exemplary stabilizing portion that includes a distal end that extends upwards relative to the proximal end.

DETAILED DESCRIPTION

Figure 2A:
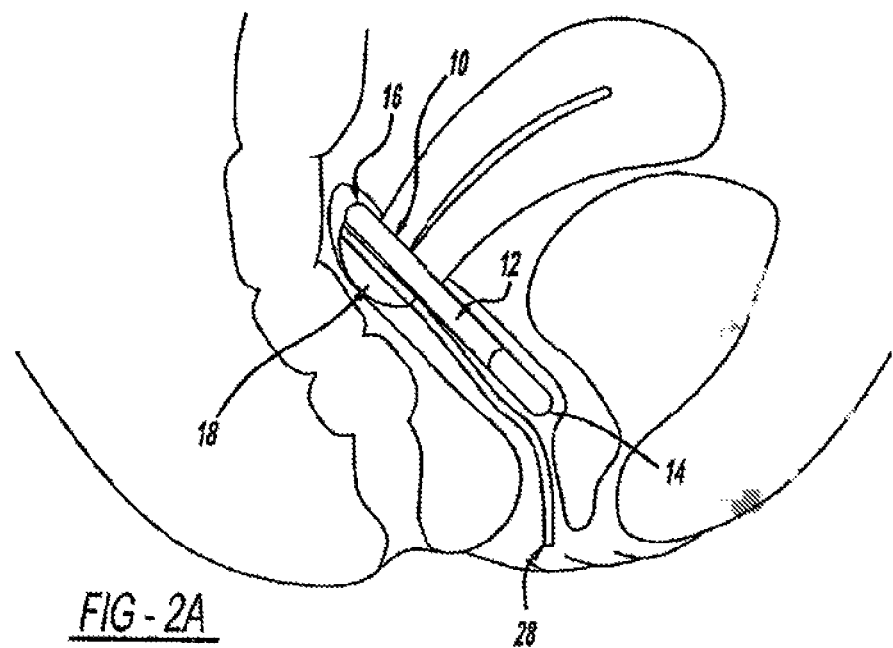
FIGS. 2A-2B are cross-sectional views of the body showing the position of an exemplary intra-vaginal device.

The disclosure herein relates generally to intra-vaginal devices and methods for controlling the passage of stool. The devices are adapted to at least partially occlude the rectum to control the passage of stool while remaining stable inside the vagina.

Extensive cadaver testing and human clinical testing and trials were performed in order to understand key attributes for devices that will achieve the desired vaginal bowel control (VBC). First, the ability to achieve rectal occlusion was found to be influenced by a variety of design features that were unanticipated from knowledge of the anatomy. Second, the stability of the device not only during rectal occlusion but also when the device is not occluding the rectum turned out to be a key aspect of device function and required specific adaptations to ensure the device is stabilized when it is not occluding and when it is occluding. Finally, the devices have to be adapted to interact with the tissue in a way that is comfortable and safe to the user while achieving occlusion and stability. Through bench and human clinical testing, these discoveries of how device design impacted device performance including rectal occlusion, device stability, and user safety and comfort, led to the development of inventive and effective vaginal bowel control devices.

While the disclosure herein focuses on the control of stool passage to treat FI, the devices, systems, and methods of use herein can be used or adapted to be used in one or more other bowel control applications, such as in, for example, the treatment of irritable bowel syndrome ("IBS"), strong urgency to have a bowel movement, diarrhea, loose stools, frequent bowel movements, flatal incontinence, constipation, hard stools, irregular or infrequent bowel movements, abdominal pain or discomfort, cramps, bloating, incomplete stool evacuation, and rectoceles. By compressing the rectum, the device may mitigate the urge to have a bowel movement that comes from a distended rectum, or via some related neurological feedback disruption. In reducing the urge or mechanically blocking stool from passing, it may also increase absorption of liquids from the stool passing through the GI tract, causing less frequent stools and stools that are not as loose in nature. Since these symptoms are often associated with abdominal pain or discomfort, especially in patients with IBS, the devices may help with those symptoms. The devices may also help women become more regular if they are constipated or have hard stools by compressing and decompressing the rectum, thereby applying a regular stimulus that can encourage stool passage. In patients who have a rectocele where stool collects and they may not completely evacuate, the devices can correct the rectocele or deflect it back into a position where stool can exit normally. Additionally, the devices herein can be used or adapted to be used in the treatment of gastrointestinal conditions that may be related to bowel habits or colon and rectum function, for example diverticulitis, hemorrhoids, anal fissures.

One aspect of the disclosure is an intra-vaginal device for the control of rectal volume of an adult human female user, the device comprising a rectal compressing portion and a stabilizing portion, wherein both portions being sized and configured to maintain position and stability while fitting entirely within the vagina and compressing the rectum. Previous attempts have failed to describe or teach an entirely intra-vaginal device designed for stably compressing the rectum.

In this disclosure, the rectal compressing portion may also be referred to as an occluding portion or a force applying portion, and similarly, the act of compressing the rectum may also be referred to as occluding the rectum or applying a force towards the rectum. While most embodiments described herein are described as reversibly occluding, or having occluding and non-occluding states, it is possible for a device in a non-occluding state to still apply some small amount of force on the rectovaginal septum, creating a minor deflection or occlusion of the rectum. However, any such minor forces are inconsequential for the effects on the bowels described herein. A stabilizing body herein could also be referred to as a stabilizing portion. The stabilizing portion and occluding portion are not necessarily different parts, but rather aspects of the device named here for convenience of description. It is the design and configuration of the devices as a whole (including the configuration of the stabilizing and occluding portions and their relationship to each other) that produces the stability, occlusion, and comfort necessary for function.

One aspect of the disclosure is a rectal compressing portion that is extendable or expandable, allowing it to reversibly compress the rectum. The device is an intravaginal device adapted to maintain position and stability in both extended and non-extended states. One of the drawbacks with previous attempts at stool control is that they fail to teach or describe devices that are intra-vaginally stabilized when an expandable portion is in a non-extended state. One of the advantages of the devices herein is that they are sized and configured to stabilize and maintain the device in a desired orientation when the occluding portion is in a non-occluding state. Additionally, the devices are sized and configured to stabilize and maintain the device in the desired orientation throughout repeated changes between occluding configurations and non-occluding configurations. Additionally, the devices are sized and configured to cause the occluding portion to repeatedly extend against the recto-vaginal septum in a desired extension direction to at least partially occlude the rectum even after the occluding portion has transitioned to a non-occluding state. Additionally, the devices are sized and configured to extend against the same part of the recto-vaginal septum, and as later described, the location on the rectovaginal septum where the portion extends is important. Additionally, the devices are sized and configured to maintain the occluding portion extended against, and in a position where it can be readily extended against, rectovaginal septum in extended and non-extended states, respectively.

It has been discovered through testing that how the device is designed to engage and be positioned within the surrounding anatomy is important for stabilizing the device and occluding the rectum. One aspect of this disclosure is a device configured to fit proximal to the area of the pubic ramus in order to stabilize the device when the occluding portion is extended and non-extended. Vaginal bowel control devices designed and configured to engage the anatomy as described allow for increased stability when the occluding portion is in extended and non-extended states. It is further described below how the device is designed and configured to engage the surrounding internal vaginal anatomy for stabilization in occluding and non-occluding states.

Through the course of experimentation, another important discovery was to compress the rectum proximal to the perineal body. During human clinical testing, it was more difficult to obtain intravaginal rectal occlusion with the same posterior force application in the area of the perineal body than in the area proximal to the perineal body. This result was unanticipated because the rectal canal is narrower in the region of the perineal body. Users also felt greater discomfort when force was applied to the perineal body as compared to proximal to the perineal body. Therefore, one aspect of this disclosure is a device designed and configured to stably and repeatedly compress the rectum proximal to the perineal body. This development, as a result of clinical findings, is different than might be suggested based on other mechanisms in medical devices for bowel control. For example, the Acticon® Neosphincter, which also compresses the anorectal canal to control stool passage, is placed at the level of the perineal body.

It was also discovered through cadaver and human clinical testing that the device's effect on surrounding vaginal tissue affects the ability of the device to occlude the rectum. More specifically, if too much slack or redundancy is taken out of the surrounding vaginal tissue by a device distending the vaginal tissue, it makes it more difficult for the device to occlude the rectum. Furthermore, it was found to be less comfortable for the user if the device compresses the rectum when the slack has been taken out of the vaginal tissue. In addition to discomfort, this places additional strain on the tissue and could lead to pressure ulceration, necrosis, or other adverse events. The discovery of this relationship in the tissue resulted in a variety of design features in the devices herein. One aspect of this disclosure is a device designed and configured to minimize the stretch to the vaginal tissue while maintaining stability and compressing the rectum posteriorly. The balance of configuring a device to be stable in the vagina but also reducing stretch on the surrounding tissue in order to occlude the rectum was an important design development. Previous attempts have not described a vaginal device for stool control that is designed to maintain sufficient slack in the vaginal tissue. Additionally, it was found to be important to reduce the stretch on the surrounding vaginal tissue in proximity to the extendable portion during rectal compression.

A variety of device features were developed in order to minimize the stretch to the vaginal tissue while maintaining stability and compressing the rectum posteriorly. Such features, described in further detail below, include the dimensions of the stabilizing body, dimensions of the occluding portion, and the relationship between the dimensions of the stabilizing body and occluding portion; as well as their positioning, absolute and relative to each other.

One aspect of this disclosure is a device designed and configured with a flattened stabilizing portion in relation to the occluding portion. More specifically, the stabilizing body is flattened in a direction substantially perpendicular to the direction of occluder extension. More specifically, the stabilizing portion has a thickness less than the length of the occluding portion. In this disclosure, a flattened stabilizing portion can also be described as: a portion whose thickness in the direction perpendicular to its lateral span and local longitudinal axis is less than the lateral span; particular range of width, length and thickness ratios describing a reduced thickness; a cross-sectional profile (taking the cross-sectional cut with a plane normal to the longitudinal axis of the device, or a plane normal to the proximal-distal axis of the vagina when the device is in-situ) that is relatively short, compared to its width; or a generally planar shape. The elements of such a profile are important for several reasons that were discovered through clinical testing. A stabilizing portion that is flattened relative to the occluding portion, and more specifically in a direction substantially perpendicular to the direction of extension of the occluding portion, provides enough slack in the vaginal walls in order to allow the extendable portion to better and more comfortably compress the rectum. This is in contrast with work disclosed in the prior art attempts, some of which describes a bulky, tubular base. At the same time, a flattened stabilizing portion with appropriate dimensions was also found to contribute to device stability by resisting rotation and translation from forces generated by rectal occlusion, as described further below. A flattened stabilizing portion relative to a direction of extension of the occluding portion also allows the device to fit in the area between the pubic ramus and the posterior formix. More specifically, it allows the distal end of the device to fit anteriorly in the area of the pubic notch. The positioning that is achieved based on the design contributes to device stability by keeping it snug to the surrounding tissue and better occlusion by helping keep the occluding portion proximal to the perineal body.

Figure 2B:
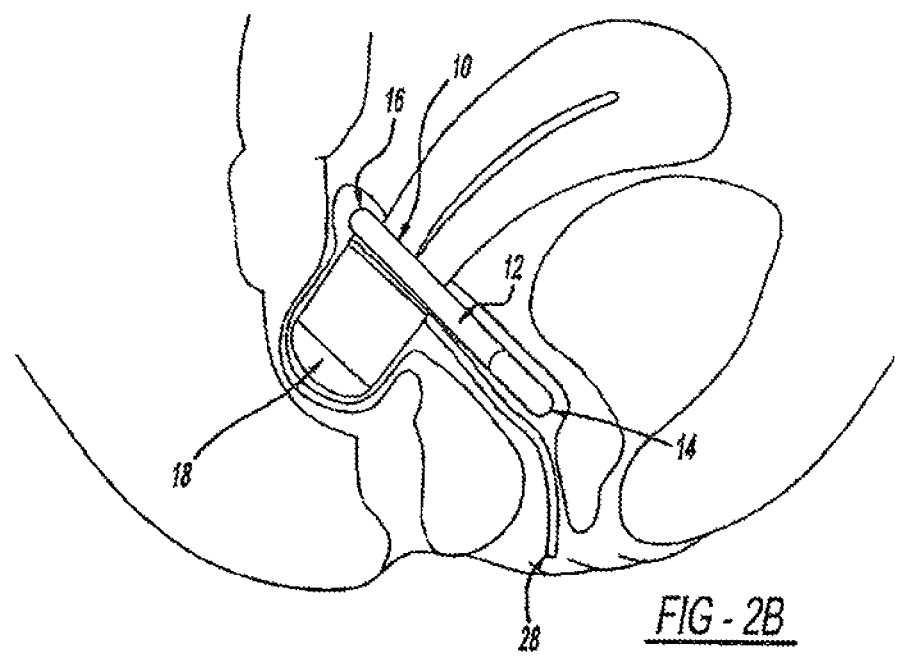

An exemplary intra-vaginal device 10 that is used to control stool passage is shown in FIGS. 1A-1D. The intra-vaginal device 10 includes a stabilizing body 12 for securing the device around the area of the pubic notch and posterior formix and for supporting a force-applying portion 18. The force applying portion 18 can reversibly apply a force to the recto-vaginal septum (the tissue separating the vagina from the rectum) which has the effect of inhibiting the passage of stool through the rectum. This force application can be as shown in FIGS. 2A and 2B, wherein the force application is made via a member expanding against the recto-vaginal septum.

Preferably, the device 10 is designed for the anterior region 14 to fit in the area of the pubic notch. The pubic notch is formed in the anterior vagina, resulting from the structure of the surrounding pelvic floor muscles, providing a stable anchoring point for the anterior end 14 of the device. Preferably, the posterior end 16 of the device 10 fits into the area of the posterior formix. This is the deepest region of the vagina (i.e. the vaginal vault) behind the cervix. In patients without a cervix, e.g. those who have undergone a hysterectomy, the device still rests in the same area, which is the deepest extension of the vagina. A device designed to fit in this region has added security and stability. A more preferable embodiment is designed to fit in both of these areas to provide stability. A device designed for securing in the aforementioned locations will ensure that when placed properly, it rests outside of the region where the vagina is highly innervated, making the device comfortable for the patient. Additionally, the design of the preferred device, by engaging these locations, ensures easy repeatable positioning when the device is inserted, and further ensures positional certainty and stability such that when the device is inserted, it is in the correct position to apply force to the appropriate portion of the recto-vaginal septum, and can do so over multiple inflation/deflation cycles without the need for repositioning.

The force applying portion 18 is preferably an expandable member, and more preferably an inflatable member such as a balloon, though other mechanisms are considered below.

The inhibition of stool resulting from the application of force is due to the force the device applies to the rectum, which disallows the normal expansion of the rectal lumen, which normally occurs to accommodate stool. This action can be described as applying a force to deflect the recto-vaginal septum to compress the rectum, or as generally preventing the expansion of the rectum by applying a force to it. Alternatively, the force applying portion can reversibly apply a force against the vaginal wall opposite of the recto-vaginal septum, which would prevent stool passage by pressing the stabilizing body, or an additional expandable member, against the rectovaginal septum.

The stabilizing body preferably includes a portion proximate to the force applying portion that has a narrow lateral span, such that when inserted, there is minimal distention of, and tension in, the walls of the vagina proximate to the force applying portion.

The stabilizing body 12, preferably has an anterior end 14 and a posterior end 16 operatively connected by a portion 20 or 12, which has a narrow lateral span and includes the force applying member 18, such that when inserted, the anterior end 14 preferably rests around the pubic notch and the posterior end 16 preferably rests in the posterior formix of the vagina, thereby stabilizing and maintaining the position of the intra-vaginal device 10 while minimizing pressure or tension to the lateral walls of the vagina, as shown in FIGS. 2A and 2B. This portion of narrow lateral span can be considered as a central portion of the stabilizing body, or can also be considered as a posterior portion of the stabilizing body.

The preferred embodiment described above minimizes the imparting of tension in the lateral vaginal walls by having a narrow lateral span, especially in proximity to the force applying portion. In a more preferred embodiment, the width narrows from the anterior end 14 to the portion including the force applying portion 18 (FIGS. 1A and 1B), and also considered is a device that narrows from the posterior end 14 to the central portion (Insert FIG. 40A). Alternatively, the anterior end, 14 and the posterior end 16 can be connected by a more generally elongate portion, such as a rod (FIG. 8, item 12), thus avoiding pressure application on the lateral walls.

The width of the expandable portion can be 1-6 cm, more preferably 3-4 cm. The length of the expandable portion can be 1-6 cm, more preferably 2-5 cm. The main body proximate to the expandable portion can be less than 7 cm and more preferably less than 5 cm in width to reduce tension in the vaginal walls.

Figure 7A:
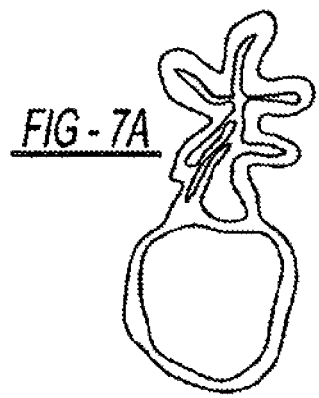
FIGS. 7A-7G show cross-sectional views of the vagina and rectum with the effect of vaginal displacement due to shapes of exemplary intra-vaginal devices.

It is important that the intra-vaginal device 10 not utilize lateral distention of the vagina for fixation when applying pressure to the rectum to occlude stool. FIG. 7A shows a cross-section of the vagina and rectum, wherein the vagina has plenty of slack redundant tissue in folds along the wall.

Figure 7B:
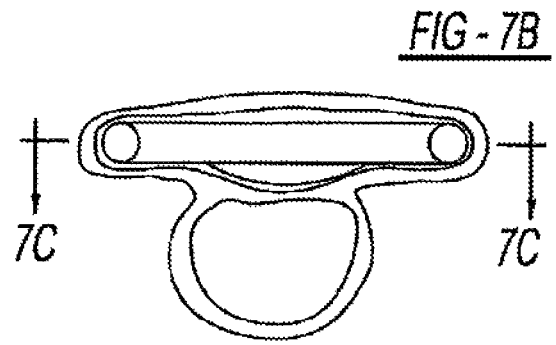
Figure 7C:
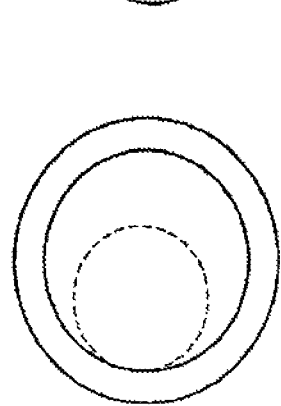
Figure 7D:
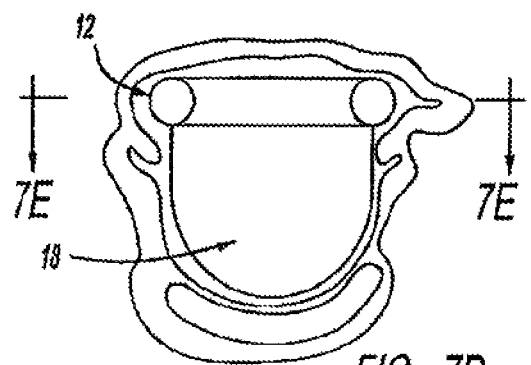
Figure 7E:
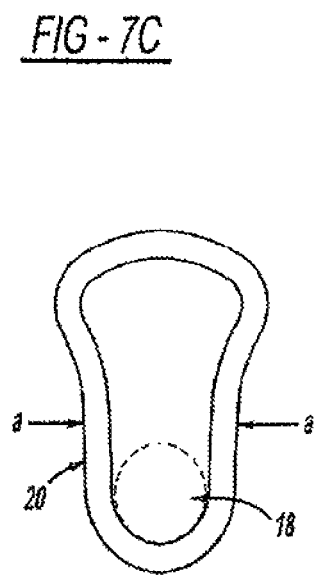

FIGS. 7B and 7C show an intra-vaginal device with a wider body that takes out the slack in the vagina walls, making it difficult to utilize the recto-vaginal septum to occlude the rectum. Since the device creates significant lateral distension on the adjacent wall, the wall loses its redundancy and elasticity and is not easily manipulated by the expandable portion. FIGS. 7D-E show the intra-vaginal device 10 of the present disclosure, wherein the device 10 takes advantage of the vaginal redundancy to push on the rectum. In other words, sufficient slack is still present in the vagina once the device 10 has been inserted, allowing the vaginal walls to be manipulated such that the rectum is occluded. This configuration allows stability and comfort while providing the function of occluding the rectum. Therefore, the present disclosure provides for an intra-vaginal device 10 for the control of stool, including a main body 12 having an anterior end 14 and a posterior end 16, wherein the anterior end 14 and posterior end 16 are operatively interconnected by a portion or sides 20, which include a force applying member 18, such that the aforementioned portion or sides produce minimal displacement adjacent to lateral walls of a patient's vaginal wall allowing for occlusion of the rectum by the expandable member 18.

Figure 7F:
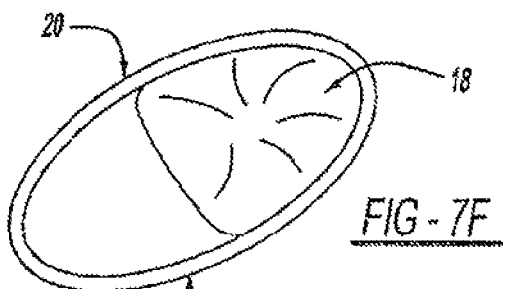
Figure 7G:
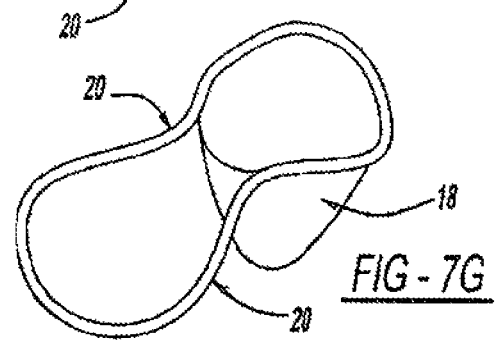

In order to further prevent lateral pressure on the vaginal walls, the sides 20 can laterally narrow when the expandable member is expanded. As shown in FIG. 7E, pressure "a" on the sides 20 when the expandable member expands can cause the sides 20 to narrow laterally. This is also shown in FIGS. 7F and 7G.

The stabilizing body 12 can also include extensions extending perpendicular to an axis formed by a line between the pubic notch and posterior formix, wherein the extensions prevent rotation around the axis. The extensions can extend in a different direction as the direction of the force applying portion 18. The extensions can be perpendicular to the direction of said force applying portion 18. The stabilizing body 12 and the extensions can be a substantially planar structure.

The terms "occluding" or "occlude" as used herein, refer to restricting or obstructing the passage of stool through the rectum. The occlusion can be a full obstruction of the rectum, or it can be a partial obstruction. It is desired to prevent damage to the tissue separating the rectum from the vagina, herein referred to as the "recto-vaginal septum", so the recto-vaginal septum is not overly stretched, but merely held in place against, or displaced towards, the opposite side of the rectum and prevented from expanding in at least one direction to allow the normal passage of stool.

The term "toggling" or "toggle" as used herein, refer to the ability of an object (i.e. the occluding member 108 further described herein) to alternate between two or more positions. The toggling can be accomplished by mechanical or electronic mechanisms further described below.

Figure 3A:
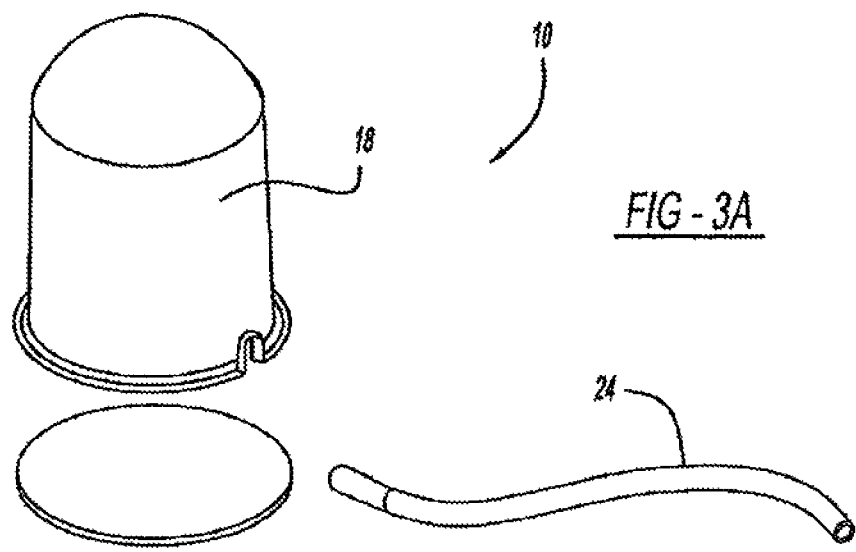
FIG. 3A is an exploded view of an exemplary device and FIG. 3B shows a folded device for insertion.
Figure 31F:
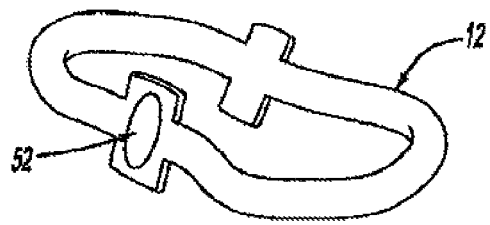
Figure 31G:
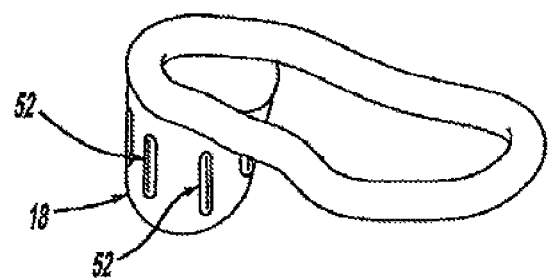

The stabilizing body 12 of the device 10 can be made of wire forms 22 enclosed in tubing 24, as shown in FIG. 3A. The wire forms 22 can be in any suitable configuration, but preferably, there is a wire form 22 for each side of central portion 20. In other words, preferably, the central portion 20 is two sides 20, but a single central portion 20 can be used. Any suitable wire can be used that will provide enough strength to maintain the shape of the device. Alternatively, a polymeric reinforcement can be used in place of, or in conjunction with, the wire forms. The tubing 24 is preferably silicon, but other materials can be used that are biocompatible. The surface of the stabilizing body 12 can include grips 52 on its surface in order to stabilize the device against tissue that it contacts. The grips 52 are small enough and shaped so that the tissue is not damaged or irritated by use. The grips 52 can also be a suction mechanism such as pocks that hold the stabilizing body 12 in place with a vacuum, as shown in FIGS. 31D, 31F. The stabilizing body 12 can also be inflatable, in order to help with insertion and removal.

In a preferred embodiment, the stabilizing body 12 is generally narrow, with the posterior end 16 being approximately of the same width as the force applying portion 18 and in a rounded shape, and the anterior end 14 being slightly wider and in a squared shape in order to fit securely around the pubic notch, and further so as not to unduly take out the slack in the vagina walls. The widened anterior end 14 can be a surface that is curved to approximate the curvature of the pelvic floor muscles interfacing therewith, shown in FIGS. 8K-8M. The roundness of the posterior end 16 also eases insertion and prevents irritation to the vaginal walls. The squareness (i.e. larger flat section before curving into the corners) of the anterior end 14 further helps in preventing the device 10 from rotating within the body. The lateral span of the portion 20 proximate to the force applying portion 18 can be slightly wider than a width of the force applying portion 18.

Figure 3B:
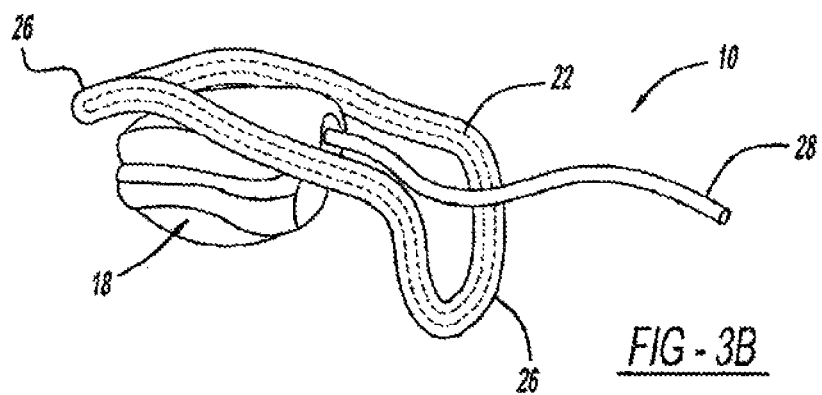

The anterior end 14 and the posterior end 16 preferably include springs 26, or other members that are at least in part flexible, that join the wire forms 22 in the stabilizing body 12 together. The springs 26 and the wire forms 22 can be operatively connected by any mechanism known in the art, including silicone, which can be overmolded over the wireforms. The springs 26 allow the device 10 to be folded along its length for easier insertion and return the device 10 to its open configuration once inside the vagina and in the preferred position around the pubic notch and in the posterior formix. The springs 26 allow the device 10 to conform more naturally to the contours of the vagina. The springs 26 can also or alternatively be located between the anterior end 14 and posterior end 16 along the stabilizing body 12 such that the ends 14, 16 are decoupled from each other (as shown in FIGS. 20A-20G). The springs 26 further prevent force being imparted on one end 14, 16 from being directly transmitted to the other end 14, 16. For example, body forces due to the abdominal contents above the vagina, or forces due to a force applying portion 18 will have less of an effect on the stability of the anterior end 14 if they are connected by a flexible component. The wire forms 22 provide stiffness in the longitudinal direction. The folded configuration is shown in FIG. 3B. Alternatively, the stabilizing body 12 can also be made out of memory materials, alloys, or a contiguous flexible polymer that can return to an open shape after being folded for insertion.

The device 10 can be manufactured according to methods known in the art. For example, silicon adhesive or heat bonding can be used in assembly, or the device 10 can be injection molded as one single piece. The stabilizing body 12 can be glued together or heat melded, and the force applying portion 18 can be injection molded.

The stabilizing body 12 can also be manufactured in various sizes and shapes as shown in FIGS. 4A-4D. The central portion 20 of the device 10 can easily be shortened or lengthened to provide different sizes. The anatomy of every woman is different, and having various sizes and shapes available of the device 10 can allow for many different women to use the device 10. A suitable device 10 can be determined by a trial and error method of insertion. Alternatively, a CAT scan can be performed or X-rays taken, or other medical imaging technologies (ultrasound, MRI) to measure the dimensions of the vagina and rectum, in order to choose a preexisting device 10 or to custom manufacture the device 10 for a particular body.

Additionally, specific tools such as a highly adjustable device or device proxy can be used to determine the correct size and shape for a given patient.

Figure 5A:
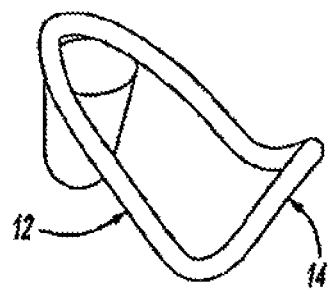
FIGS. 5A-5I are views of exemplary stabilizing body profiles.
Figure 5B:
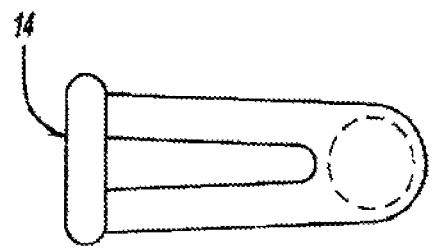
Figure 5C:
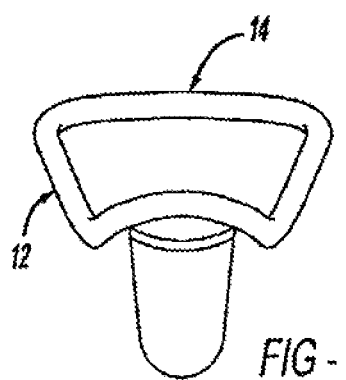
Figure 5D:
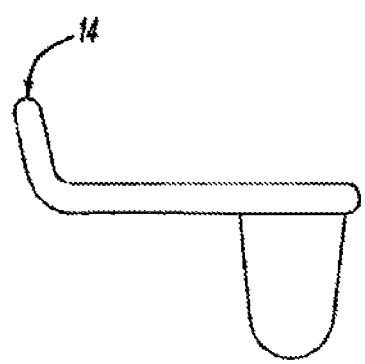
Figure 5F:
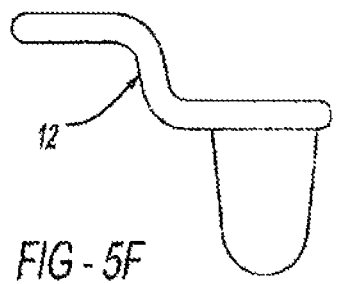
Figure 5G:
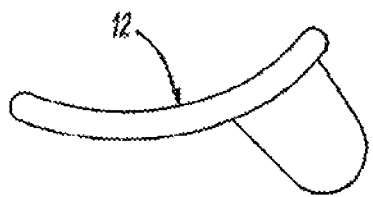
Figure 5I:
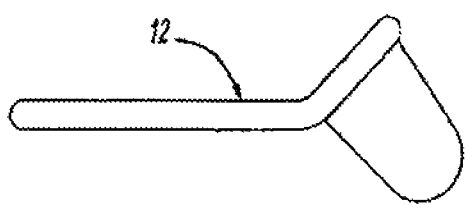
Figure 5E:
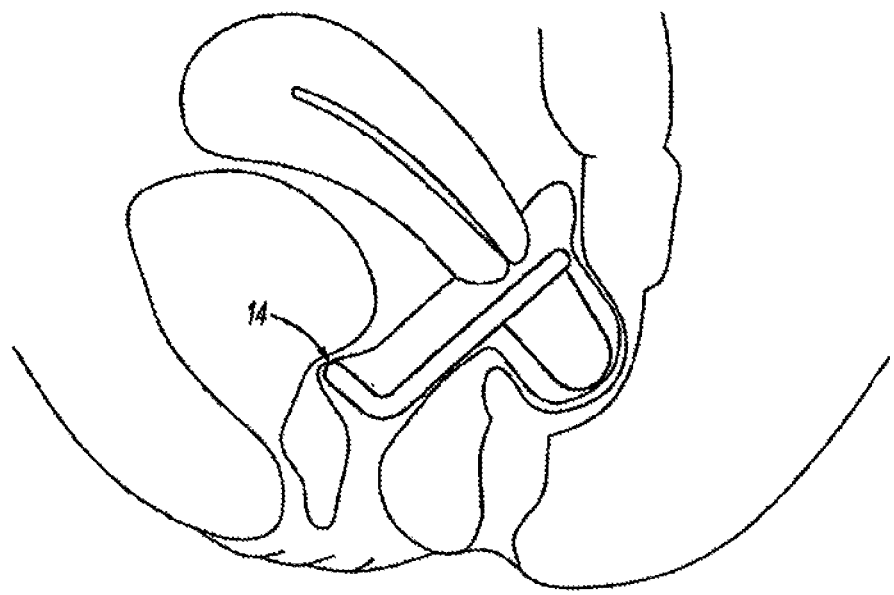
Figure 5H:
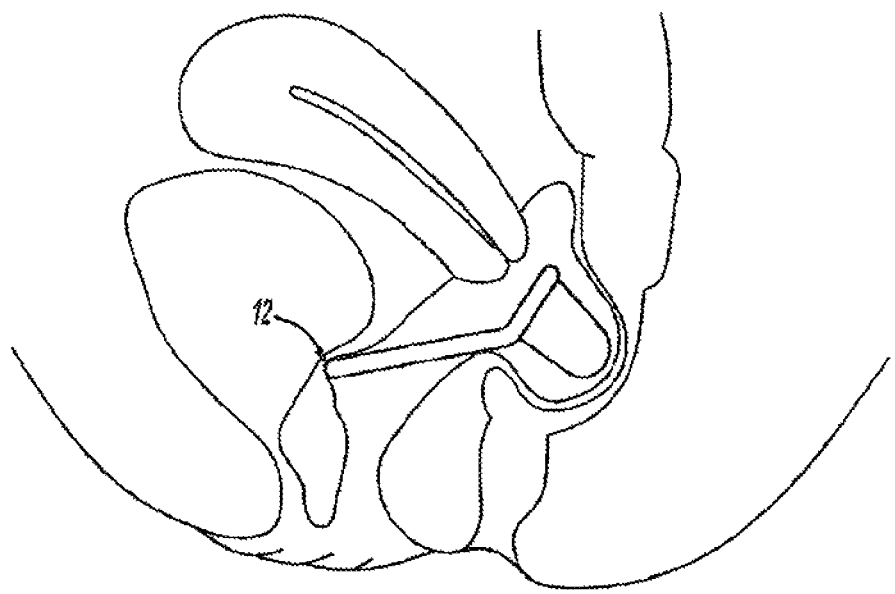
Figure 34A:
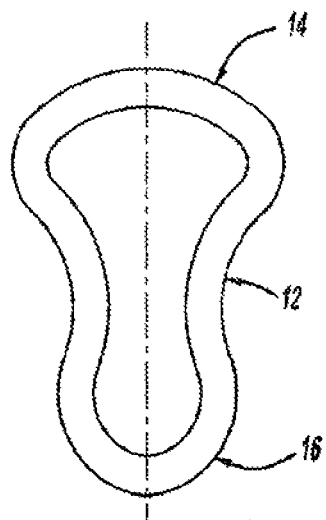
FIGS. 34A-34B show the line formed between the anterior and posterior ends.
Figure 34B:

The stabilizing body 12 can also be not completely straight when viewed from a sagittal plane, but include an upward angled or curved anterior end 14 (FIGS. 5A-E), a stepped stabilizing body 12 (FIG. 5F), a bowed stabilizing body 12 (FIG. 5G), or an upward angled central portion of the stabilizing body 12 (FIG. 5H-I). In other words, the stabilizing body 12 can include a portion that raises above the line formed by the anterior end 14 and the posterior end 16 (this line is shown in FIG. 34A-34B). These different shapes of the stabilizing body 12 can aid in stability of the device 10 in different anatomies.

The force applying portion 18, preferably in the form of an expandable member 18 and referred to as such herein interchangeably, at the posterior end 16 can be actuated between an expanded state and a contracted state in order to either prevent stool from passing through the rectum by pressing against the recto-vaginal septum and preventing the rectum from expanding to allow passage of stool (expanded state) or to allow stool to pass through the rectum (contracted state). The expandable member 18 is also preferably in the contracted state upon insertion, and can fold into the stabilizing body 12 and into itself for ease of insertion. However, the device 10 can also be inserted with the expandable member 18 at least partially expanded, and merely providing means for contracting the expandable member 18 (or allowing it to be compressed) to allow the passage of stool.

The expandable member 18 can be in various shapes and can include a domed portion that contacts the recto-vaginal septum. The expandable member 18 can be wider at a terminal end 33 opposite to where it attaches to the stabilizing body 12 (FIG. 31A), or can be narrow at its terminal end 33 (FIG. 31B). The expandable member 18 can be curved (FIG. 31C).

The expandable member 18 can be in the form of a balloon type portion. The balloon can have a permeability to allow for deflation over a pre-determined range of time. Other forms of the expandable member 18 can also be used. A surface of the expandable member 18 that contacts the vagina wall can include grips 52 for stabilization. The grips 52 are small enough and shaped so that they do not irritate or damage the tissue, and they can also be in the form of suctions as described above.

Figure 18A:
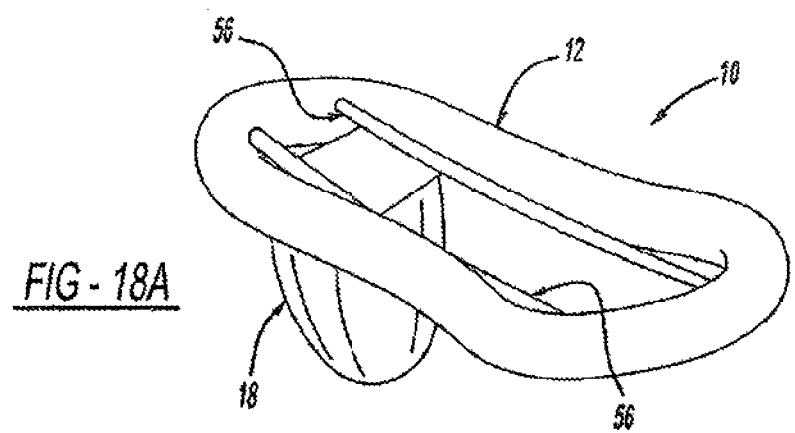
Figure 19B:
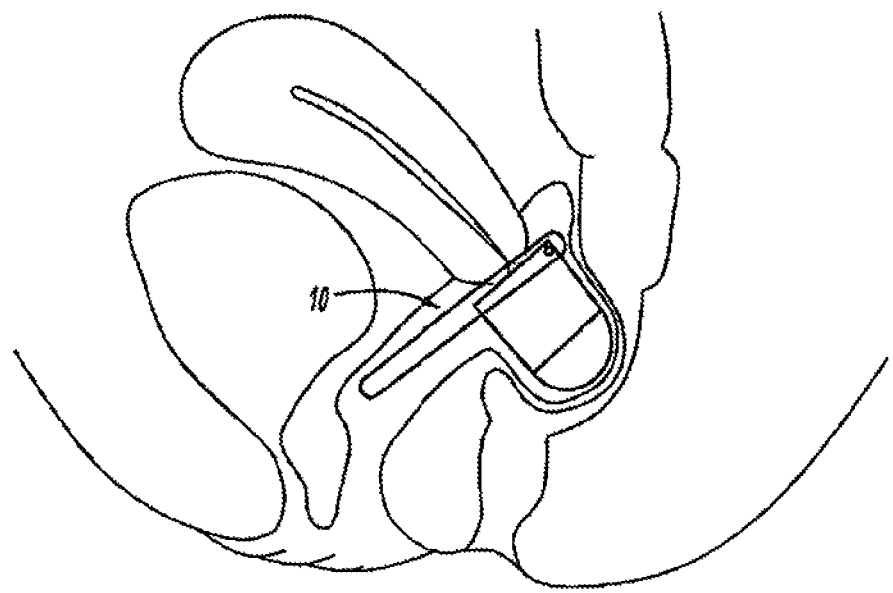
Figure 19D:
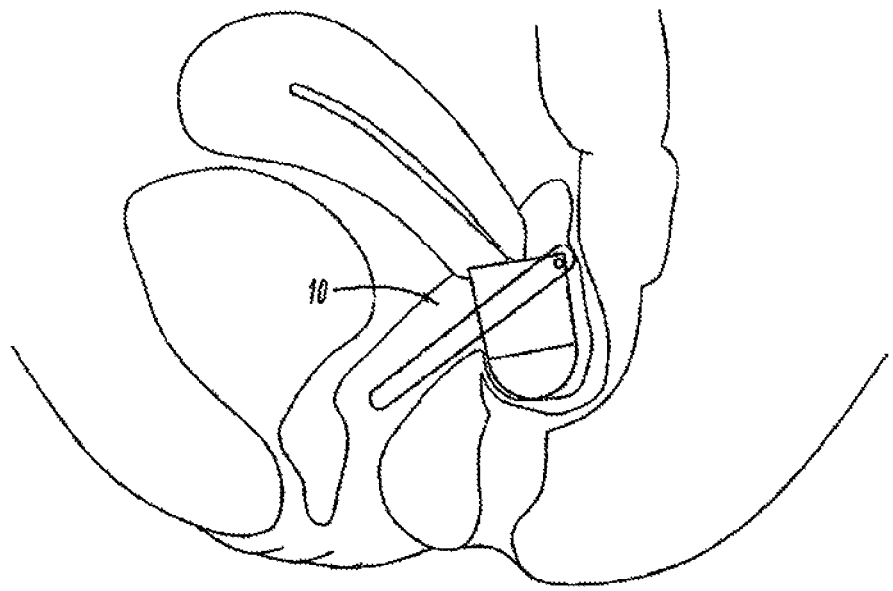
Figure 20A:
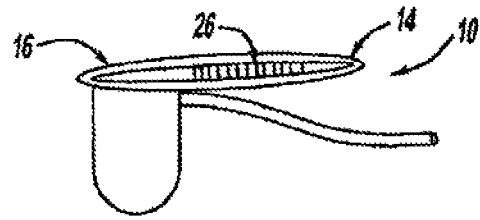
FIGS. 20A-20G are side views of an exemplary device wherein the anterior end and posterior end are decoupled.
Figure 20B:
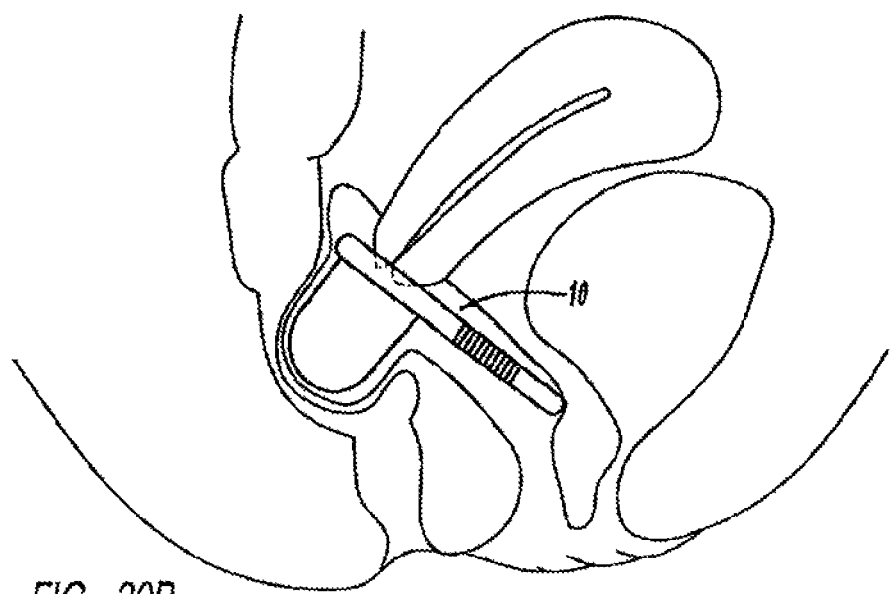
Figure 20C:
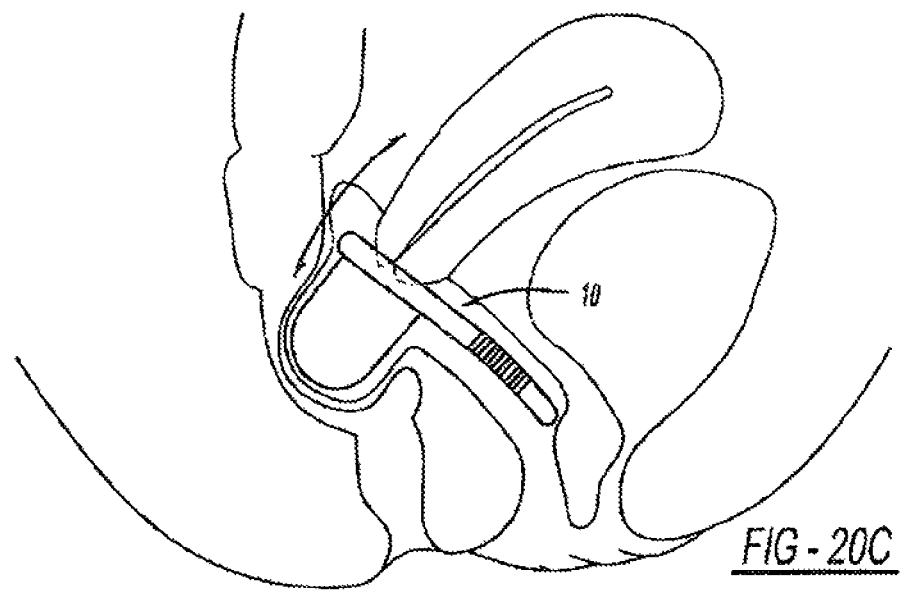
Figure 20D:
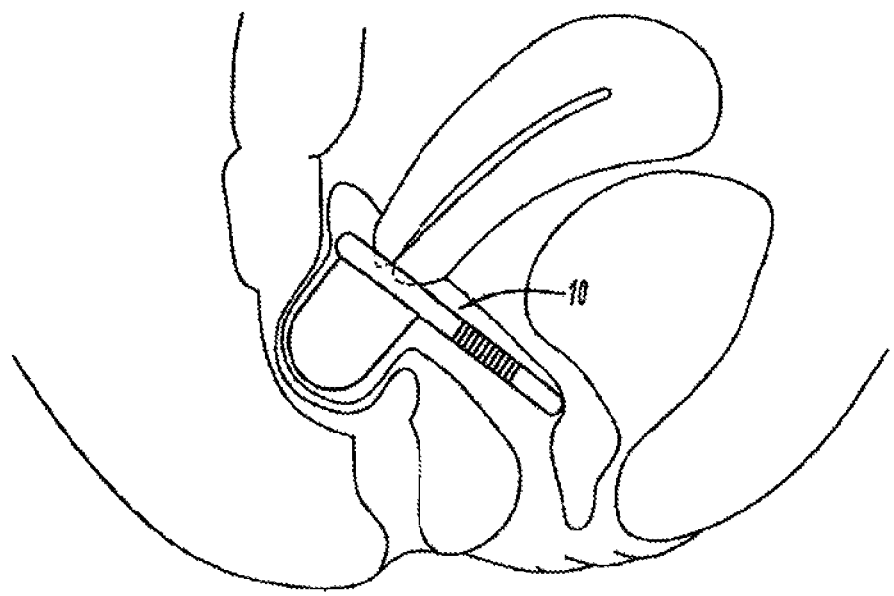
Figure 20E:
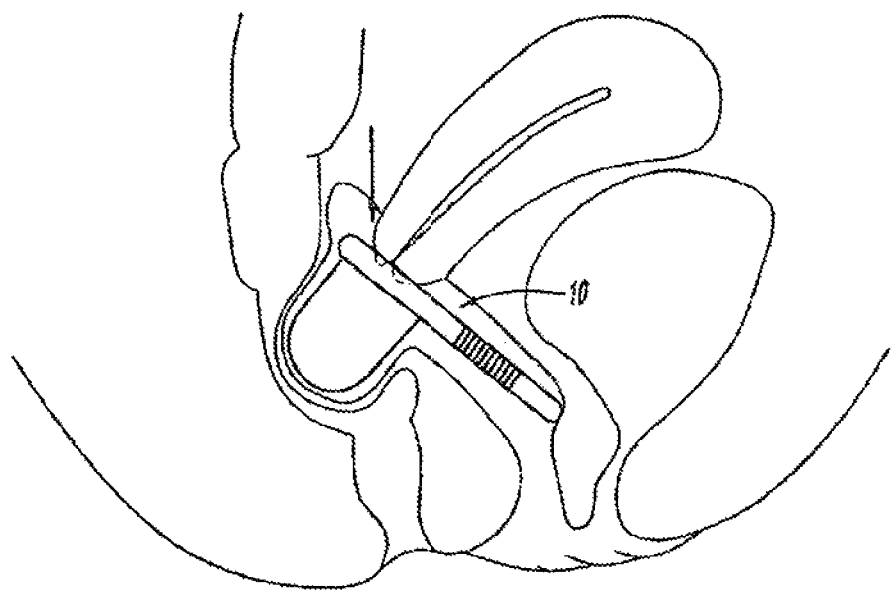
Figure 20F:
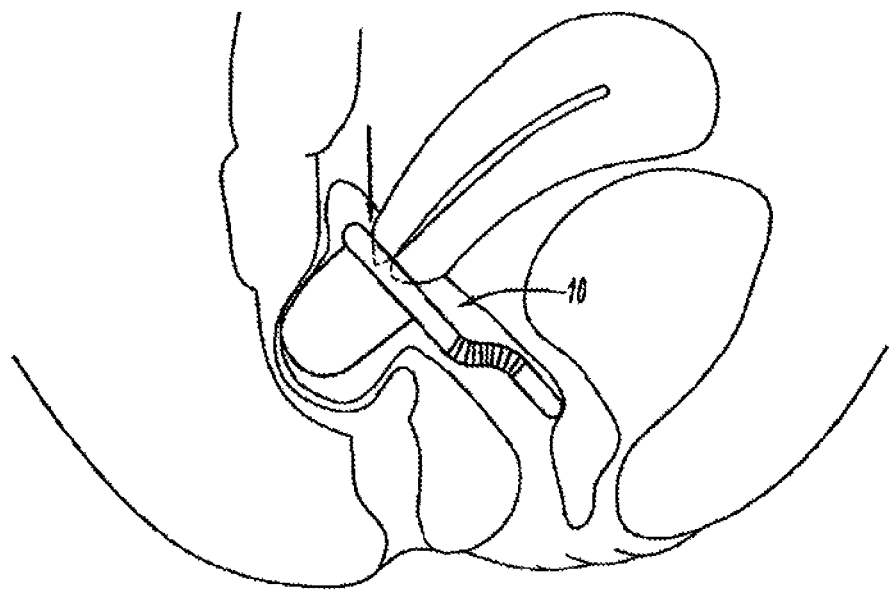
Figure 20G:
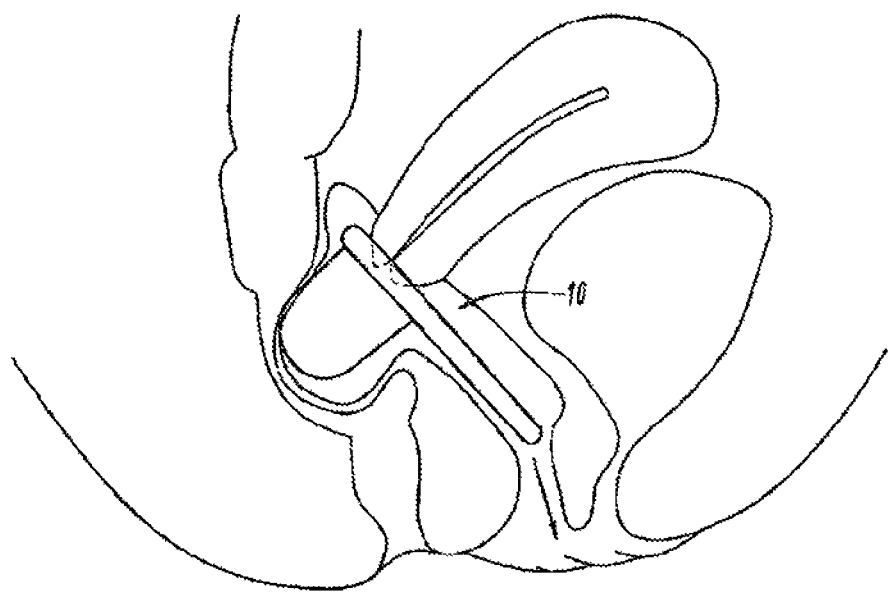
Figure 22A:
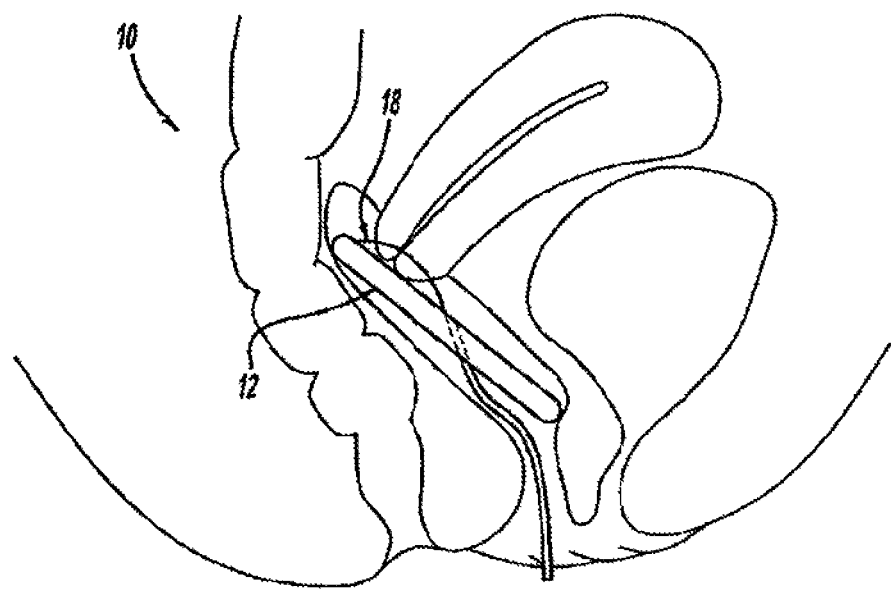
FIGS. 22A-22B are side views of an exemplary device wherein the expandable member expands in an opposite direction.
Figure 22B:
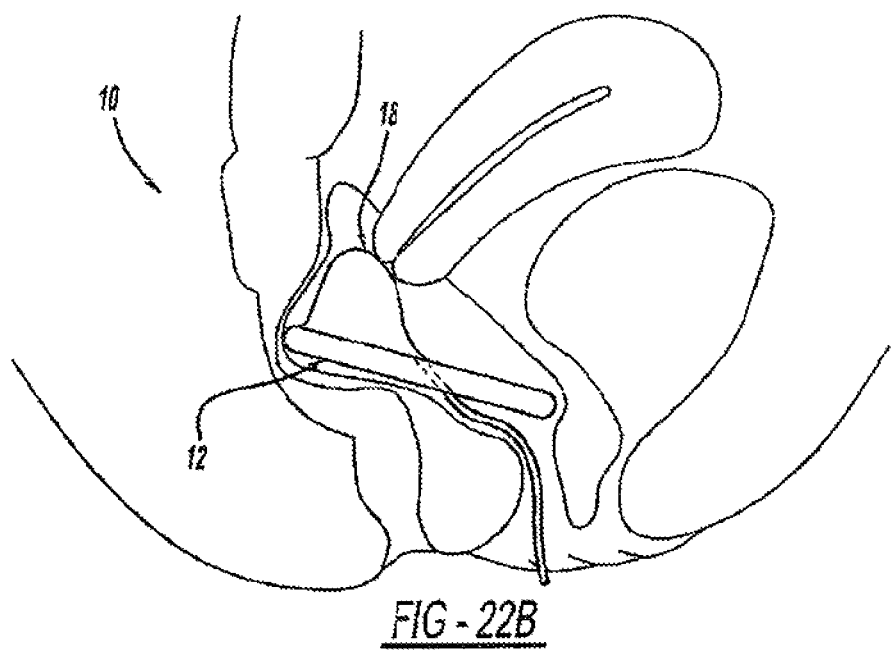

The expandable member 18 can also provide partial, but not total occlusion. It cannot require total or complete occlusion to prevent fecal excretion. Upon occlusion, it is preferred that as much function of the rectum is left as possible, but that the most compliant area of the recto-vaginal septum is engaged and only that area by the expandable member 18. That is, the expandable member 18 should contact the rectum as low as possible to permit as much of the rectum to be functional for fecal storage, and yet it should contact the rectum high enough to provide effective contact to result in the occlusion. This location is preferably above the perineal body, which is bulkier and usually less compliant the recto-vaginal septum. Therefore, in order to provide the best positioning of the device 10, the expandable member 18 can be manufactured at different positions along the posterior end 16 or along various portions of the stabilizing body 12 in order to fit different anatomies. The expandable member 18 can also be manually adjustable along the length of the posterior end 16/stabilizing body 12, which the physician can adjust to fit a patient (FIGS. 18A-18B), with an adjusting mechanism 56. Preferably, the expandable member 18 extends from the stabilizing body 12 at a non-zero angle with respect to a line formed by the anterior end 14 and the posterior end 16. More preferably, the expandable member 18 contacts the rectum wall at a 45-135 degree angle. The expandable member 18 can be angularly adjustable with an angular adjustment mechanism 58 in order to ensure that it is targeting the appropriate part of an individual's anatomy, as shown in FIGS. 19A-19D.

An inflation mechanism 28 is included on the expandable member 18 for expansion and contraction (deflation), which can be reversible or irreversible. The inflation mechanism 28 can be permanently attached to the expandable member 18 and remain in the vagina or extend outside of the vagina (further described below) to expand and contract the expandable member 18. The inflation mechanism 28 and can be in the form of a tube (FIGS. 25A-25B) that creates a leak when pulled that creates irreversible deflation. The tube can also be used with a tool 64 for widening the tube for emptying or filling the tube. Alternatively, the inflation mechanism 28 can be removably attached and can be attached only when the expandable member 18 needs to be expanded or contracted. The inflation mechanism 28 can include a flange at the end attached to the device 10, and located within the device 10, in order to prevent the inflation mechanism 28 from being pulled out of the device 10. The inflation mechanism 28 can be manually operated, such as by pulling on the inflation mechanism 28 to contract or expand the expandable member 18 (shown in FIGS. 11C and 11D), using a hand pump, reservoir, syringe, or it can be electronically operated by a remote control outside of the body. In this case, the expandable member 18 and device 10 include appropriate electronics. The inflation mechanism 28 can be a single use device that is thrown out after use. For example, the single use device can be an air-filled pouch or reservoir 70 that can only be compressed once to fill the device 10, shown in FIGS. 35A-35C, through a one-way valve 68. After inflation, the reservoir 70 is removed and the one-way valve 68 remains. Alternatively, it can be a locking syringe 72 that only compresses once through the one-way valve 68, shown in FIGS. 36A-36C. After inflation, the syringe 72 is removed and the one-way valve 68 remains.

The inflation mechanism 28 can also be an electromagnetic system, shown in FIG. 29, that can be activated externally by a switch that turns on an electromagnet causing the expandable member 18 to expand or contract. For example, one electromagnet can be on the top side 32 of the expandable member 18 and another electromagnet can be located opposite thereto on a bottom side 33, and they can be toggled between attracting each other (contracted state) and repelling each other (expanded state). Appropriate electronics and leads can be included to operate the magnets. The inflation mechanism 28 can also be water, air, a self-curing polymer, or a material that reacts to moisture or heat found in the vagina.

The expandable member 18 can be naturally in an expanded state and must be actively contracted, or alternatively, the expandable member 18 can be naturally in a contracted state and must be actively expanded. Specific examples of the active contraction mechanisms are springs inside the expandable member 18 (further described below), an elastic mechanism attached to the expandable member 18, or an elastic material. Alternatively, the expandable member 18 can include a mechanism for expanding automatically, such as elastics and a one-way valve for allowing air to enter as the expandable member expands. An example of an irreversibly expandable device 10 with active contraction is shown in FIGS. 26A-26B, wherein the inflation mechanism 28 is a zip-tie-like chord that can be pulled, ratcheting the expandable member 18 down.

Figure 9A:
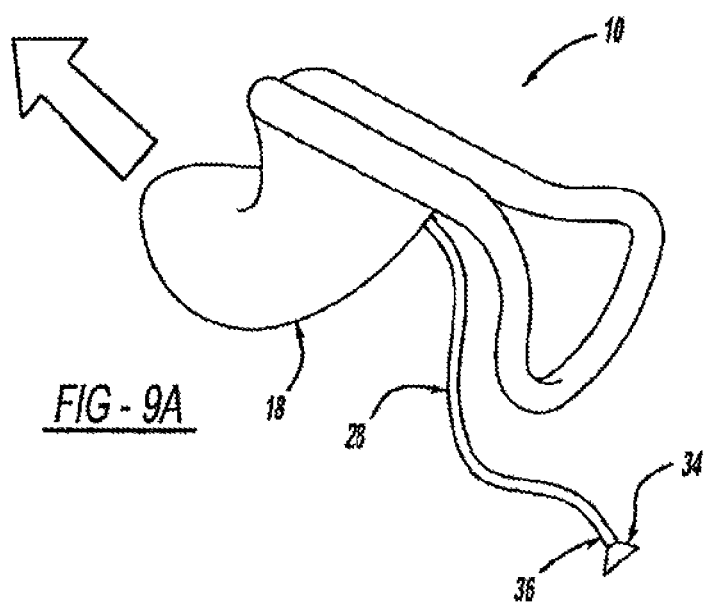
FIGS. 9A-9C show the device including a cap with the inflation mechanism.
Figure 9B:
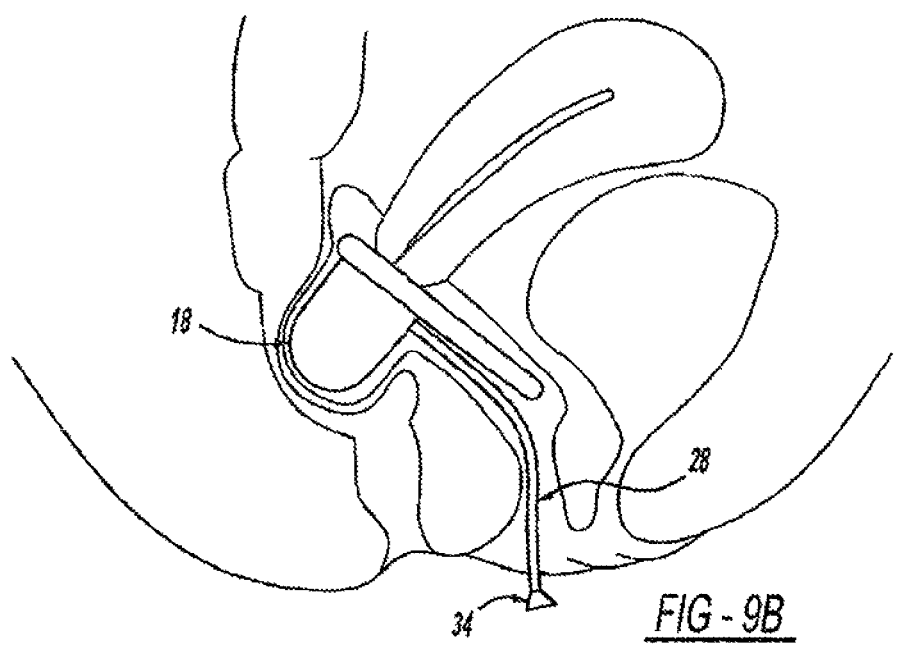
Figure 9C:
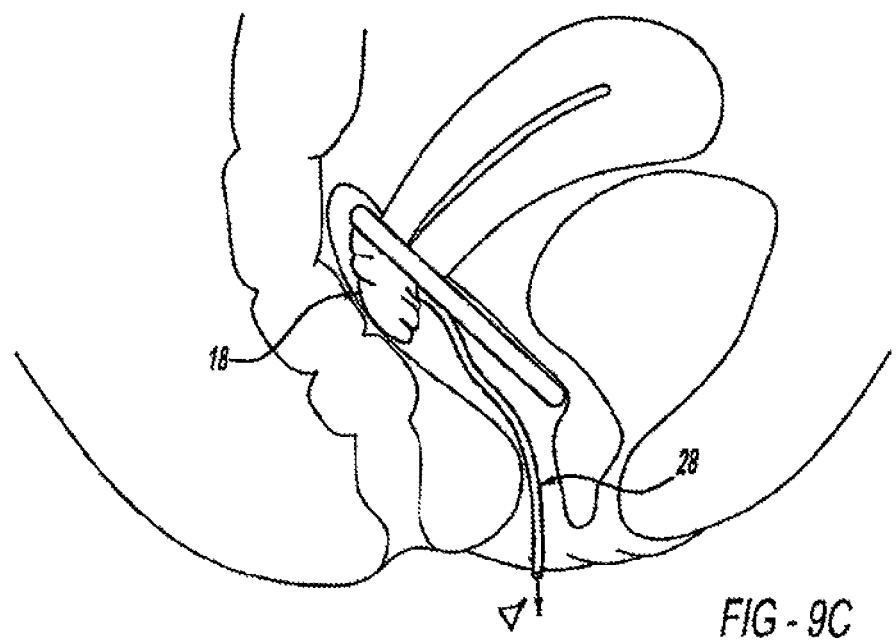
Figure 10A:
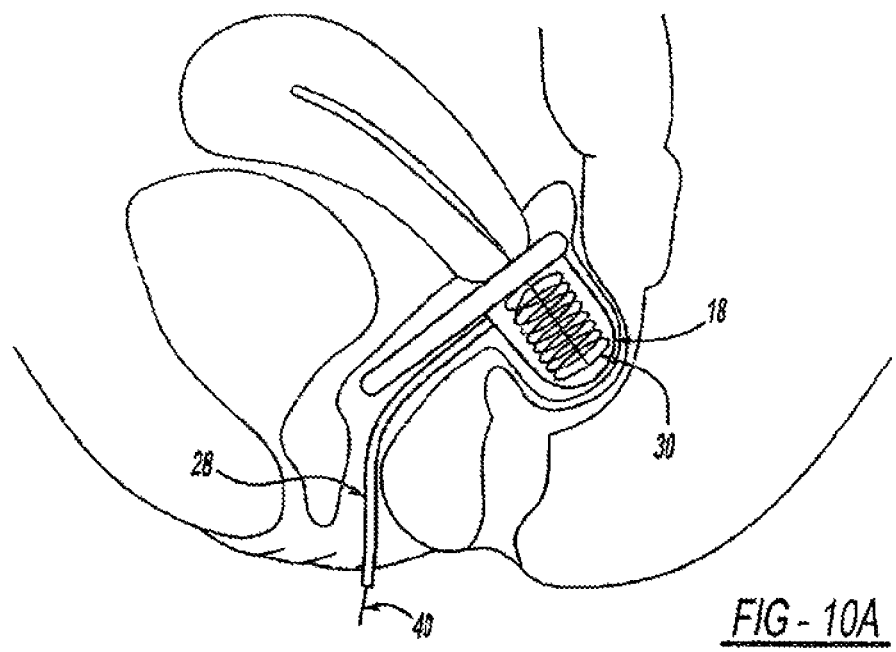

The inflation mechanism 28 can further include a cap or a valve 34 on a distal end 36 that is accessible outside of the body, as shown in FIGS. 9A-9C. By use of the cap 34, the expandable member 18 can be inflated fully or partially prior to insertion of the device 10 in the body. The cap 34 can be removed or actuated to deflate the expandable member 18 and allow stool to pass through the rectum. To enhance deflation, the fluid in the expandable member 18 can be actively expelled by means of a pump. The expandable member 18 can then be expanded again, either by a mechanism as described above, or the expandable member 18 can expand on its own due to the stiffness of the material it is made from.

The expandable member 18 can include a spring 38 that self-expands the expandable member 18, as shown in FIGS. 10A and 10B, and 11A and 11B. In other words, the expandable member 18 can be self-expandable by various means, requiring active deflation or contraction to allow fecal passage. In this embodiment, the user would not have to actively inflate or expand the device during use. Rather, the user would actively deflate or contract the device to allow for fecal elimination.

The inflation mechanism 28 can include a string 40 accessible to the user outside of the body that can be pulled to collapse the spring 38 and allow stool to pass. After the string 40 is released, the spring 38 pushes the expandable member 18 back into an expanded state naturally. In other words, this expandable member 18 is generally in an expanded state and must be actively contracted. The spring 38 can also work with the cap 34 described above instead of the string 40. A tube or a wire can also be used in place of the string 40. The spring 38 can also be controlled by a component separate from the device 10, such as a rod, a threaded member, or a keyed member, that is insertable into the vagina for engagement with the spring 38. Preferably, these mechanisms that extend outside of the vagina are of minimal size so as not to cause discomfort of the user. This can include tubes that are collapsible to a generally flat profile and can be opened with the insertion of an additional component to aid in inflation/deflation (shown in FIGS. 25A-25B).

The inflation mechanism 28 can further include a latching mechanism 60 for holding the inflation mechanism 28 (preferably in the form of a tube) in a retracted position inside the vagina, shown in FIGS. 23A-23C. Users can prefer the comfort of this option as opposed to allowing an inflation mechanism 28 to extend outside the vagina. The latching mechanism 60 can include a first component towards a distal end of the inflation mechanism and a second component on the stabilizing body 12, the expandable member 18, or the inflation mechanism 28 proximate to the stabilizing body 12. The latching mechanism 60 can be a mechanical latch (such as a clip, FIG. 23C), a magnetic latch (FIG. 23B), or a hook and loop latch. The inflation mechanism 28 can be retractable into the stabilizing body 12 or the expandable member 18 when not in use (FIGS. 30A-30B). The latching mechanisms 60 can also be features attached to the inflation mechanism 28 that, based on their size and shape, are retained above the introitus. These features can also facilitate the retrieval of the inflation mechanism 28 when inflation/deflation is required.

The inflation mechanism 28 can further include an attachment mechanism 62 towards a distal end of the inflation mechanism 28 for pulling it or the device 10 downward, or for tucking and maintaining the inflation mechanism 28 inside the vagina. The attachment mechanism 62 can be a flexible or non-flexible ring or loop, as shown in FIGS. 24A-24B.

The inflation mechanism 28 can be external to the vagina and engage the intra-vaginal device 10 to permit the exchange of fluid with the expandable member 18 (FIG. 28A). In this case, the inflation mechanism is preferably a syringe, or pump that interfaces with the intra-vaginal device 10. The inflation mechanism 28 can interface with a valve 68 or system of valves on the stabilizing body 12 or the expandable member 18. The stabilizing body 12 or the expandable member 18 can include a mechanism 66 for directing the inflation mechanism 28 to the valve 68 or system of valves, such as a funnel structure (FIGS. 28C-28D), or a magnetic attraction (FIG. 28B).

The expandable member 18 can further include a supportive member 30, such as a cut silicon sheet or a molded silicon member, in order to prevent the expandable member 18 from tilting due to force from the presence of stool in the rectum. FIGS. 6A-6D show what can happen to the expandable member 18 with force applied thereto, i.e. the expandable member 18 can begin to tilt upwards into the stabilizing body 12, and not completely block the passage of stool. Therefore, a supportive member 30 can be attached between the expandable member 18 and the stabilizing body 12 so that tilting is prevented. The supportive member 30 can cover the entire surface of a top side 32 of the expandable member 18, as in FIG. 6E, or the supportive member 30 can be only a strip covering a portion of the top side 32, as in FIG. 6F. The supportive member 30 can also be integrated directly in the top side 32 of the expandable member 18. The supportive member 30 can also cover a portion or an entire inner space of the stabilizing body 12 (as shown in FIGS. 21A-21D). The supportive member 30 can be made of any suitable material that can withstand the force of the stool on the expandable member 18 and maintain the expandable member 18 in position.

The expandable member 18 can further include reinforcements 42 circumferentially around the surface, such as string, stiffer material than the expandable member 18 itself, or a thicker portion of the same material, as shown in FIG. 11E-11F. The reinforcements 42 can aid in stretching the expandable member 18 in a preferential direction, i.e., at the 45-135 degree angle to the rectum wall. The supportive member 30 can also include reinforcements 42 for preventing deflection such as embedded fibers, plastic, or metal.

The expandable member 18 can also support anatomical features external to the vaginal cavity to prevent their prolapse into the vaginal cavity.

Figure 12A:
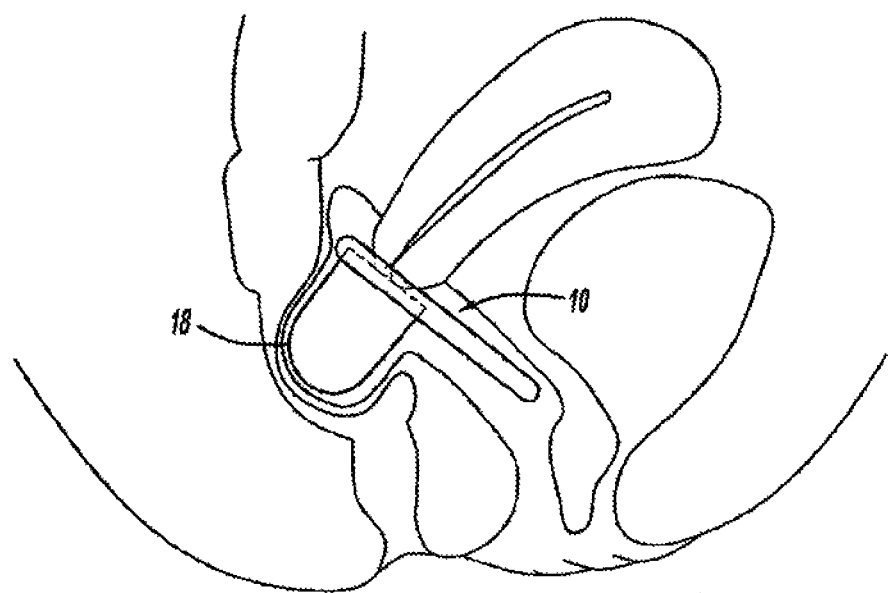
FIGS. 12A-12C show views of an exemplary device to accommodate a larger cervix.
Figure 12B:
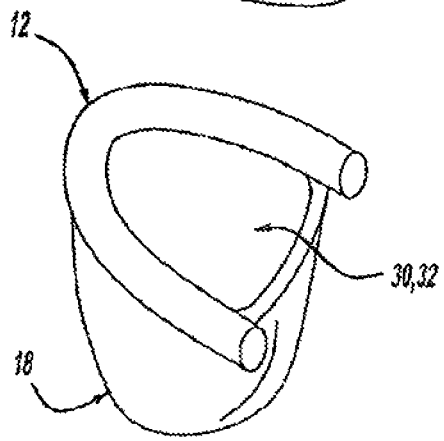
Figure 12C:
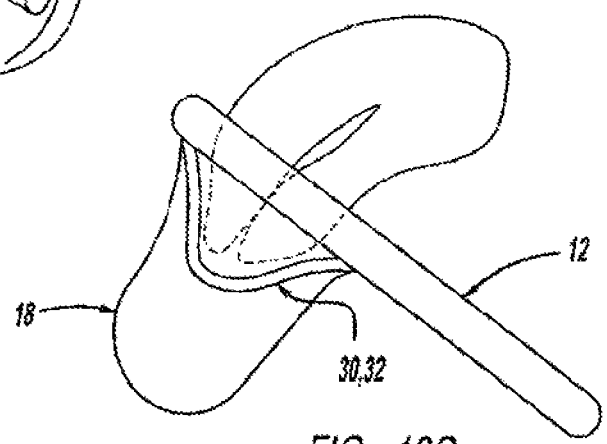

In order to ensure a comfortable fit for users who have a more prominent cervix (FIG. 12A), the top side 32 of the expandable member 18 and/or supportive member 30 can be bowed into the expandable member 18, accomplished by an indentation or a hole, as shown in FIGS. 12B-12C. Any suitable amount of bowing can be used and this aspect can be designed for a particular user by trial and error fitting, or medical imaging analysis of the vagina.

Figure 17D:
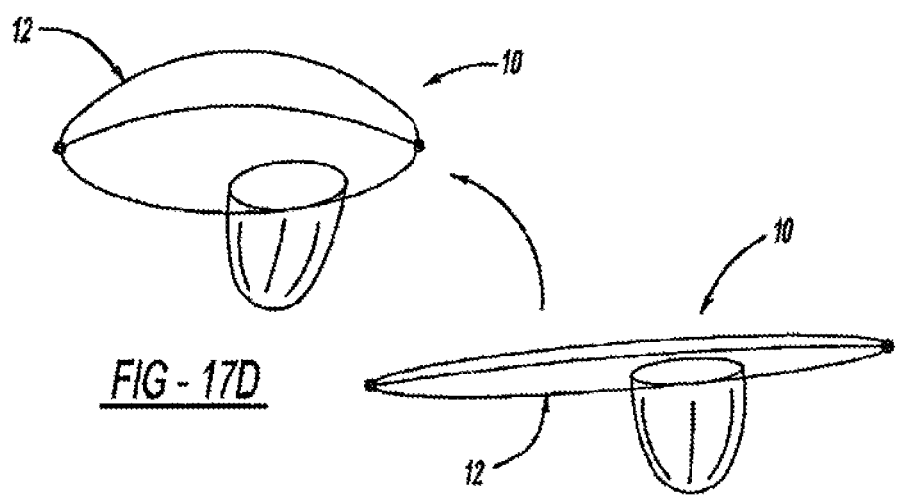
Figure 17E:
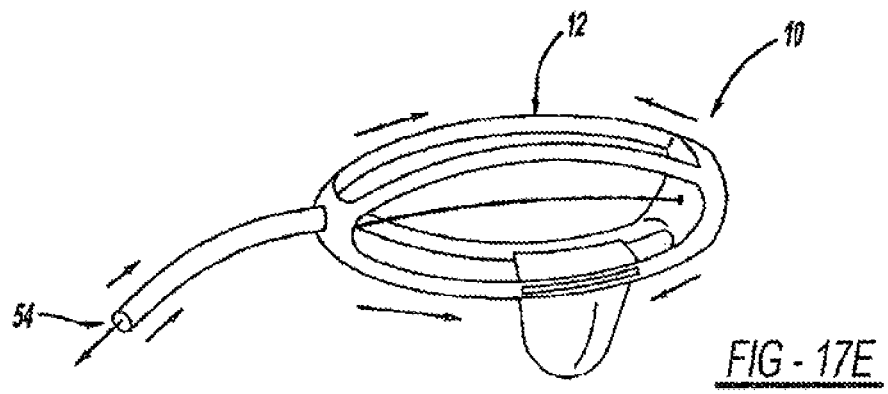

FIGS. 17A and 17B also show the device 10 with multiple sides 20 or rails of the stabilizing body 12 extending from the anterior end 14 to the posterior end 16 that anchor the cervix and also prevent rotation along the length of the device 10. FIG. 17C shows that in this form, the stabilizing body 12 can be collapsed to a smaller profile for insertion, such as by pulling on the ends 14, 16 of the device 10. The spring forces in the sides 20 can also cause the device 10 to spring back to the larger profile (FIG. 17D). The device 10 can also be forced into the larger profile, such as by a member 54 that can be pulled, pulling the ends 14, 16 of the device 10 together (FIG. 17E).

Figure 8A:
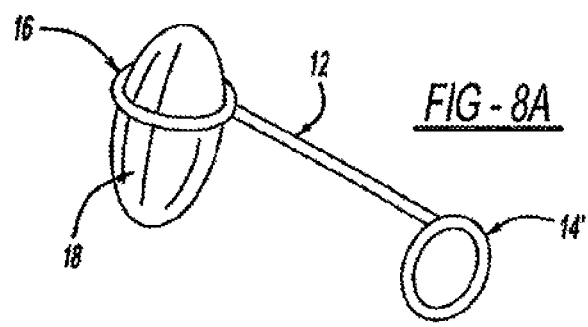
Figure 8B:
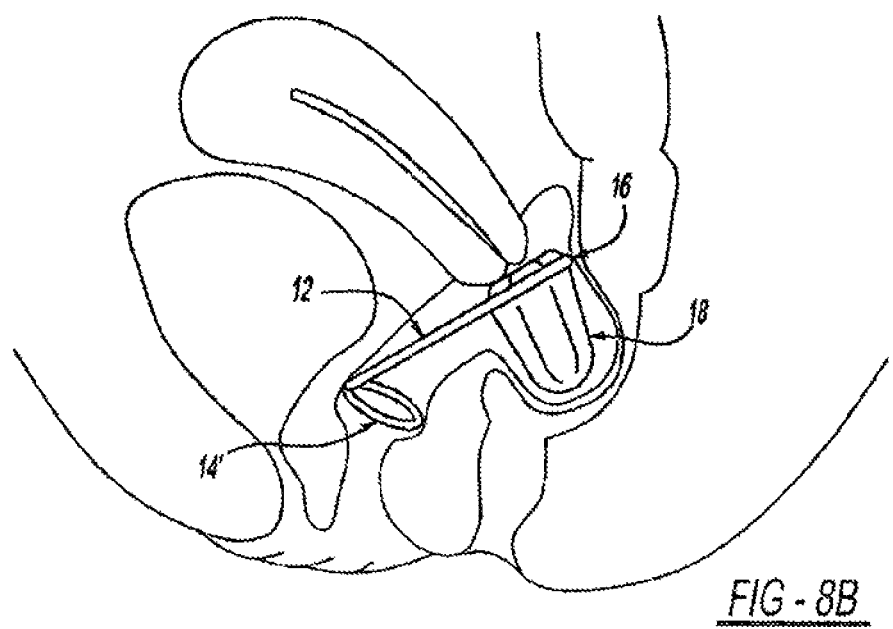
Figure 8C:
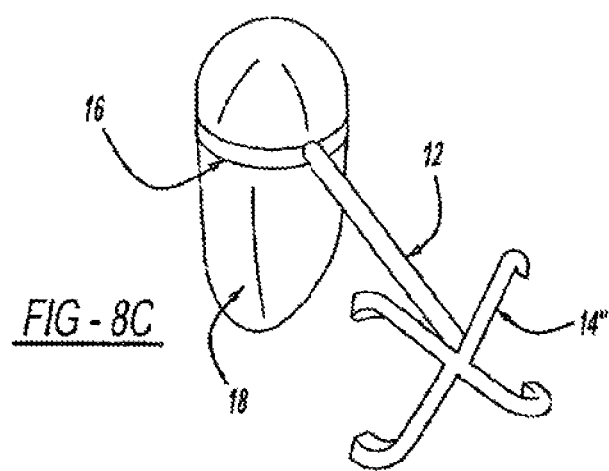
Figure 8D:
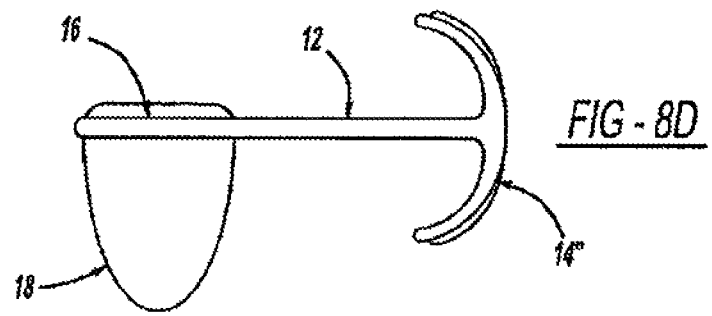
Figure 8E:
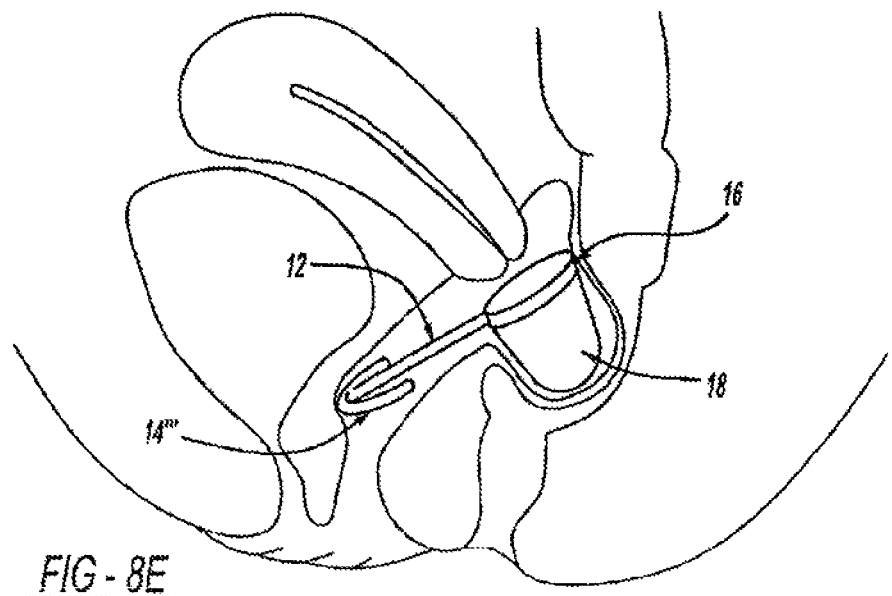
Figure 8F:
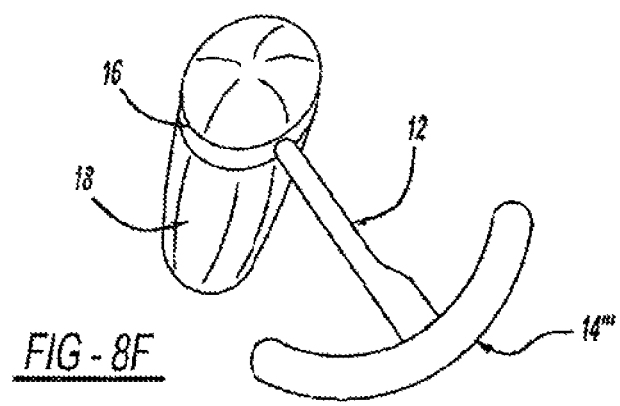

Various aspects of the device 10 can also serve to support other organs around the vagina to help alleviate symptoms of prolapse. The stabilizing body 12 can include an anterior end 14 with other shapes, projections, or space-occupying features in order to keep the device 10 stable in the vagina, but not cause lateral displacement of the vagina walls. For example, the stabilizing body 12 can include a ring-shaped anterior end 14', shown in FIGS. 8A-8B. The stabilizing body 12 does not have two sides of a central portion 20 in this case but rather a single central portion 20 connects the anterior end 14' and the posterior end 16. The anterior end 14'' can also be a cross-shape, or anchor shape as shown in FIGS. 8C-8D. The anterior end 14''' can also be a multi-pronged anchor shape, as shown in FIGS. 8E-8F. The anterior end 14'''' can be a soft or spongy portion, e.g. tampon-like material, that prevents the device 10 from sliding out in FIG. 8G and also expands as it absorbs body fluids such as water. The anterior end 14 can be a disc or diaphragm that is a generally perpendicular planar body to act as a plug to keep the device 10 inside the introitus as shown in FIG. 8H-8I. The disc 14 can be a soft material such as a compliant cushion so that it can deform during insertion, and can also provide suction. Drainage holes 44 can be included as well as a removal mechanism 46, such as a string or soft silicon, which can extend outside of the vagina to facilitate removal. 15. The disc 14 can include an embedded member which can be pulled to reversibly or irreversibly disrupt the mechanical integrity of the disc 14 such that the device 10 is easily removed. The removal mechanism 46 can be included on any embodiment as well, and can be a ring, string, wire, flap, rod, or tube.

The anterior end 14 can be mechanisms to secure the device 10 in the vagina as well as allow for easy removal, such as a spring and tab as shown in FIG. 8J. The tab can be depressed and cause the spring to be contracted, allowing for removal of the device 10. Additionally, the anterior end 14 can be shaped to approximate the curvature of the pelvic floor muscles it interacts with.

Another important aspect of the device 10 is that it has positional stability and rotational stability within the vagina. The positional stability is provided by points of contact of the device 10 with the vagina, most notably the anterior end 14 with the pubic notch and the posterior end 16 with the posterior formix. The expandable member 18 can further provide stability with contact with the wall of the vagina. It is this positional stability that allows the stabilizing body 12 to be designed in different shapes as long as these points of contact remain. Rotational stability is provided as well by the contact of the anterior end 14 with the pubic symphysis and the posterior end 16 with the posterior formix. This rotational stability limits the rotation of device 10 when the expandable member 18 is expanded. Additionally, rotation around the device's anterior-posterior axis is prevented by extensions off of this axis as described above, and more specifically by a generally planar structure. Even more specifically, this rotation is prevented by the additional width of the stabilizing body 12 at either end of the device 10. The expandable member 18 contacts the same part of the vagina wall to occlude the rectum every time that the device 10 is used.

Therefore, the present disclosure provides for a stabilizing mechanism for repeatably contacting the force applying portion 18 with a same area of an anterior rectum wall, the force applying portion 18 being able to inhibit the ability of the rectum to expand to allow stool to pass through. These aspects of the disclosure are critical for assuring maximum comfort and reliability of results for the user.

The stabilizing mechanism can be longitudinal members (i.e. sides 20 and the anterior end 14 and posterior end 16) that form a three-dimensional structure that can change from a smaller profile for insertion to a larger profile for stability. This ability to change the form is described above with the springs 26. The longitudinal members can exert a spring force biasing them towards the larger profile. A mechanical mechanism can be used to secure the longitudinal members in the larger profile, such as a compression mechanism for drawing ends of the longitudinal members close together, i.e., a string, wire, tube, chain, flexible rod, or threaded member.

An additional embodiment utilizes suction forces on a body for stabilization means to allow repeatable positioning and repeatable contact to the recto-vaginal septum (FIGS. 16A-16E). These bodies can be different shapes other than the preferred shape described herein, such as, but not limited to, a cube, wedge, or pyramid, provided they meet the described criteria for stabilization and force application.

In an additional embodiment, the stabilizing mechanism can be secured to a body through surgical attachments to one or more walls of the vagina as described above. The stabilizing mechanism can also include adhesive to secure in the body.

More generally, the device 10 can substantially maintain a single shape that applies force to the rectum. This force can be modulated by changing the position of the device 10 inside the vagina, or by removal and insertion of the device 10.

The present disclosure also provides for an intra-vaginal device 10 including a stabilizing mechanism as described above for stabilizing the device 10 to prevent rotation and translation in the vagina, thereby allowing a portion of the device 10 to reversibly apply force to the same area of the rectovaginal septum to control stool movement through the rectum. The importance of applying pressure on the same area of the rectum has been described above.

The present disclosure provides for a method of controlling stool movement through the rectum, by stabilizing the intra-vaginal device 10 described above and preventing rotation and translation in the vagina, reversibly applying force to the same area of the rectovaginal septum with the device 10, and controlling stool movement through the rectum. The force can be applied with the force applying portion 18 as described above.

The present disclosure also provides for an intra-vaginal device 10, including a stabilizing mechanism for stabilizing the device 10 to prevent rotation and translation in the vagina in a first and second state, wherein when in a first state, force is not applied to the rectovaginal septum (RVS) and, wherein when in a second state, force is applied to the RVS thereby allowing a portion of the device to reversibly apply force to the same area of the rectovaginal septum to control stool movement through the rectum.

The present disclosure provides for a method of controlling stool movement through the rectum, including the steps of stabilizing the intra-vaginal device 10 described above and preventing rotation and translation in the vagina when the device 10 is in a first and second state, wherein when in a first state, force is not applied to the rectovaginal septum (RVS) and, wherein when in a second state, force is applied to the RVS, reversibly applying force to the same area of the rectovaginal septum with the device, and controlling stool movement through the rectum.

Figure 13A:
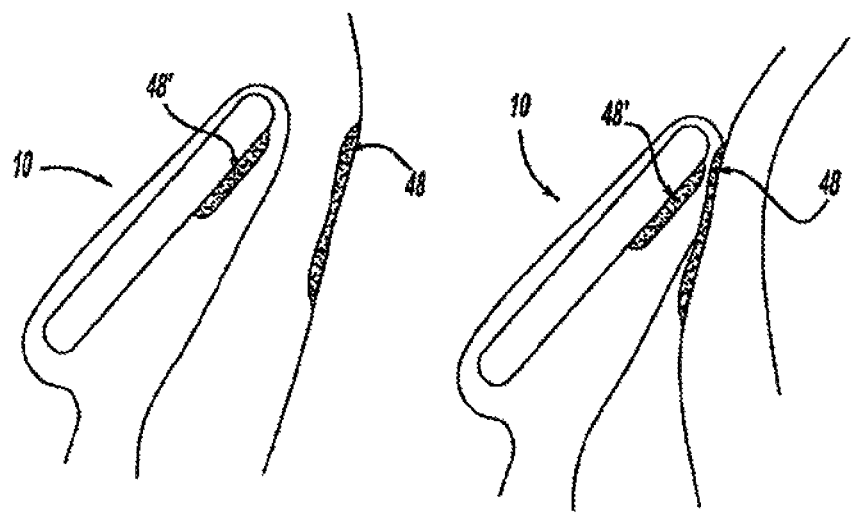
FIGS. 13A and 13B are side views of an exemplary device with additional occlusion mechanisms.
Figure 13B:
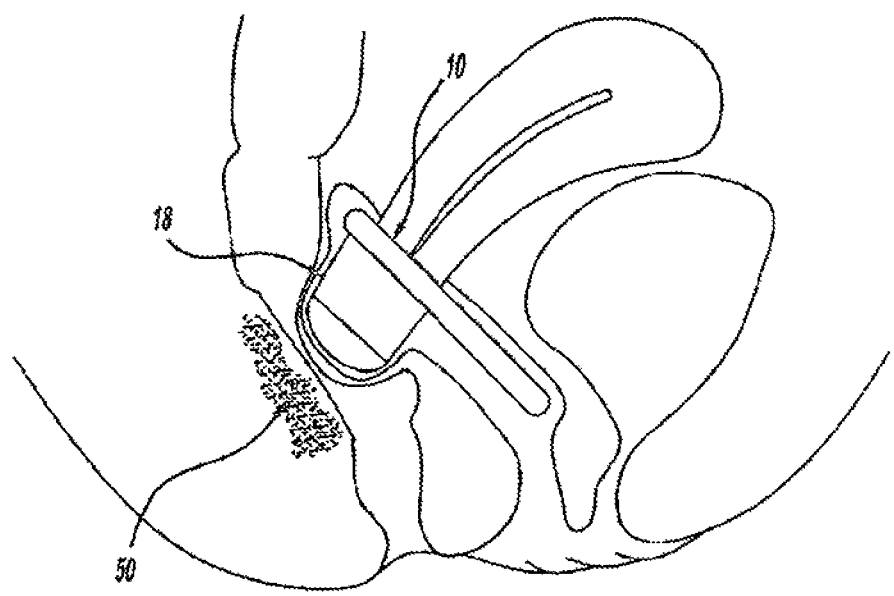

There can be other mechanisms used along with the device 10 in order to achieve rectal occlusion. For example, a magnet 48 can be surgically implanted in the posterior rectal wall in order to interact with a corresponding magnet 48' on the device 10, such as at the bottom of the expanding member 18 as shown in FIG. 13A. The magnets 48, 48' can be electromagnets and can be externally controlled, allowing them to interact with each other to occlude the rectum or to let stool pass. Alternatively, magnet 48' can be simply implanted in the vagina wall opposite the posterior rectum wall without the device 10 to achieve the same results. Also, a mass-occupying agent 50 can be injected into the posterior rectal wall, as shown in FIG. 13B, so that when combined with the device 10, better occlusion of the rectum occurs. Preferably, the mass-occupying agent 50 is directly opposite to the expanding member 18 and interacts therewith. The device 10 can be used with an implanted sling that pulls the rectum anteriorly.

The present disclosure provides for a method of controlling the passage of stool in a patient, including the steps of inserting the intra-vaginal device 10 into the patient's vagina such that the anterior end 14 rests around the pubic notch and the posterior end 16 rests in the posterior formix, exerting a force towards the posterior side of the vagina, preventing expansion of the patient's rectum with the force, impeding the passage of stool, and removing the force, allowing stool to pass. By performing this method, the patient can use the device 10 to prevent stool from passing or allow stool to pass through the rectum. When inserting the device 10, the sides 20 can narrow by the operation of the springs 26 at the anterior end 14 and posterior end 16 for easier insertion. Then the sides 20 return to their normal open position once the device 10 is positioned around the pubic notch and in the posterior formix. Preferably, the force applying portion 18 exerts the force and moves the anterior wall of the rectum. As described above, the force applying portion 18 can be expanded manually or electronically. As the force applying portion 18 expands, because there is slack in the vagina walls, the force of expansion is directed against the rectum, and passage of stool is inhibited. The force can be exerted substantially above the perineal body. The prevention can be an occlusion of the rectum. When it is desired that stool pass through the rectum, the expandable member 18 is contracted (there can be recovery of the expandable member through various mechanisms described above) and the walls of the rectum are allowed to accommodate stool normally.

In an alternative embodiment, device 100 includes a stabilizing body 102 having an anterior end 104 and a posterior end 106, the posterior end 106 operatively connected to an occluding member 108 and including a toggle mechanism 110 for toggling the occluding member 108 between an occlusive and passive state. Essentially, the occluding member 108 can change orientation between a rectally occlusive state, shown in FIG. 14A, to a passive state to allow stool to pass through the rectum, shown in FIG. 14B. The device 100 is generally the same as device 10 described above, except that instead of expanding, the occluding member 108 toggles positions. The device 100 preferably is situated in the vagina such that the anterior end 104 rests around the pubic notch and the posterior end 106 rests in the posterior formix.

Figure 33A:
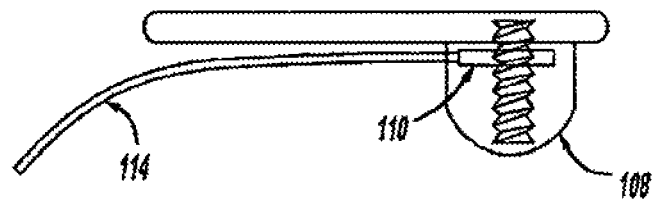
FIGS. 33A-33B are side views of a threaded toggle mechanism.
Figure 33B:
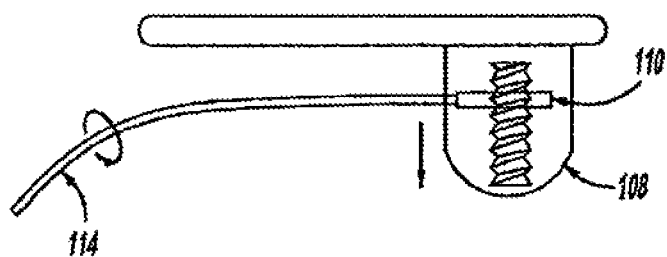
Figure 33C:
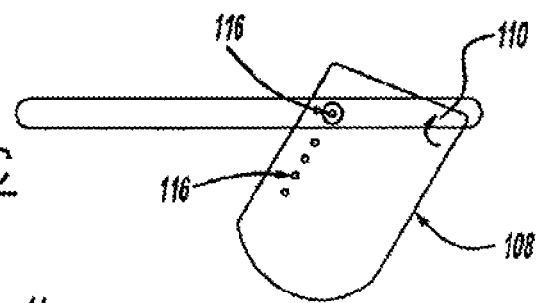
FIG. 33C is a side view of a snap-fit locking mechanism.

The toggle mechanism 110 can be any mechanism known in the art to toggle positions of the occluding member 108. For example, the toggle mechanism 110 can be a hinge or a flexible joint that joins the occluding member 108 to the stabilizing body 102. The toggle mechanism 110 can be a translatable occlusive member such as a slidable occlusive member, or an occlusive member with multiple locked positions such as snap-fit locking mechanisms. (FIG. 33C). The toggle mechanism 110 can also be a threaded member that can be extended or retracted by engaging one or more threads, shown in FIGS. 33A-33B. Preferably, the toggle mechanism 110 includes a method of locking the occluding member 108 when occlusion is desired and so that movement of the occluding member 108 does not occur. A latch mechanism 112 can be used to lock the occluding member 108 in the occluding position as shown in FIGS. 14C-14D anywhere on the occluding member 108 and stabilizing body 102, such as on a side opposite to the toggle mechanism 110. The toggle mechanism 110 can include a control string 114, as shown in FIGS. 14E-14F, or any other control component that extends outside of the vagina such as a wire, tube, lever, or threaded component. The control string 114 can be attached anywhere appropriate on the occluding member 108. Under tension of the control string 114, the occlusive member 108 cannot move and is locked in place in an occluding position. When tension in the control string 114 is released, the occlusive member 108 is free to rotate and moves to a passive position to let stool through the rectum. The occluding member 108 can have an altered or more tapered shape on a side opposite to the toggle mechanism 110 in order to have a more comfortable fit when in the passive position, as shown in FIG. 14G. In an alternate embodiment, the intra-vaginal device can be toggle between and occluding and non-occluding state by removing the device in its entirety from the vagina.

Therefore, the present disclosure provides for a method of controlling the passage of stool in a patient, including the steps of inserting the intra-vaginal device 100 into the patient's vagina such that the anterior end 104 rests around the pubic notch and the posterior end 106 rests in the posterior formix, toggling the occluding member 108 at the posterior end 106 to an occlusive state, preventing expansion of the patient's rectum with the occluding member 108, impeding the passage of stool, and toggling the occluding member 108 to a passive state, allowing stool to pass. This method is generally performed as the method described above, except that instead of expanding the expandable member 18, the occluding member 108 is toggled between an occlusive state to occlude the passage of stool in the rectum and a passive state to allow the passage of stool. The toggling step can further include shifting the occluding member 110 to different snap-fit positions, (FIG. 33C) sliding the occluding member 110 to different position, or engaging threaded components on the occluding member 110 for moving the occluding member 110. The toggling step can be performed by actuating the control string 114 above, or a wire, tube, lever, or threaded component. These components for actuation can be outside of the vagina. The toggling step can also include locking the occluding member 108 with the latch mechanism 112 described above. The preventing step can also include occluding the rectum.

Figure 15D:
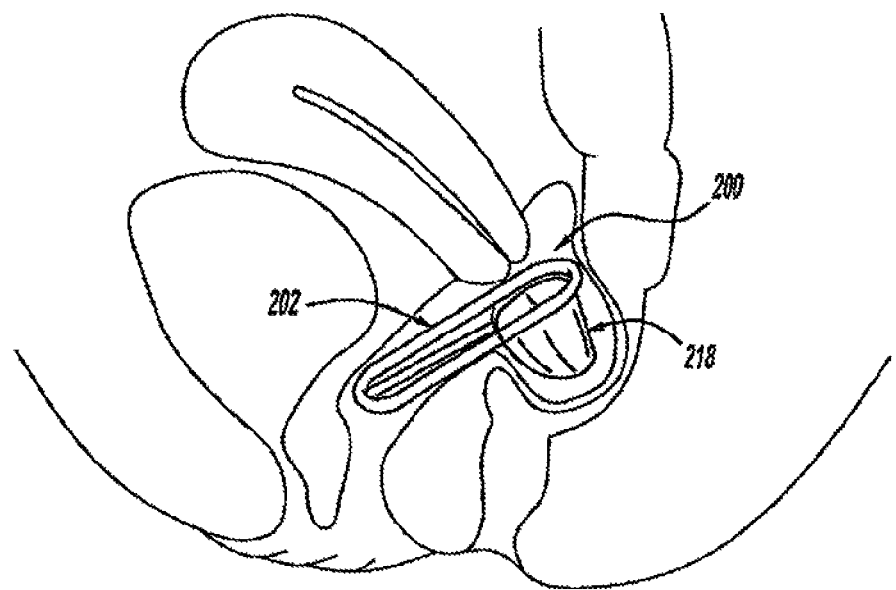
Figure 15E:
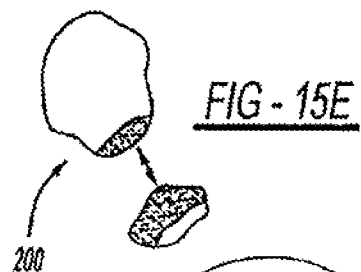
Figure 15F:
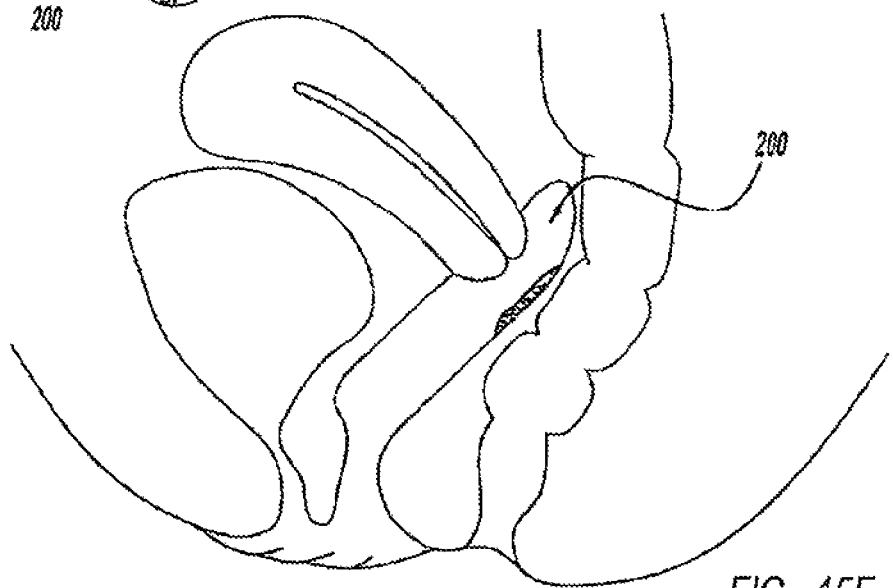
Figure 15G:
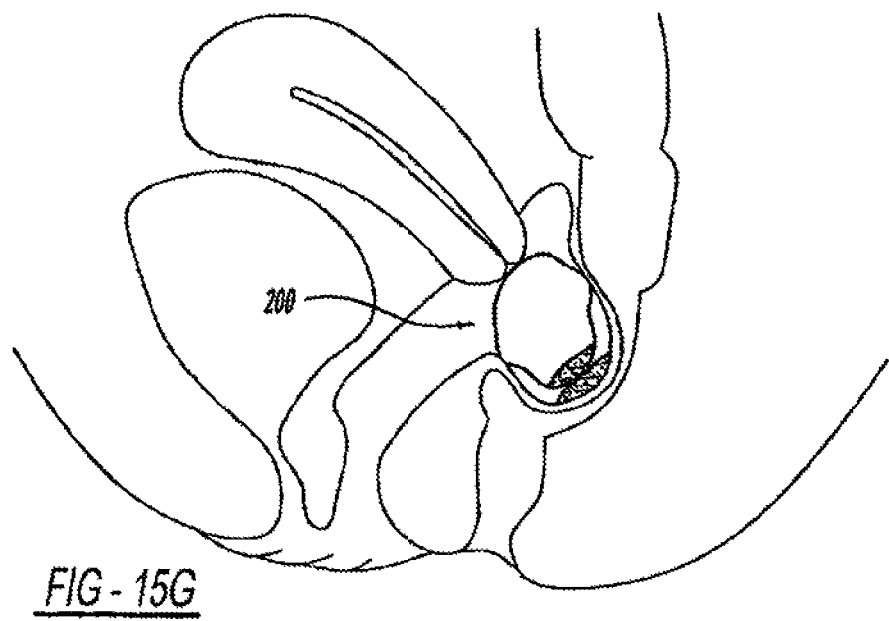
Figure 16A:
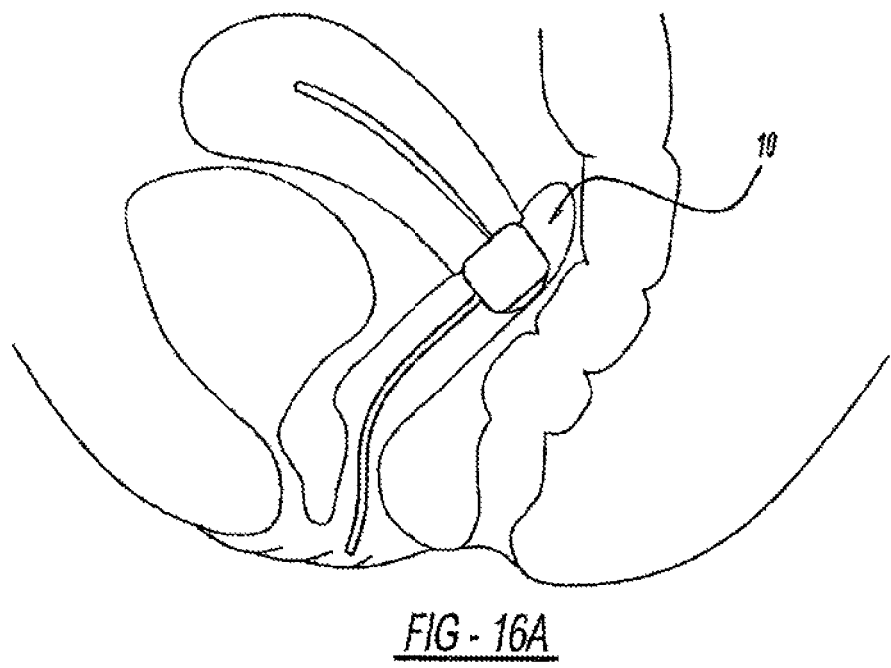

In another embodiment, shown in FIGS. 15A-15D, device 200 includes a stabilizing body 202 having an anterior end 204 and posterior end 206, the posterior end 206 including magnets 210 that act as a docking mechanism for receiving an occluding member 208 having magnets 210'. In this device 200, the stabilizing body 202 and occluding member 208 are separate pieces. Preferably, the stabilizing body 202 is generally as described above and the same shape, with the addition of magnets 210 in the posterior end 206 for receiving the occluding member 208. The device 200 preferably is situated in the vagina such that the anterior end 204 rests around the pubic notch and the posterior end 206 rests in the posterior formix. The occluding member 208 has corresponding magnets 210' in areas that line up with the magnets 210 of the posterior end 206. The occluding member 208 can be a rigid material, or it can be semi-rigid and expandable, or compliant as described above. The occluding member 208 can include an insertion mechanism 212 that can be used for ease of insertion into the vagina and can aid in stabilizing the occluding member 208 within the stabilizing body 202. When in place, the insertion mechanism 212 can reach from the occluding member 208 to the anterior end 204, as shown in FIG. 15D. The stabilizing body 202 can alternatively, or in addition to the magnets 210, include a mechanical lock 214. In this case, the occluding member 208 also includes a matching mechanical lock 214' to secure the occluding member 208 in the stabilizing body 202. The docking mechanism can also be shape fit, i.e. the shape of the device 200 itself that allows for docking. When it is desired to prevent the passage of stool, the occluding member 208 can be inserted (and optionally expanded) and held in place by the magnets 210, 210' and/or the mechanical lock 214, 214'. The occluding member 208 can be adjustably docked along the length of the stabilizing body 202. The occluding member 208 can also cause the stabilizing body 202 to apply force. When it is desired to let stool pass, the occluding member 208 is removed (and optionally contracted). The occluding member 208 can further include mechanisms for removal, as described above, such as string, a tube, wire, a ring, a tab, a chain, or a flexible rod. In this embodiment, the stabilizing body 202 can be surgically implanted in the vagina and remain inside, whereas the occluding member 210 can be inserted or removed as desired, shown in FIG. 15E. In this case, the occluding member 210 can be disposable whereas the stabilizing body 202 is more of a permanent device. The present disclosure also provides for the occluding member 210 itself for controlling the passage of stool, wherein the occluding member 210 is a body and includes a securing mechanism for securing the occluding member 210 to a dock on the device 200.

Therefore, present disclosure further provides for a method of controlling the passage of stool in a patient, including the steps of inserting the stabilizing body 202 of the intra-vaginal device 200 into the patient's vagina, inserting the occluding member 208 in the vagina, docking the occluding member 208 on the stabilizing body 202, preventing expansion of the patient's rectum with the occluding member 208, and impeding the passage of stool. Preferably, the anterior end 204 rests around the pubic notch and the posterior end 206 rests in the posterior formix. The docking of the occluding member 208 can occur by the interaction of the magnet.

Therefore, present disclosure further provides for a method of controlling the passage of stool in a patient, including the steps of inserting the stabilizing body 202 of the intra-vaginal device 200 into the patient's vagina, inserting the occluding member 208 in the vagina, docking the occluding member 208 on the stabilizing body 202, preventing expansion of the patient's rectum with the occluding member 208, and impeding the passage of stool. Preferably, the anterior end 204 rests around the pubic notch and the posterior end 206 rests in the posterior formix. The docking of the occluding member 208 can occur by the interaction of the magnets 210, 210' and/or the mechanical locks 214, 214' as described above. The docking step can include placing the occluding member 208 such that it is compressed between the stabilizing body 202 and vaginal wall. The preventing step can include occluding the rectum. The method can further include the step of undocking and removing the occluding member 208 from the vagina, allowing stool to pass. Stool can be allowed to pass also by changing the position of the occluding member 208 instead of removal.

Figure 32A:
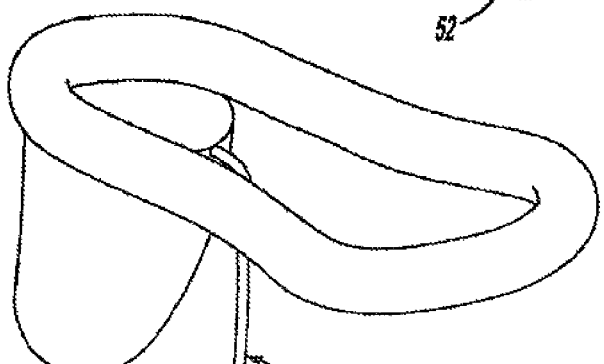
FIGS. 32A-32B are views of the device with a bleed mechanism.
Figure 32B:
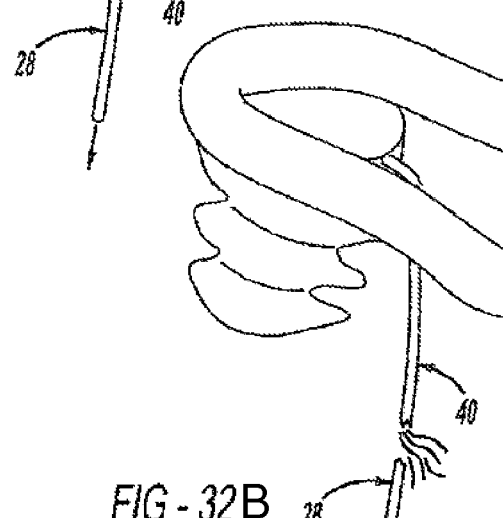

Any part of the devices 10, 100, 200 can be disposable and made of a material that allows for flushing down the toilet after a single use. For example, the expandable member 18/occlusive member 108, 208 can be irreversibly deflated upon activation of a feature. For example, a bleed in the form of a tube/string 40 can be pulled which trips a valve or detaches the tube 40 from the expandable member 18 or generally causes leakage of fluid, causing it to deflate, as shown in FIGS. 32A-32B. This allows the patient to pass stool and the device 10 is removed and disposed of. Any of the mechanical parts of the expandable member 18, such as the spring 38 can be actuated to irreversible collapse. Another example is the removal of the device 10 causes the stabilizing body 12 to irreversibly collapse or lose structural integrity, shown in FIGS. 27A-27B. The device 10, 100, 200 can be encased in an applicator, which is inserted in the vagina and upon actuation; the device expands into proper shape and rectal occlusion. A disposable pump (e.g. a bag filled with an amount of air) can be included with the device 10, 100, 200, which can be squeezed after insertion and then can be torn off and disposed of. The removal of the device 10 can also cause an irreversible mechanical compromising of the device 10 that prevents future use.

The present disclosure also provides more generally for a device including a stabilizing body for stabilizing the device in a body orifice and a force applying portion for applying force to an orifice wall, the stabilizing body imparting minimal tension on the walls of the orifice proximate to the force applying portion, such that the force applying portion can displace the orifice wall. In other words, the device 10 of the present disclosure is not limited to use in the vagina for rectal occlusion, but can be made in different sizes for different applications throughout the body. The stabilizing body can narrow proximate to the force applying portion to minimize tension on the orifice wall. A region proximate to the force applying portion can be narrower than one or both ends of the device. The force applying portion can reversibly apply force. The applied force can be imparted on a neighboring structure.

Therefore, the present disclosure also provides for a method of controlling flow of a substance through a body orifice, by stabilizing a device 10 and preventing rotation and translation in the body orifice, reversibly applying force to the same area of the body orifice with the device 10, and controlling the flow of the substance through the body orifice. This method can be performed as described above but it can be used in any part of the body, not just in the vagina for rectal occlusion.

One aspect of the disclosure is an intra-vaginal device for the control of stool passage of an adult human female user, the device comprising a reversibly extendable occluding portion, and an intra-vaginal stabilizing portion supporting the occluding portion, wherein the stabilizing portion is adapted to fit entirely within the user's vagina such that it maintains the occluding portion in contact with the recto-vaginal septum in extended and non-extended states to control the passage of stool through the user's rectum. It should be noted that extensions that exit the vagina, but do not provide stabilization or positional support for the device are not intended to be excluded by our use of the terms entirely intravaginal and intravaginal.

FIGS. 37A and 37B illustrate an exemplary intra-vaginal device for the control of stool passage. Device 100 includes occluding portion 102 and stabilizing portion 104. The occluding portion and the stabilizing portions are together, an example of a body that is sized and configured to fit entirely within an adult human vagina. Occluding portion 102 includes extendable member 103, which is adapted to be reversibly extended between extended and non-extended states. FIG. 37A illustrates occluding portion 102 in an extended configuration. Stabilizing portion 104 is secured to occluding portion 102, and the device is sized and configured to stabilize the device entirely within a user's vagina when occluding portion 102 is in both extended and non-extended states. Device 100 is sized and configured to cause occluding portion 102 to repeatedly extend against the recto-vaginal septum and at least partially occlude the rectum even after repeated transitions to a non-extended state. The flattened body of the stabilizing portion 104 in comparison to the length of the occluding portion 102 (the length it extends from the stabilizing portion 104), and more specifically the direction of expansion of the occluding portion 102, allows the device to minimize the stretch on surrounding vaginal tissue in order to occlude the rectum; and it keeps the device stable. The features of the flattened body, the occluding portion, and their relationship to each other that allow for occlusion, stability, and comfort, of device 100, will be detailed throughout the disclosure.

Stabilizing portion 104 includes stabilizing body 105 that has a thin, low-profile body in comparison to occluding portion 102. Stabilizing portion 104 also includes a cushioning member 107 that is generally adapted to reduce or minimize trauma to vaginal tissue, particularly in response to the extension of occluding portion 102. Cushioning member 107 includes surface 108 adapted to engage vaginal tissue.

FIGS. 38A-F illustrate an exemplary intra-vaginal device for the control of stool passage. Device 120 includes occluding portion 122 and stabilizing portion 124. Occluding portion includes extendable member 123 that is adapted to be reversibly extended between extended and non-extended states. Occluding portion 122 is in fluid communication with line 134, which can be used to add or remove fluid from within occluding portion 122, which is described in more detail below. Extendable member 123 is adapted to extend from a non-extended state to an extended state when filled with fluid (e.g., air, saline) via inflation line 134. The extension is reversed when the fluid is removed from occluding portion 122 via line 134. Exemplary ways to add or remove fluid from an occluding portion are set forth herein. Occluding portion 122 is shown in an extended configuration, and is secured, either directly or indirectly, to stabilizing portion 124.

Stabilizing portion 124 includes stabilizing body 125, which has an annular and planar configuration. Stabilizing body 125 is a transparent material such that internal components of stabilizing portion 124 can be visualized within the stabilizing body, but stabilizing body 125 need not be a transparent material. Stabilizing portion 124 also includes a stabilizing member disposed within stabilizing body 125, which in this embodiment includes spring 121 and first and second wireforms 126 and 129. Wireforms 126 and 129 are secured to respective ends of spring 121. Wireform 129 has a first end secured to spring 121 and second end 131 that has a smaller radius of curvature than a portion adjacent to 131. In this embodiment end 131 is bent back on itself. Wireform 126 similarly has a first end secured to spring 121 and second end 130 that forms a portion with a smaller radius of curvature than a portion adjacent to end 130. In this embodiment end 130 is bent back on itself. This wireform structure, including portions 130 and 131, help support occluding portion 122 stay in a prescribed orientation and resist angular movement due to forces imposed on it by the user's body.

For clarity, FIG. 38C illustrates a top view of the stabilizing member in isolation from the rest of device 120, illustrating spring 121 and wireforms 126 and 129. Spring 121 is secured to wireforms 126 and 129 by any number of suitable adhering techniques, such as welding, adhesive bonding and a friction fit. In some embodiments spring 121 is stainless steel, but can be any suitable material. The use of "spring" herein includes traditional springs as well materials with spring-like characteristics. For example, the spring can be a section of stainless steel that is laser cut to form a spiral pattern. In these embodiments the cut pattern can be varied to achieve desired properties of the spring.

In some embodiments one or more portions of the stabilizing member is an elastic polymer material. For example, the stabilizing member can be a silicone, a urethane, or other flexible material. In some embodiments the elastic polymer is more rigid than the stabilizing body. In some embodiments the stabilizing body is filled with the material and then the material is cured inside the stabilizing body.

For clarity, FIG. 38D illustrates a top view of stabilizing portion 124 in isolation from the stabilizing member and occluding portion 122. Stabilizing portion 124 includes stabilizing body 125 secured to cushioning member 127 at locations 135. Stabilizing body 125 is a tubular element that defines a channel in which spring 121 and end sections of wireforms 126 and 129 are disposed. In an alternate embodiment, stabilizing body 125 can be an overmolded element. This embodiment may further incorporate such additional features as the wireforms and spring within it. Cushioning member 127 is a section of material that is adapted to reduce trauma to vaginal tissue in the vicinity of the cushioning member 127. In this embodiment cushioning member 127 is a solid or semi-solid material that provides flexibility and deformability to prevent damage and discomfort to tissue adjacent the cushioning member, described in more detail below.

In some embodiments stabilizing body 125 is a flexible material that avoids injuring or causing discomfort to the patient. In some embodiments stabilizing body is a tubular silicone material, but could be made from any number of flexible and biocompatible materials. The stabilizing member disposed therein can provide rigidity to the stabilizing portion while the stabilizing body provides a softer, more flexible material to interface the vaginal tissue.

The ends of wireforms 126 and 129 that are secured to spring 121 are also disposed within the ends of stabilizing body 125. Wireforms 126 and 129 are disposed within the solid or semi-solid cushioning member material.

In an exemplary embodiment of a method of manufacturing, ends of wireforms 126 and 129 are secured to the ends of spring 121. The assembled stabilizing member is advanced into one end of tubular stabilizing body 125 until spring 121 is disposed centrally within stabilizing body 125. Wireforms 126 and 129 are placed in a mold with the desired cushioning member shape, and the mold is filled with the cushioning member material. The mold is closed and the cushioning member material cured. The wireforms are therefore embedded within cushioning member 127. The configuration of the two cushioning member arms helps maintain the spring and stabilizing body 125 in the curved configuration and provides the stabilizing portion 124 with the general annular configuration.

In an exemplary embodiment of a method of manufacturing, the cushioning member is formed by filling a mold with cushioning member material; the material is cured and removed from the mold. Wireforms 126 and 129 are bonded into the cushioning member. Spring 121 is bonded to one of wireforms 126 or 129. One end of the tubular stabilizing body is advanced over the bonded spring and wireform, the other end of the tubular stabilizing body is advanced over the other wireform and the assembly is adjusted such that the second wireform is inserted into the spring. The tubular stabilizing body is then bonded to the cushioning member. The extendable portion is then bonded to the cushioning member and the inflation tubing attached to the extendable portion.

Cushioning member 127 need not be attached to stabilizing body 125 at the exact locations 135. They can be secured to each other closer to the posterior end of the device or closer to the anterior end of the device. Additionally, they need not be secured in the same location on both sides. In some embodiments, the cushioning member is located in the vicinity of the occluding portion, as there can be force concentrations in this area. In some alternate embodiments, the cushioning member can be disposed on the portion of the device that resides closest to the cervix, even if the occluding portion is located at a different area. In other embodiments, the stabilizing body may have a cushioning portion, or cushion portions, on one or more of an extended portion along the stabilizing body, such as the lateral extents of the stabilizing body; or the distal portion of the stabilizing body that resides closest to the pubic arch.

In other embodiments the stabilizing body and cushioning member are integrally formed as a single structure and are therefore not two separate components attached to one another. For example, the stabilizing portion includes an integral stabilizing body and cushioning member. A mold with the overall general shape of the entire stabilizing portion can be used to form the integral stabilizing portion. A stabilizing member, such as shown in FIG. 38C, can be formed within the integral stabilizing portion.

In other embodiments, the cushioning member is comprised of a fluid filled structure. This structure can be integral to, or separate from, the occluding portion. An exemplary embodiment of this is shown in FIG. 67 and described in more detail below.

In some embodiments the stabilizing portion does not include a stabilizing member disposed within the stabilizing body. In some embodiments only a portion of the stabilizing body includes a separate stabilizing member disposed therein. For example, in the embodiment in FIGS. 38A-F, the stabilizing member could simply be spring 121 disposed in the anterior portion of stabilizing body 125.

FIG. 38F illustrates a partially exploded side view of device 120, illustrating occluding portion 122, in an extended configuration, detached from stabilizing portion 124.

As mentioned above, if sufficient slack does not exist in the vaginal wall near the occluding portion before the occluding portion is extended, the occluding portion may not be able to adequately deform the vaginal wall, which could result in suboptimal occlusion, very little occlusion, or no occlusion at all. This is shown and described generally in reference to FIGS. 7A-7D above.

In the embodiment in FIGS. 38A-F, the occluding portion is secured to the stabilizing portion near the perimeter of the stabilizing portion. The lateral dimension of the stabilizing portion adjacent the occluding portion is less than the lateral dimension of the stabilizing portion at a wider portion of the stabilizing portion. In this embodiment this is true because the stabilizing portion is annular and the occluding portion is disposed at the periphery of the annulus. The relative lateral dimensions could, however, be applicable with different shape and configurations of both the stabilizing portion and the occluding portion. Because the lateral dimension of the stabilizing portion is relatively smaller adjacent the occluding portion, the lateral stretch on vaginal tissue in this area when the occluding portion extends posteriorly is reduced. FIG. 7D above generally illustrates the sufficient amount of slack that is retained adjacent the occluding portion when the device in FIGS. 38A-F is inserted and extended. Reducing the stretch in this area maintains slack in this region and allows the occluding portion to effectively extends towards the rectum and occlude or partially occlude the rectum, as is shown in FIG. 7D. The slack can be maintained yet the stabilizing portion, at more anterior locations, is wide enough to be secured adjacent the inferior pubic ramus.

Figure 39A:
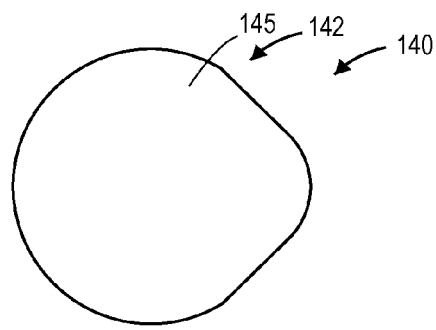
Figure 39B:
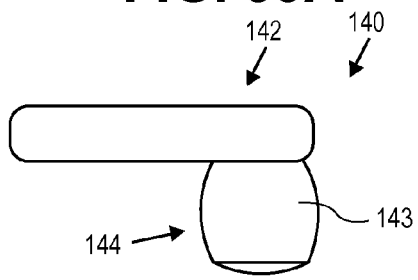

FIGS. 39A and 39B illustrate an exemplary intra-vaginal device for the control of stool passage. FIG. 39A is a top view and FIG. 39B is a side view. Device 140 includes stabilizing portion 142 and occluding portion 144. Stabilizing portion 142 includes stabilizing body 145 that does not have an opening as in the embodiment in FIGS. 38A-F. Stabilizing body 145 is secured to extendable member 143. Stabilizing body 145 is adapted to stabilize the device within a user's vagina when the occluding portion is extended or not extended. In some embodiments substantially the entire anterior surface of stabilizing body 145 is a cushioning member. Stabilizing body 145 can additionally have one or more holes therein to allow for the passage of vaginal fluid from one side of the stabilizing body to the other, as is generally described above.

Figure 40A:
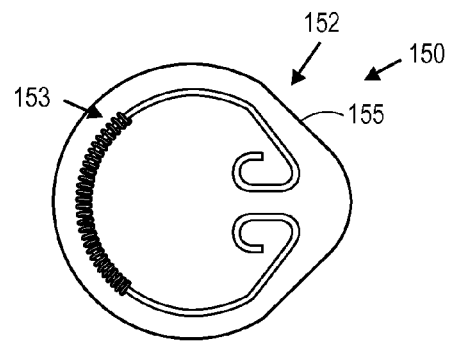
Figure 40B:
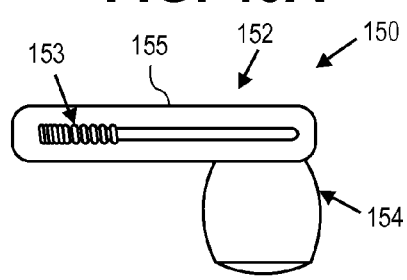
Figure 42A:
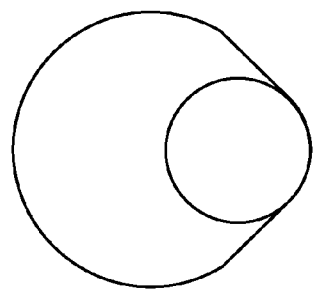

FIGS. 40A and 40B illustrate (top view and side view, respectively) an exemplary intra-vaginal device for the control of stool passage. Device 150 includes stabilizing portion 152 and occluding portion 154. Device 150 includes cushioning body 155 and stabilizing member 153 therein, which includes the same components as the stabilizing member from the embodiment in FIGS. 38A-F. Stabilizing portion 152 does not include an opening therein.

Figure 41:
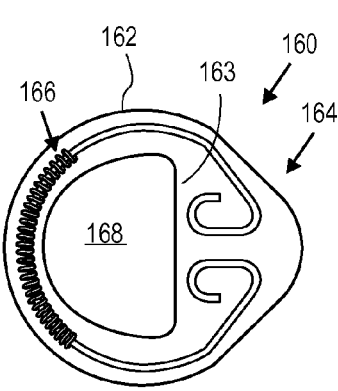
Figure 42B:
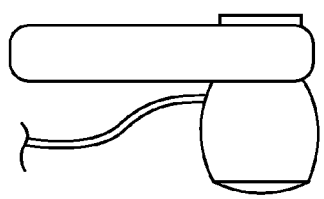

FIG. 41 illustrates a top view of exemplary stabilizing portion 160 for an intra-vaginal device for the control of stool passage. Stabilizing portion 160 includes stabilizing body 162 secured to cushioning member 164, similar to the way in which they are secured in the embodiment in FIGS. 38A-F. In this embodiment the cushioning member has a more linear surface 163 adjacent opening 168 than does the embodiment in FIGS. 38A-F. Device 160 has a generally annular configuration defining opening 168, and a portion of cushioning member extends or fills in opening 168. The opening 168 can be larger or smaller than that shown in FIG. 41.

Figure 43:
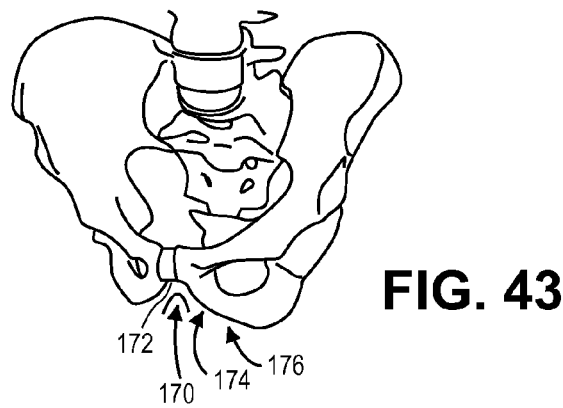
FIG. 43 is a perspective view illustrating the bones of the pelvis of a human.

As background material for an exemplary method of use, FIG. 43 is a perspective view illustrating the bones of the pelvis of a human. 170 is the pubic arch, 172 the public symphysis, 174 is the inferior pubic ramus, 176 is the ischiopubic ramus. The "pubic arch" is also referred to herein as the "pubic notch." The terms "inferior pubic ramus," "ischiopubic ramus," and "pubic notch" are used herein to generally refer to the location adjacent the pubic symphysis. The "pubic notch" can also describe a "nook", or indentation, or depression formed adjacent to the pubic symphysis, anterior and superior to the introitus.

As described in more detail below, at least a portion of the stabilizing portion is stabilized by one or more of the boney structures of the pelvis, generally posterior and superior to the boney structure, in order to stabilize the occluding portion against the recto-vaginal septum such that it repeatedly extends against the recto-vaginal septum towards the rectum to at least partially occlude the rectum. Herein, when referring to the boney structures, it is assumed that the soft tissue and musculature surrounding the boney structure, and generally forming the pelvic floor, are also involved in the stabilization of the device. In fact, it is possible for the soft tissue and musculature of the pelvic floor to provide most or all of the stabilization of the device, but since these structures are themselves supported by, or in the same vicinity as the underlying boney structure, the boney structure is generally referred to as the anatomical feature to provide the stabilization.

Figure 44A:
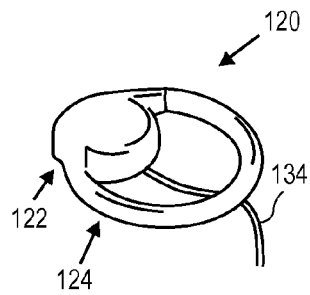
FIGS. 44A-44F illustrate an exemplary method of positioning an exemplary device within the vagina.
Figure 44B:
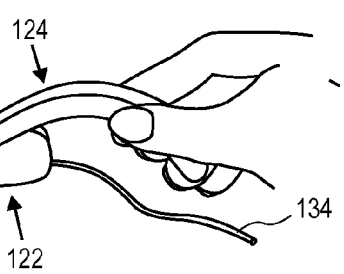
Figure 44C:
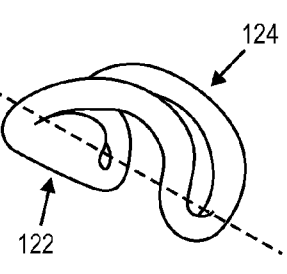

FIGS. 44A-E illustrate an exemplary method of using device 120 that is shown in FIGS. 38A-F. FIG. 44A illustrates device 120 including occluding portion 122 in a non-extended configuration, and stabilizing portion 124. To ease in the insertion into the vagina, device 120 is adapted to be deformed into a delivery configuration, which is shown in FIGS. 44B and 44C. The device is adapted to be easily collapsed along axis F, which is shown in FIG. 38C. In this embodiment the device is collapsed by folding the device along axis F. The flexibility and deformability of spring 121 allows for the device to be collapsed along axis F. Additionally, the discontinuity between the ends of wireforms 126 and 129 allows the stabilizing member at the proximal end of stabilizing portion 120 to accommodate the collapsing motion along axis F. Portions 130 and 131 of wireforms 126 and 129 are shaped such that when the device is folded, they aid in folding the cushioning portion and the occluding portion along axis F. It is disclosed that, in an embodiment such as FIG. 38C, portions 130 and 131, the firm component(s) that comprise the stabilizing body, has/have more area, in the proximity of the force applying portion. The firmer component is meant to refer to anything that gives the stabilizing body structural support. It was discovered through clinical testing that designing the device to have more area of the firmer component of the stabilizing body in the proximity of the occluding portion adds stability to the occluding portion during occlusion. Additionally, appropriate termination of the firmer component inside the softer cushion or occluding portions minimizes damage during repeated folding. The shape of sections 130 and 131 of FIG. 38C demonstrate one embodiment of a termination that does not cut, or otherwise damage the soft portion it is embedded in after multiple fold cycles.

FIG. 44C shows the device collapsed into the delivery configuration without the user's hand. In some embodiments a separate tool can be used to collapse the device and is used to insert the device into the vagina so that a user need not use a hand for insertion and positioning. In the collapsed delivery configuration, device 120 is inserted through vaginal opening 180, which is identified in FIG. 44D. Still in the delivery configuration, the stabilizing portion is advanced into the vagina until the lateral-most portions of stabilizing portion 124 clear the inferior pubic ramus. The forces applied to the device to deform it into the delivery configuration are then released, and stabilizing portion 124 then self-reverts, or self-expands, to the planar stabilizing configuration, as is shown in the stabilized position in FIG. 44D. As can also be seen in the superior view (i.e., the view looking down) of FIG. 44E (only stabilizing portion 124 and boney pelvic structures are shown for clarity), the stabilizing portion is sized and configured such that the lateral portions (i.e., right and left) of the stabilizing portion are disposed further laterally than adjacent boney structure such that the boney structure provides a stabilizing support for stabilizing portion 124. Alternatively stated, the lateral span, or width, of the stabilizing portion, is greater than the lateral span of the inferior pubic ramus. Stabilizing portion is thereby secured by the boney structures of the pubic notch in a location posterior to the pubic notch.

As stated above, the boney structures described herein are also intended to be inclusive of the tissues and musculature attached thereto, and the interference described which provides stabilization of the device can be resultant on these tissues and musculature as well.

Figure 44D:
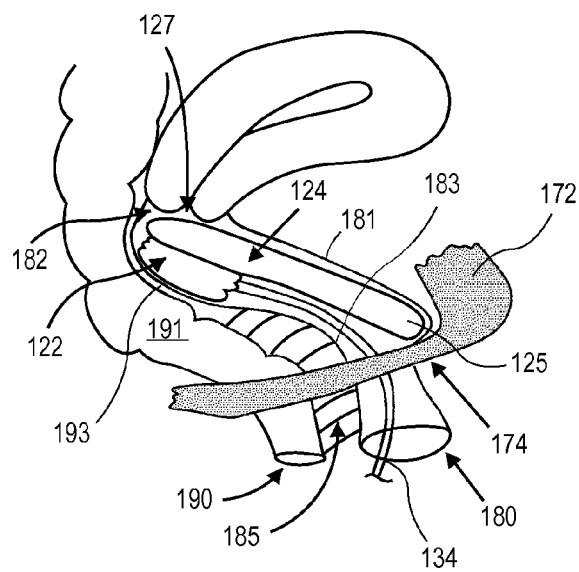
Figure 44E:
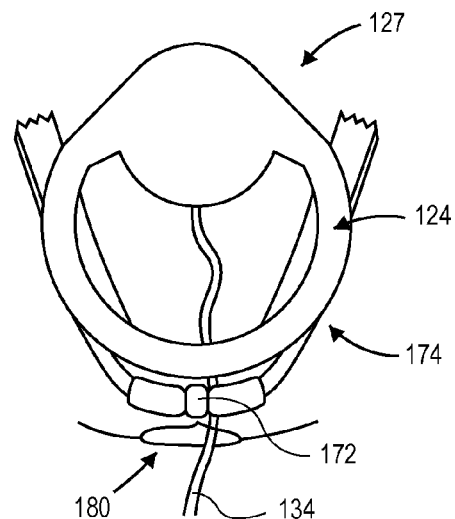

FIG. 44E also illustrates how the rounded distal portion of this embodiment provides a secure fit into the pelvic anatomy. The generally rounded shape, being sized to fit proximal to the pubic arch, can securely engage the anatomy proximal to the pubic arch to prevent expulsion. More specifically, the device is sized and configured for the distal end of the device to fit anteriorly in the notch formed by the pubic ramus 174. This can also be seen in the lateral view of FIG. 44A, where body 125 rests near boney structure 174. Additionally, this shape evenly distributes any forces required in this area to counter an outward expulsion, which may occur as a result of occluding portion expansion, or stool forces on the occluding portion.

FIG. 44D also illustrates the position of anterior surface of the vagina 181, cervix 182, posterior surface 183 of the vagina, rectal opening 190, and rectal lumen 191, boney pubic symphysis 172, and inferior pubic ramus 174. When the lateral portions of the stabilizing body are secured by the boney structure of the pubic arch, the proximal end of stabilizing portion 124 is disposed at the proximal portion of the vaginal vault. In particular, in this embodiment, the proximal portion is disposed adjacent the cervix, or posterior formix. In women who have had a hysterectomy and thus not do have a posterior formix, the proximal end of the stabilizing portion is disposed at the proximal end of the vaginal vault. As used herein, the proximal end of the vagina vault is used to describe the proximal end of the vagina, whether the patient has a cervix or not. It should be noted that the device need not engage the extreme ends of the vagina for the same stabilization and occlusive features of the device described herein to function. Some users of the device have more tone in the vagina to help secure the device with greater clearance than what is depicted in FIG. 44D.

In the position shown in FIG. 44D, the stabilizing portion is stabilized between the pubic notch and posterior end of the vaginal vault, and is stabilized proximal to the inferior pubic ramus.

In this position the device is stabilized by three locations of stabilization: one on each of the lateral portions of the stabilizing portion, and one on the proximal end of the stabilizing portion. These three locations generally define a stabilization plane for the device.

There are other device configurations that can effectively remain in an intra-vaginal position and control the passage of stool through the rectum. Some embodiments utilize all three locations in the above-mentioned stabilization plane, with the location in the proximal vagina sometimes being the occlusive portion itself. Some embodiments in the disclosure herein describe entirely intra-vaginal stabilization and rectal compression via these stabilization locations and additionally at least one other feature described herein, including: the specific dimensional and positional characteristics of the occlusive portion, the dimensions and configurations of stabilizing portions, combinations of the above referenced occlusive and stabilization characteristics, and cushioning portions.

In some embodiments the three-point stabilization, in conjunction with one or more other features described herein, describes an entirely intra-vaginal device that can stably provide a compressive force to the rectum via the vagina.

When the stabilizing portion is in this position, non-extended occluding portion 122 is disposed and stabilized against the recto-vaginal septum 193, as shown in FIG. 44D (although it need not be in direct contact with the tissue in the non-extended state). Cushioning member 127, which is disposed generally on the anterior side of the vagina, and substantially opposite occluding portion 122, is in the posterior end of the vaginal vault. Cushioning member 127 includes surface 128 that is adapted to engage vaginal tissue on the anterior side of the vaginal in the area of the proximal end of the vaginal vault. Cushioning member 127 can also include lateral surfaces that are disposed to contact the lateral walls and proximal end of the vagina.

The stabilizing portion is also sized and configured such that the occluding portion is positioned posterior to perineal body 185, identified with lines. Through human clinical testing, it was more difficult to obtain intravaginal rectal occlusion through tissue deflection in the area of the perineal body than in the area proximal to the perineal body. This result was unanticipated because the rectal canal is narrower in the region of the perineal body. Users also felt greater discomfort when force was applied to the perineal body as compared to proximal to the perineal body. In this figure, the specificity of the stabilizing and localizing features of the device are apparent: the device is sized to fit stably within the described pelvic anatomy to maintain the occlusive portion in the described optimum area for occlusion.

Figure 44F:
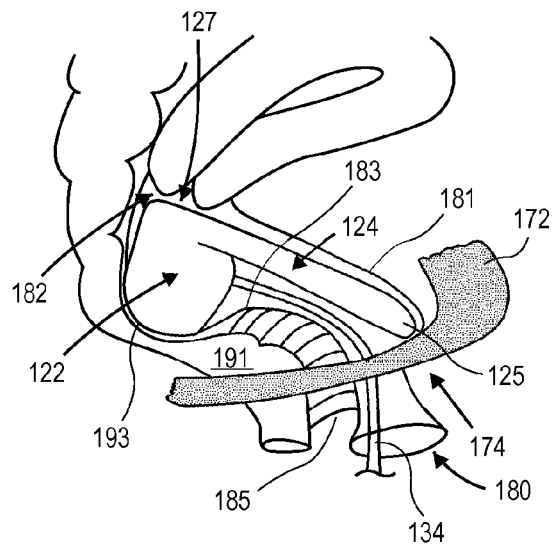

Once device 120 is stabilized in the position shown in FIG. 44D, occluding portion 122 is extended to an extended configuration as shown in FIG. 44F by inflating it with a fluid via line 134. Upon extension, occluding portion 122 pushes against the recto-vaginal septum 193 in the direction of the rectum 191, deflecting the recto-vaginal septum 193 and occluding rectum 191. Occluding portion 122 is disposed against the recto-vaginal septum 193 posterior to perineal body 185. Less force is required to deflect the septum into the rectum posterior to the perineal body, and the user is less likely to experience discomfort. By stabilizing the device such that the occluding portion is this deep into the vagina, extension of the occluding portion brings the two sides of the rectum together (i.e., it extends in a direction that is more closely perpendicular to the longitudinal axis of the rectum). In the occluded configuration, the two sides of the rectum are moved closer to one another, occluding the rectum, and preventing the passage of stool.

The "occluding portion" as described herein can also be considered the material interface that presses against the rectovaginal septum, while the extending portion is the mechanism (e.g. balloon, mechanical extension, etc.) that creates the displacement of the material interface. While the occluding portion and the mechanism can be the same structure (e.g. a balloon), they need not be. For example, an occluding portion can be extended on a free end of a cantilevered arm, wherein the angle of the cantilevered arm (and thus the displacement of the occluding member) is adjusted by an expandable element on the side of the arm opposite the occluding portion. Furthermore, the term "extendable portion" is meant to refer to a portion such that when it is extended, protrudes into the rectum, and when it is not extended, does not protrude as much into the rectum. The portion may or may not be extendable itself, so long as it can vary its amount of protrusion into the rectum.

When a user wishes to deform the occluding portion back towards the non-extended state shown in FIG. 44D, the fluid is removed from the occluding portion via line 134, deforming the occluding portion to the non-occluded state. In this state the stool, which may be stool that has accumulated in the rectum, is allowed to pass. One of the advantages of the device is that even in the non-occluded state shown in in FIG. 44D, the device remains stabilized in the vagina in the orientation shown in FIG. 44D, with the occluding portion positioned adjacent the septum so that it can expand in the same manner and same direction as shown in FIG. 44F. This allows the device to repeatedly extend in the desired direction to properly occlude each and every time the user expands the occluding portion. Some of the prior art attempts do not describe a device that provides for intra-vaginal stabilization via a separate stabilizing portion when the occluding portion is in the non-occluded configuration. The prior art devices are free to re-orient themselves within the vagina. Unfortunately, if the prior art devices have re-oriented themselves, when the user re-expands the prior art occluding portion, the occluding portion can extend is a non-desired direction, perhaps not even towards the rectum. This is unacceptable for a device that is intended to remain in a stable position and be repeatedly extended and collapsed.

Figure 45:
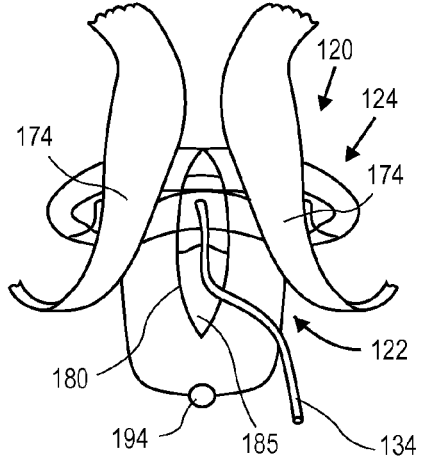
FIG. 45 shows an inferior and slightly anterior view of FIG. 44F.

FIG. 45 shows an inferior and slightly anterior view of FIG. 44F, with device 120 positioned within the vagina. The device is shown with solid lines even though the device (with the exception of line 134) is disposed within the vagina. Line 134 extends through vaginal opening 180, and anus 194 is also shown. Stabilizing portion 124 is shown proximal to inferior pubic ramus 174. Perineal body 185 is seen through vaginal opening 180, distal to extended occluding portion 122, which is extended down towards the rectum.

In some patients, when the occluding portion is in the occluded state, reaction forces are applied from the vagina and surrounding pelvic structures on the occluding portion that can result in the device rotating and/or translating to undesired locations or positions within the vagina. Particularly, the occluding portion can be moved out of position, preventing it from repeatedly being extended in a desired location to occlude the rectum. To keep the occluding portion disposed against the recto-vaginal septum, the device should be able to withstand these reaction forces without substantially rotating or translating. That is, the device should be adapted to maintain its orientation. There may be some minor, temporary rotation or translation, but as long as the occluding portion is stabilized to be able to repeatedly apply force against the septum towards the rectum, occlusion can occur. For example, if a user bears down, the device may rotate or translate very slightly, but it is still maintains the same orientation.

A device structure that does not comprise a portion or portions that protrude or extend towards the anterior wall generally, or relative to other portions, will distribute the reaction force of the occluding member without pushing into the anterior wall of the vagina to cause discomfort for the user. In other words a device that is configured to not press into the anterior wall will cause less comfort for the user. The anterior portion of the vagina is susceptible to discomfort due to distension, especially the medial area, which is adjacent the bladder. A structure that is uneven or protruding relative to other portions on the anterior side might tend to create localized pressures and more discomfort, especially when the device is subject to forces pushing towards the anterior vaginal wall. Previous attempts have not described a device for bowel control with an anterior-facing side that is designed to distribute forces as described above.

Figure 46:
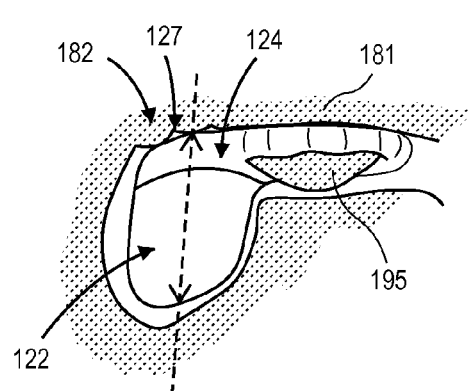
FIG. 46 illustrates an exemplary device with an occluding portion in an extended configuration within a user's vagina.
Figure 54:
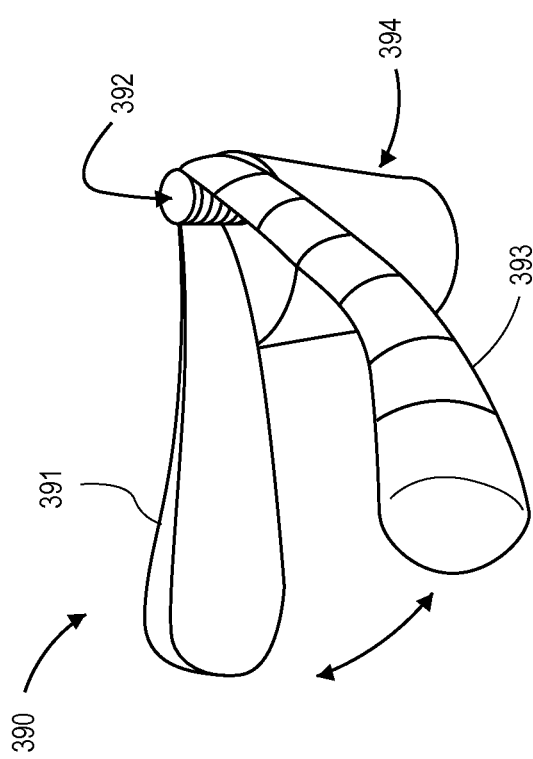

FIG. 46 illustrates device 120 with occluding portion 122 in an extended configuration within a user's vagina. Stabilizing portion 124 is shown engaging anterior vaginal wall 181, and an exemplary user's vaginal wall is shown being free from distention imposed by the device, and a medial section of the anterior vaginal wall is depicted as free to occupy the space within the annulus of the device. While the anatomy depicted in this figure shows a pronounced bulge in the medial section, this is not necessarily representative of all users' anatomy. This figure is depicted to highlight the effect of the annular configuration of stabilizing portion 124 being adapted to distribute the reaction force evenly in response to the extension of occluding portion 122. An embodiment that is not necessarily an annular structure, but is generally uniform on the anterior side and not protruding significantly towards the anterior wall, will distribute the force from the occluding portion such that the anterior wall of the vagina is not unduly distended. For example, this can be a solid stabilizing body that is generally planar (the orientation of the plane being roughly defined as being perpendicular to the direction of force application), similar to the device of FIG. 39A. In this example, the lateral span of the stabilizing body further helps distribute the force evenly. An alternate example is shown in FIG. 54, which would also isolate forces around at least the medial portion of a user's anterior vaginal wall.

FIG. 46 also shows cushioning member 127 being pressed up against cervix 182 in response to extension of the occluding member 122. The relative softness and deformability of cushioning member 127 helps reduce trauma to cervix 182 (or to a vaginal cuff if the cervix has been removed). In this embodiment, cushioning member 127 provides a cushioning effect in substantially the opposite direction to the direction of extension. The dashed lines with arrows indicate the general directions of extension of occluding portion 124, and the generally opposite direction in which cushioning member 127 provides cushioning in the area of the cervix or a vaginal cuff. It should be noted that the cushioning features described herein can also extend a distance along the sides of the occluding portion as well as along the stabilizing body. It should be noted that a cushioned portion could also comprise a larger curvature of radius of the device, especially in the area of the cervix, in order to reduce trauma.

The cushioning member is a portion of the stabilizing portion that applies a great deal of the reaction force onto the vagina in response to the extension of the occluding portion. By making it softer and more deformable, the user is less likely to experience bruising or discomfort in that area. The cushioning member has a generally curved surface that is adapted deform as needed to minimize trauma.

In some embodiments the cushioning member is generally more flexible that other portions of the stabilizing portion. For example, in the embodiment shown in FIGS. 38A-F, the cushioning member is more flexible than the distal portion of the stabilizing portion.

In some embodiments the cushioning member is a solid or semi-solid material. In some embodiments it is solid body of material comprising a pocket or pockets that are filled with a gel or gel-like material to increase the cushioning. In some specific embodiments the material is a soft silicone with a durometer of less than about 10 A.

The cushioning member, in some embodiments, comprises an outer layer filled with a more viscous material inside the outer layer. For example, the cushioning member can have a soft silicone outer shell filled with a silicone gel inside. Increasing the contact area of the cushioning member can reduce the trauma to vaginal tissue.

The cushioning member should be easily collapsible or foldable to a delivery configuration. Additionally, the stabilizing device has to have enough overall stiffness to be stabilized in the vagina. The cushion therefore may have to be able to transition to a stiffer anterior section of the stabilizing portion. For example, in the embodiment in FIGS. 38-F, the anterior portion of the stabilizing portion is more rigid than the cushioning member. This allows the cushioning member to protect the vaginal tissue near the occluding portion, but the stiffer anterior portion can keep the device stabilized in the vagina and keep the occluding portion stabilized against the septum. Alternatively, as stated above, the entire stabilizing body can act as a cushioning element.

In the embodiments in FIGS. 38A-F, the cushion contains the relatively more rigid stabilizing wireforms therein, which fixes the location and extension angle of the occluding portion with respect to the stabilizing portion. This also prevents deflection of the occluding portion into the annular space of the device when there are forces on the device, such as forces from stool. The described wireform shape adjacent the cushion can also aid in folding the cushion when the device is folded for insertion.

While the cushioning member has been primarily described in relation to the figures identified above, such a cushioning member is also applicable to other embodiments described herein, and generally to any intra-vaginal device that can apply force to portions of the vagina, resulting in transferred forces to other portions of the vagina. Additionally, the cushion embodiments described herein, especially as related to their general structure, can be adapted to be applied to other static intra-vaginal devices as well, as even these devices may have certain points of contact with the vaginal wall that require better force distribution. Specifically, a cushion can be added to the proximal portion of any intravaginal device in order to prevent bruising or tissue damage to the cervical region.

Figure 47:
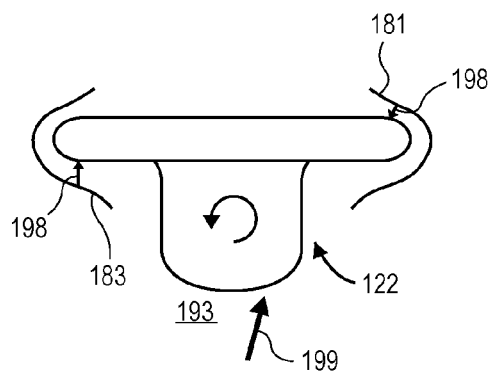
FIG. 47 illustrates an exemplary device within a user's vagina and an occluding portion that is extended.

FIG. 47 illustrates how, in some patient's, stabilizing portion 124 is adapted to stabilize the device in response to forces applied to the occluding portion 124 when occluding portion 124 is extended. As occluding portion 122 is extended, exemplary reaction force 199 is applied on occluding portion 124 from vaginal tissue. Occluding portion 122 may tend to rotate in the direction of circular arrow in response to force 199. Stabilizing portion 124, however, is sized and configured to engage with anterior vaginal wall 181 and posterior vaginal wall 183 and therefore prevent rotation of the stabilizing portion 124 within the vagina. By preventing stabilizing portion 124 from rotating and translating, occluding portion 124 is stably maintained in the proper position against the recto-vaginal septum. In this manner the device can be reversibly extended, and each time the occluding portion 124 is extended it will extend against the recto-vaginal septum above the perineal body in the direction of the rectum to occlude the rectum. This application discloses the occluding portion configured to be located on the center line of the lateral span of the stabilizing body. FIG. 47 represents illustrative forces and is not intended to describe forces that occur in every patient, or even most patients. FIG. 47 merely illustrates how the device is sized and configured to be stabilized in response to the occluding portion being extended, or another external force acting upon it.

Figure 48A:
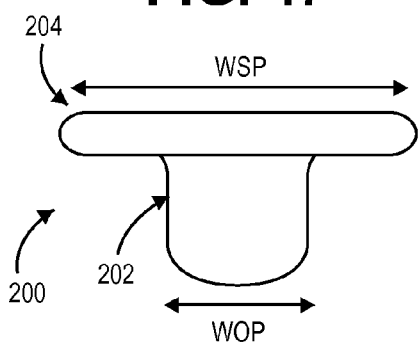
FIGS. 48A-48B illustrate exemplary dimensions of devices set forth herein.
Figure 48B:
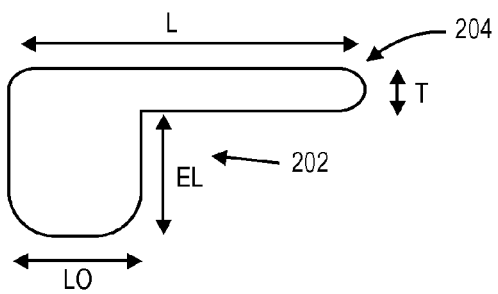

FIGS. 48A-B illustrate dimensions of exemplary device 200. Device 200 includes stabilizing portion 204 and occluding portion 202. FIG. 48A is a posterior view of the device illustrating the width of stabilizing portion "WSP". The WSP is also referred to herein as the "lateral span" of the stabilizing portion. In either case, the stabilizing body need not have a solid mass of material spanning the width. For example, a ring shaped device has a lateral span, even though the ring defines an opening therein. The WSP general refers to the greatest lateral dimension of the stabilizing portion in either an anterior or posterior view. FIG. 48A also illustrates the width of the occluding portion WOP. Similarly, the WOP generally designates the greatest lateral span of the occluding portion. It can refer to the occluding portion in either extended or non-extended configurations. FIG. 48A illustrates the WOP in an extended configuration.

In some embodiments, the WOP is less wide than WSP. This provides a more stable configuration of the device when the occluding portion is extended. For example, FIG. 47 and the description thereof provide an example of how the device is more stable when the occluding portion is extended. For a WSP that is appropriately sized for stability, a WOP of a smaller dimension allows the occluding portion to press into the rectum to an effective depth, while a patient remains comfortable. Even though a WOP equal or greater than the WSP could fit with the dimensions of the surrounding anatomy, it was discovered that reducing the WOP, in relation to the WSP, increased vaginal slack in such a way that allowed for more effective posterior compression of the rectum through the vagina, while maintaining stability. Additionally, the stretch caused by rectal compression when the WOP is equal or greater to the WSP creates discomfort for the user and increases the risk of adverse events. Previous attempts have not described an occluding portion that is less in width than the stabilizing portion in order to produce comfortable and effective rectal compression.

The dimensions and ratios described below apply to a given aspect of a device on average and aren't meant to be limited by localized departures from these dimensions. For example, a device that had a certain thickness, and had a small protrusion that was greater than this thickness, would still be considered to have a general thickness in the region without the protrusion.

FIG. 48B illustrates the length of the stabilizing portion "L," the thickness "T" of the stabilizing portion, the length of the occluding portion "LO", and the extension length EL of the occluding portion. These dimensions are in a side view of the device.

In some embodiments, the thickness "T" is no greater than about 2.5 cm. In another embodiment, the thickness "T" is no greater than about 1.75 cm, and in some embodiments, the thickness "T" is about 5 mm-about 1.5 cm. Testing demonstrated that the thickness of the stabilizing portion played an important role in device function. Reducing the thickness of the stabilizing portion increased the slack in the surrounding vaginal tissue, which turned out to increase the ability of the occluding portion to compress the rectum. These thickness values are smaller than previous attempts at intra-vaginal bowel control devices, some of which describe a tubular, bulkier body.

In some embodiments, the ratio of the thickness "T" to WSP is no greater than about ½. In some embodiments the ratio of the thickness "T" to WSP is no greater than about ⅓. In some embodiments the ratio of thickness "T" to WSP ranges from about ¼-about 1/10. A device with these ratios won't take up too much volume in the vagina, thereby allowing for slack in the vaginal tissue for rectal compression, but has a width dimension that is capable of providing sufficient stabilization in the vagina to withstand the reaction force caused by the occluding portion.

In some embodiments, the ratio of the greatest length of the stabilizing body to the WSP is no greater than about 2. In some embodiments, the ratio of the greatest length of the stabilizing body to the WSP is no greater than about 1.25. In some embodiments, the ratio of the greatest length of the stabilizing body to the WSP is no greater than about 1.1. In some embodiments, the ratio of the greatest length of the stabilizing body to the WSP is no less than about ½. In some embodiments, the ratio of the greatest length of the stabilizing body to the WSP is no less than about ¾. Clinical testing demonstrated that a vaginal bowel control device with these ratios had proper stability to withstand rotation during occluding and non-occluding states.

In some embodiments, the range of effective lengths for the stabilizing body is about 30 mm-about 100 mm. In some embodiments, the range of effective lengths for the stabilizing body is about 44 mm-about 83 mm. In some embodiments the range of effective WSP's is about 30 mm-about 100 mm. In some embodiments the range of effective WSP's is about 44 mm-about 76 mm.

In some embodiments, the volume of the occlusive portion is between about 60 cc and about 10 cc in an extended state. In some embodiments, the volume of the occlusive portion is between a range of about 15 cc and about 50 cc in an extended state. Testing revealed that devices with occlusive portions of these volumes provided an effective amount of occlusion for treating fecal incontinence, while also being comfortable and safe for patient use.

In some embodiments the length of the occlusive portion (inclusive of the stabilizing body and in the direction towards the rectum) is about 20 mm-about 80 mm. In some embodiments, the length of the occlusive portion (inclusive of the stabilizing body) is about 30 mm-about 70 mm. Clinical testing determined a length that extended far enough into the rectum to provide bowel control, but not too far to put an uncomfortable and unsafe amount of pressure on the rectum and vaginal walls. In some embodiments, the WOP is about 20 mm-about 60 mm. In more preferred embodiment, the WOP is about 30-about 60 mm. It was discovered that this width was not too wide so as to reduce the slack in the vaginal tissue and inhibit rectal compression. At the same time, this range was wide enough to create an effective amount of occlusion for bowel control.

In some embodiments, the ratio of the thickness "T" of the stabilizing portion to the extension length "EL" is no greater than about ⅔. More preferably, the ratio of the thickness "T" to the extension length "EL" is no greater than about ½. In some embodiments the ratio of the thickness "T" to the extension length "EL" is within the range of about 0.16-about 0.4. It was an important discovery through clinical testing that the stabilizing body should be thin in comparison to the length of the occluding portion. This allows the stabilizing body to take up less slack in the vaginal tissue, which allows the rectal compression portion to expand posteriorly with less stretch on the tissue and discomfort. Additionally, this ratio allows for the device to collapse to a small enough thickness to allow stool to pass normally in the non-occluding state, since the thickness of the stabilizing body is only a small portion of the total dimension of T plus EL.

In some embodiments, the maximum thickness of thickness "T" plus the thickness of the un-extended occlusive member is no greater than about 3.5 cm. In some embodiments the maximum thickness of thickness "T" plus the thickness of the un-extended occlusive member is no greater than about 2.5 cm. In some embodiments the maximum thickness of thickness "T" plus the thickness of the un-extended occlusive member is no greater than about 1.5 cm. In some embodiments the maximum thickness of thickness "T" plus the thickness of the un-extended occlusive member is in a range from about 0.5 cm to about 1.5 cm. These exemplary combined thicknesses provide a device with dimensions such that don't occupy too great a volume within the vagina, and allow the occluding portion to effectively be collapsed without the rectum being occluded.

In some embodiments, the ratio of the thickness "T" plus the thickness of the un-extended occlusive member to the thickness "T" plus the extended length of the occlusive member ("EL") is no greater than about 0.75. In some embodiments the ratio of the thickness of thickness "T" plus the thickness of the un-extended occlusive member to the thickness "T" plus the extended length of the occlusive member ("EL") is no greater than about 0.5. In some embodiments the ratio of the thickness of thickness "T" plus the thickness of the un-extended occlusive member to the thickness "T" plus the extended length of the occlusive member ("EL") is in the range from about 0.25-about 0.4.

In some embodiments, the ratio of WOP to WSP is less than 1. In some embodiments, the ratio of WOP to WSP is in the range of about 0.4 to about 0.9.

In some embodiments, the occlusive portion is located more than 2 cm from the distal end of the device. In a more preferred embodiment, the occlusive portion is located on the proximal half of the stabilizing portion. Through human clinical testing, it was more difficult to obtain intravaginal rectal occlusion with the same posterior force application in the area of the perineal body than in the area proximal to the perineal body. This result was unanticipated because the rectal canal is narrower in the region of the perineal body. Users also felt greater discomfort when force was applied to the perineal body as compared to proximal to the perineal body. Locating the occluding portion at least 2 cm from the distal portion of the stabilizing body, and more preferably on the proximal half of the device, configures it to compress proximal to the perineal body.

In a preferred embodiment, the occlusive portion compresses the rectum greater than about 3 cm proximal to the introitus. This configuration allows the occlusive portion to press proximal to the perineal body.

Clinical testing revealed a range of pressures internal to the device and applied to the rectovaginal septum that were optimal for occluding the rectum in order to prevent stool leakage, while at the same time not causing discomfort or adverse events such as tissue necrosis. In some embodiments, the occlusive portion is inflated to a pressure of less than about 200 mmHg. In some embodiments, the occlusive portion is inflated to a pressure between about 40 mmHg and about 150 mmHg. In another exemplary embodiment, the occlusive portion is inflated to a pressure between 60 mmHg and 120 mmHg.

In some embodiments, the occlusive portion applies a pressure of less than 200 mmHg to the rectovaginal septum in an extended state. In a more preferred embodiment, the occlusive portion applies a pressure between about 40 mmHg and about 150 mmHg to the rectovaginal septum in an extended state. In some embodiments, the occlusive portion applies a pressure in the range of 60 mmHg to 120 mmHg to the rectovaginal septum in an extended state.

The occlusive portion preferably reaches the dimensions stated above at pressures of about 40-about 150 mmHg.

A preferred embodiment is sized and configured such that, when placed in-situ and inflated to a pressure between about 60-about 120 mmHg, the extension length ("EL") of the extended occlusive portion is at least 90% of its dimension when inflated ex-situ to the same pressure. That is, the stabilization of the device has not created additional tension in the vagina such that the occluding portion is inhibited by the rectovaginal septum from substantially reaching its full extension for a given pressure. This is important because increasing pressure when the occlusive portion is restrained by the anatomy from reaching full extension increases the force transferred to the rectovaginal septum, thereby putting additional strain on the tissue.

In a preferred embodiment, the occlusive portion extends at an angle of about 45-about 135 degrees from the substantially longitudinal axis of the stabilizing portion. More specifically, the stabilizing body forms a flat, planar surface that is 45-135 degrees from the direction of expansion of the occluding portion. This near-perpendicular angle allows maximum potential occlusion depth of an occluding member of a given size. This is important because the greater the distance travelled by the occluding member, the thinner the stabilizing portion has to be, which increases slack in the vaginal tissue for increased rectal occlusion and stability and allows for freer stool passage when not in an occluding state. Additionally, configuring the device with the angle of extension near perpendicular reduces the tendency for the device to translate inside the vagina upon expansion.

In a preferred embodiment, the ratio of the cross-sectional area of the occluding portion (taking the cross-sectional cut with a plane formed by the longitudinal and lateral axes) to the area within the perimeter of the stabilizing body is less than about 0.8. This allows the reaction force from the rectal occlusion to be distributed on a larger perimeter of tissue on the anterior side, increasing comfort.

In a preferred embodiment, the occlusive portion has a cross sectional area (taking the cross-sectional cut with a plane formed by the lateral and anterior-posterior axes) in the range from about 5.5 cm$^2$ to about 36 cm$^2$. In another exemplary embodiment, the occlusive portion has a cross sectional area (taking the cross-sectional cut with a plane formed by the lateral and anterior-posterior axes) in the range from about 6 cm$^2$ to about 25 cm$^2$.

In a preferred embodiment, the stabilizing body spans a cross sectional area (in the plane of the stabilizing body) in the range of about 12 cm$^2$-about 50 cm$^2$. One aspect of the disclosure is a method of applying a force, or pressing, on the recto-vaginal septum in an area that is about 12 cm$^2$-about 50 cm$^2$.

In a preferred embodiment, the volume of the device in an un-extended state is less than about 60% of the volume of the extended occluding portion.

The width, area or volume of the stabilizing portion can be reduced in proximity to the occluding portion in order to further make available the vaginal tissue to be utilized for rectal occlusion.

It should be noted that while preferred numerical ranges are provided herein, it may be possible to deviate outside of these ranges and compensate for the variation in other manners.

As shown in FIG. 47, the width of the stabilizing portion helps keep the stabilizing portion from pushing up into the anterior wall of the vagina when the occluding portion is extended.

A bulky intravaginal rectal occluder may not be as stable, and may take up too much volume, making it difficult to manipulate the vaginal tissue towards the rectum. It has been observed through testing that volume appears to be especially important proximal to the perineal body where the occluding portion is adapted to extend. The occluding portion should be sized and configured to allow at least some stool passage when non-extended. The prior art attempts have described devices that occupy volumes that are greater than the devices described herein One of the deficiencies in prior art attempts is that the occluding portions are also used to secure the device. It was discovered in Applicants' testing that an intra-vaginal device where securing relies on expansion is inherently unstable when the device is unexpanded. It was further discovered that when such devices transition from non-extended to extended states, their positioning and directionality is variable and unpredictable. This is especially problematic if the goal is to use the vaginal device to apply a directed force to the rectum. For one, if the device is inserted in an unextended state, it makes it difficult to reliably extend to apply a force in the right location. Additionally, throughout the course of use, patients may wish to deflate, but not remove, the device for defecation or other activities when they feel active bowel control is not needed. In these cases, as is the case initially, the instability upon deflation would make it difficult to re-extend in the right position. Prior art attempts fail to provide intra-vaginal stabilization that does not rely on expansion of the device.

Another drawback to the stability of prior art attempts is that some are tubular devices, more specifically defined as generally cylindrical. Applicants' testing has revealed that this type of shape does not stably rest in the vagina, especially if force is applied towards the recto-vaginal septum, as it tends to rotate within the vagina. The devices described herein do not suffer from this deficiency.

In addition to the dimensions described herein, in some embodiments the stabilizing portion has a planar configuration. Testing also revealed effective thickness relative to lateral span of the stabilizing portion to allow proper posterior expansion but at the same time provide for adequate stabilization. Some previous attempts in this area include devices with shapes that are generally 3-dimensional or cylindrical-type shapes. These shapes occupy a great deal of volume in the vagina, and don't lend themselves towards indexing in a given orientation.

As shown in FIG. 48A, the stabilizing portion is wider than it is thick. The width helps maintain orientation and the thickness provides a device that doesn't occupy too much volume, leaving the rectovaginal septum easier to manipulate.

A stabilizing portion that does not have a truly planar configuration can still provide sufficient stabilization. Embodiments below illustrate this concept. Those alternative embodiments, however, have lateral portions that stabilize against boney structure and can be stabilized at a location proximal to the two lateral stabilization locations. Additionally, in these alternative embodiments the stabilizing portion is wider than it is thick, particularly in the lateral portions where they are adapted to be stabilized by the boney pelvis structure. In addition, these alternative embodiments preferably don't occupy a relatively large volume over the perineal body when non-extended.

Another deficiency of prior art attempts is that they fail to describe an efficient force transfer from the vagina to the rectum. Applicants' experimentation has revealed the importance of the availability of redundant vaginal tissue to maintain force on the rectum. If a device is not designed to allow redundancy (or slack) in the vaginal wall in the area where the force is transmitted to the rectum, then the tension in the wall makes it difficult to transfer the force posteriorly towards the rectum. Prior art attempts fail to describe a device that provides sufficient slack.

The occluding portions of the devices herein are adapted to be reversibly extended to allow for reversible occlusion of the user's rectum to control the passage of stool. In some embodiments the occluding portion is adapted to be inflatable with a fluid such that it expands when the fluid is advanced into the occluding portion. In some embodiments the occluding portion can include an inflatable chamber in communication with an external fluid source adapted to fill the chamber with the fluid. For example, the occluding portion can comprise a chamber formed of a single layer of material, or the chamber can comprise more than one layer of material. In some embodiments one or more layers of the inflatable chamber can be an inelastic or an elastic material.

In some embodiments the stabilizing portion is also inflatable, and can be in fluid communication with the occluding portion or not. There can be a separate mechanism to inflate and deflate the stabilizing portion. If the stabilizing portion and occluding portion are in fluid communication, the stabilizing portion and the occluding portion can be filled with a line connected to the occluding portion or the stabilizing portion.

FIG. 49 illustrates an exemplary intra-vaginal device 300 adapted for the control of stool passage. Device 300 includes stabilizing portion 304 and occluding portion 302. Occluding portion 302 includes outer layer 308 and inner layer 310 disposed within outer layer 308. Inner layer 310 defines chamber 312. Fluid line 306 is in communication with chamber 312. Chamber 312 is not in fluid communication with the space outside of inner layer 310. In this embodiment inner layer 310 is not secured to outer layer 308, and as such the inner layer is "floating" within the outer layer. The layers can also be secured to each other. However, there are advantages to not securing the layers. One example is the ability of the layers to move with respect to each other. This is particularly important if the layers have different material properties such as elasticity, or are sized differently. When the two layers respond to inflation or deflation differently, it is helpful to allow motion between the two layers. For example, if the outer layer stretches with pressure, and the inner layer stretches less, the balloon structure formed by the combination of the two layers can still expand with pressure as long as the inner layer has sufficient folds to allow it to accommodate a larger volume as provided by the stretching of the outer layer. In this case, there will be at least some relative motion between the two layers.

It may be desirable to have an inner layer in the occluding portion, as in the embodiment in FIG. 49. If the fill media is air, or other gas, and the outer layer has a relatively high permeability rate to air or the gas, then the inflation chamber may not be able to maintain a desired pressure/volume for as long as desired without an inner layer. Rather than have the gas disposed directly within outer layer 308, inner layer 310, incorporated into the occluding portion 302, is disposed within outer layer 308, and the line 306 is in direct fluid communication with the inner chamber 312.

In an exemplary embodiment of manufacturing, the inner chamber can be formed by fusing two sheets of polyurethane together in a pattern, such as a circle, that will inflate to form a 3-dimensional shape when fluid is introduced between the layers, within the fused pattern. To this double-walled structure, a tube can be bonded by any typical means of adhesion or heat sealing, such that the tube allows the introduction of fluid between the fused layers. The double-walled inflatable portion (the inner chamber) can then be covered by the outer layer, by dip molding, coating, or by pre-forming an outer enclosure of the desired material (e.g. silicone) with at least a portion open to allow insertion of the inner chamber, inserting the inner chamber inside the outer enclosure, and sealing the outer enclosure so that the inner chamber is sealed within. Accommodation for the inflation tube can be created before or after the covering of the inner chamber with the outer chamber. In a preferred embodiment, this double-layered assembly can then be bonded to the stabilizing portion of the device by any typical means of adhesion.

Air is one option for the fill media and is a very convenient way for applying force. It is sanitary, and allows for some compliance, even with a non-compliant balloon material. In some embodiments one or more chambers in the occluding portion includes a silicone material. Silicone provides the following advantage for an intra-vaginal rectal occlude: it is soft, elastic, bio-compatible and has a long history of intra-vaginal use. Silicone is, however, very permeable to air, and a silicone chamber inflated with air could lose effectiveness when the user desires to keep an inflatable occluding portion extended. For example, in some cases a silicone chamber filled with air can lose effectiveness in about 4 hours, which may limit the utility of the device. The time in which it takes to lose effectiveness is, however, dependent of the thickness of the silicone material, the volume of air in the occluding portion, and other factors. The disclosure describes air within silicone, but materials other than silicone can have the same drawbacks when used with a variety of fill media. Incorporating an inner layer can be beneficial in a variety of material combinations.

In the embodiment of FIG. 49, air is the fill medium and is pumped into chamber 312 defined by inner layer 310. Outer layer 308 is a silicone material, which enables the tissue contacting portions of the device to maintain the exemplary advantages of being silicone. The fluid is, however, less permeable through inner layer 310 than outer layer 308. In this exemplary embodiment inner layer 310 is less permeable to air than the silicone outer layer 308. This allows the tissue contacting surfaces to be silicone (or other similar biocompatible material), but increases the length of time that the occluding portion can maintain pressure and volume.

In some embodiments the inner layer is thinner than the outer layer. The combined thickness and flexibility of the outer layer and the inner layer should result in a foldability for the occluding portion that is acceptable.

In some embodiments rather than incorporating an inner layer, the thickness of the outer layer can be increased to provide the device with a permeability that is acceptable.

In some embodiments the outer layer can be coated on the outer or inner surface to reduce the permeability of the layer. For example, a silicone material can be coated with parylene. If the outer layer has elastic characteristics, however, the coating may not stretch as much as the outer layer, which can result in gaps in the coating which renders the outer layer permeable. If the outer layer is a non-elastic or substantially non-elastic material, however, coating the layer may result with the desired permeability. Other potential ways to limit the expansion of the outer layer include, for example, using a material with a relatively high durometer, or incorporating scaffolding or other types of reinforcements into the outer layer.

Exemplary advantages of some of the devices herein are that the extendable member of the occluding portion is a soft, relatively elastic balloon, and is biocompatible. Providing an inner layer that is less permeable to air allows the outer layer to be a silicone material and have these desired characteristics.

One of the other characteristics of some of the occluding portions herein is that they are relatively compliant, which reduces the likelihood of trauma to the vaginal tissue, and allows some deformation when the patient may assume different positions (e.g., bearing down versus standing upright). In the exemplary embodiment shown in FIGS. 38A-F, the occluding portion includes an inner and outer layer as illustrated in FIG. 49. In a specific embodiment the extendable member, including the inner and outer layers, has a wall thickness between about 0.005"-0.040." Some of the compliance is achieved by having a relatively thin walled occluding portion. Some of the compliance is also achieved by the elasticity of at least one of layers of the occluding portion. Additionally, in this embodiment the fill medium is air, which is compressible. In a specific embodiment, the inner layer comprises a balloon (herein referred to as an "inner balloon") that is not in fluid communication with the space between the inner layer and the outer layer. The outer layer comprises a balloon (herein referred to as an "outer balloon") inside which is the inner balloon. This inner balloon has a potential volume larger than the nominal (neutral pressure) volume of the outer balloon. The compliance of the outer balloon therefore limits the expansion of the inner balloon. In this way, even if the inner balloon is of a relatively inelastic or non-compliant material, the combined configuration allows for overall compliance, provided by the elasticity or compliance of the outer balloon and the slack or excess material in the inner balloon. In a specific embodiment the inner layer is polyurethane, with a durometer of about 80 A, and a thickness of about 0.003". The outer layer is silicone, with a durometer of about 60 A, and a thickness of about 0.015".

In some embodiments the outer layer is a soft biocompatible elastomeric material. For example, the outer layer can be silicone with a durometer between about 30 and about 60 A, and have a thickness between about 0.005" and about 0.040". In some embodiments the inner layer is a low permeability polymer. For example, the inner layer can be polyurethane with a durometer between about 70 A and about 90 A, with a thickness between about 0.0005" and about 0.005". In these embodiments the occluding portion has a permeability rate of less than 0.5 cc air/hour/130 mmHg. The materials, thicknesses, and durometers can be varied to achieve the desired permeability rate.

An exemplary advantage of using materials with these characteristics is that the occluding portion is adapted to collapse upon deflation to a small size to allow stool to pass. Additionally, these characteristics aid in the insertion and removal of the device from the vagina.

FIG. 50 illustrates a portion of an exemplary device in which the device comprises an outer layer 319 with outer surface 320, and an inner layer 321 with outer surface 322. Intermediate layer 324 is disposed between the inner and outer layers. Intermediate layer can be a fluid (e.g., saline) or other material that is adapted to create a low friction interface between the inner layer and outer layer. For example, the intermediate layer could be a low viscosity polymer. Outer surface 320 can move with respect inner surface 322 since they are not coupled and because of the intermediate layer in between the two layers. FIG. 51 illustrates the portion of device disposed within a vagina adjacent cervix 316 and vaginal wall 318. Outer surface 320 does not move relative to the cervix, but rather it stays in place. Inner surface 322 does move, however, relative to outer surface 320. This allows the relative motion (rubbing) to occur between the layers where the fluid or low viscosity material is disposed. This prevents rubbing of the outer layer against the cervix and vaginal wall, which can minimize or prevent discomfort to the patient. Alternatively there can no material between outer layer 319 and inner layer 321; instead their surfaces have low enough friction to permit motion, or their surfaces are coated with at least one low friction coating.

The layered interface described above is also applicable to other vaginal devices that may rub against the vaginal wall from time to time.

An "extended configuration" as used herein is not limited to a preset extended configuration; "extended" is relative and refers to a configuration more expanded than a less expanded configuration.

FIGS. 52A-C illustrate an exemplary intra-vaginal device for the control of stool passage. Device 350 includes occluding portion 352 and stabilizing portion 354. Occluding portion 352 is described above with respect to any of the occluding portions and the mechanisms of extension. Stabilizing portion 354 includes stabilizing body 351. Stabilizing body 352 includes curved portion 359 (see FIG. 52B that follows the general curvature of the extended occluding portion 352. Stabilizing body 351 includes portion 353 wherein two sections of stabilizing body 351 are generally parallel to each other as they extend away from occluding portion 352. The stabilizing body then extends further laterally, forming lateral extension portions 355. Generally straight portion 357 couples the lateral portions 355. Additionally, as can be seen in FIG. 52B, stabilizing body curves upward in the transition from portions 353 to portions 355. FIG. 52B illustrates rectum 358, uterus 366, pubic symphysis 364, inferior pubic ramus 362, and vagina 360. FIG. 52B shows device 350 positioned in the vagina such that the stabilizing portion 354 stabilizes occluding portion 352 against the recto-vaginal septum above the perineal body, as is described above. FIG. 52B additionally shows another effect the device can have on the anatomy by which it may help a variety of bowel-related issues. What is referred to herein as compressing the rectum can also describe the modification of the ano-rectal angle. As shown in FIG. 52B, the extended device can push the rectum posteriorly which can have the effect of enhancing the angulation between the rectum and the anal canal (illustrated by the termination of 358). This ano-rectal angle is commonly associated with various bowel functions, such as continence and defecation. FIG. 52C illustrates a posterior view of FIG. 52B (showing only the device and a portion of the boney pelvis) illustrating lateral portions 355 of the stabilizing body extending further laterally than the boney inferior pubic 362. The upward curvature of stabilizing portion 354 can assist in stabilizing it against the boney structure of the pelvis.

The embodiment depicted in FIGS. 52 A-C, comprising a device body that is narrow for a longer longitudinal span of the device may be particularly advantageous in certain anatomies. For example, if a vagina is lacking in tissue slack or potential volume, maximum occlusion will be gained in conjunction with minimal distension of the lateral walls. This embodiment highlights the general concept of minimizing lateral displacement with the device in the vicinity of the occluding portion, but providing sufficient lateral breadth elsewhere on the device such that it can maintain an appropriate position in the vagina.

The embodiment pictured in 52A-C also comprises a curved profile (which is not necessarily in conjunction with the aforementioned narrow lateral span). This curved profile can help maintain an advantageous position with respect to the pubic arch. The pubic arch narrows as it approaches the pubic symphysis, so the closer to the pubic symphysis that a device can engage the pelvic anatomy to prevent expulsion, the more clearance the lateral extents of the stabilizing body will have on either side of the vaginal opening and pubic arch. This curve can also follow the natural curve of the pelvic floor or pelvic bones.

FIGS. 53A-F illustrate an exemplary torsion spring intra-vaginal device for the control of stool passage. FIG. 53A illustrates stabilizing member 370, including torsion spring 372 and first and second arms 374 and 376 extending from spring 372 (the rest of the device not shown for clarity). FIG. 53B illustrates the spring in an at-rest configuration. FIG. 53A illustrates arms 374 and 376 compressed by a user, such that the distance between the arms is decreased. The spring allows the stabilizing member to be compressed into a delivery configuration, and then it will revert to the deployed configuration shown in FIG. 53B. FIG. 53C illustrates a side view illustrating the arms curving up similarly to the lateral portions in FIGS. 52A-C. FIG. 53D illustrates a perspective view of the device, wherein stabilizing member is disposed within generally tubular stabilizing body 380. Spring 372 is disposed within cushioning member 382, which is secured to occluding portion 378. FIG. 53E is a top view of the device, with arms 374 and 376 compressed closer together. FIG. 53F is a top view showing the arms reverted to their at-rest configuration.

In general, the spring allows the anterior portion of the stabilizing portion to be able to accommodates different widths, and apply more consistent force by being flexible. When the spring is in an at-rest configuration and the arms are spread further apart, their lateral span is greater and thus they have a lateral span greater than the width of the boney structures described above. The arms can therefore be stabilized behind and against the inferior pubic ramus. Additionally, the spring device applies a lateral force against the vaginal walls, just behind the pubic arch. This can help the stabilizing portion anchor better against the vaginal tissue since it is always pushing laterally. Additionally, flexion in this direction may accommodate motion or slight misalignments better, as well as different anatomies.

FIG. 54 illustrates an exemplary torsion spring intra-vaginal device for the control of stool passage. Device 390 includes a stabilizing portion that includes spring 392 and arms 391 and 393 extending from the spring. The arms are spring loaded to apply a lateral force to the vaginal wall and so that they will be stabilized behind the boney structure of the pubic arch. The spring action ensures that the device is at the widest possible width that is appropriate for a given anatomy. The device also includes occluding portion 394. The device in this figure also has arms that have additional height, and preferably a convex surface providing a greater area of contact with the lateral wall.

Figure 55:
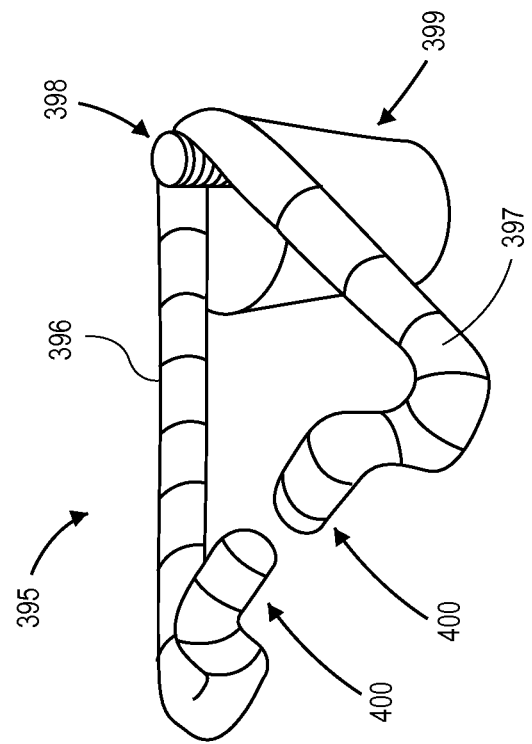

FIG. 55 illustrates an exemplary torsion spring intra-vaginal device for the control of stool passage. The device includes occluding portion 399. Stabilizing portion 395 includes spring 398 and spring-loaded arms 396 and 397. Both arms have end portions 400 that have a step. The end portions 400 can assist in the stabilizing above and behind the boney structure of the pubic arch.

FIG. 56 illustrates device 401 that includes occluding portion 402 and stabilizing portion 403. Stabilizing portion 403 includes body portion 404 with lateral extensions 405. Springs 406 are disposed within lateral portions 405. Lateral portions 405 are adapted to be stabilized behind the inferior pubic ramus, and springs 406 can accommodate a wider variety of movements and anatomies.

FIGS. 57A and 57B illustrate perspective and front views, respectively, of an exemplary stabilizing portion 410. Stabilizing portion 410 includes body 411 and two flaps 412 that can be deformed toward body 411 but are adapted to revert to the configuration shown in FIG. 57B. The flaps apply forces generally laterally and down to engage the boney inferior pubic ramus. The spring flaps also cause body 411 to be urged upwards towards the pubic symphysis.

In some embodiments the stabilizing portion has an adjustable lateral span to satisfy the anatomical needs of a specific patient. In some embodiments a sizing device can be used to measure one or more dimensions of a patient for the purpose of ordering or placing a specific or custom device. In some embodiments the device is adjustable and is adapted to inform the user of the appropriate dimensions for that particular patient.

It may be beneficial to have stabilizing portions with lengths, widths and/or curved configurations that are slightly different to accommodate the needs of individual patients. In addition, it may be beneficial to have occluding portions that have different lengths, widths, and/or compliances. The devices herein can be adapted such that one or more of these dimensions and characteristics are adjustable. Depending on the construction of the device, the adjustment mechanisms may be different, but the devices would be adjustable.

Some of the stabilizing portions herein are adapted to be secured above the boney structure of the pubic arch, such as the inferior pubic ramus. The stabilizing portion needs to have the appropriate width, or lateral span, so that it fits snugly behind the bone. If it is too narrow it will fall out; and if it is too wide it won't fit and can cause discomfort. A device with an adjustable width, particularly at the front (anterior) end can help ensure stable positioning.

FIG. 58 illustrates a device with an adjustable width, or lateral span. Stabilizing portion 420 includes body 421 with an anterior portion 422 and a posterior portion 423 that is adapted to be adjustable in the direction of the arrows. Body 421 could be a shape memory material that extends laterally upon the ambient (body) temperature being elevated. Once extended in the lateral direction they will be secured above the inferior pubic ramus. Body 421 could also be a deformable solid.

FIGS. 59A and 59B illustrate an exemplary stabilizing portion 430, which includes hub 433 to which arms 431 and 432 are secured and with respect to which the arms are adapted to rotate. The arms can be moved apart from one another such that the arms can be secured above and behind the inferior pubic ramus. The shape of the arms, or the stabilizing bodies, (in this embodiment and the other adjustable embodiments and spring-loaded stabilizing body embodiments described herein) can take many shapes in addition to what is shown here, including curves in the aforementioned stabilization plane, similar to the top-view profile in FIG. 37B, but not necessarily forming a continuous loop, so that sections can be moved relative to each other. These arms, or stabilizing bodies, can also have additional curvature out of this plane similar to the device described in FIG. 52B. Additionally, the cross-sectional profile of the arms can vary along their length to create appropriate radii of curvature that is appropriate to adapt to the vaginal wall. Furthermore, these arms can be made from, or covered by a soft biocompatible material that reduces trauma to the vaginal walls.

FIG. 60 illustrates an exemplary stabilizing portion 435 that includes a ratcheting mechanism that allows the arms to be ratcheted open to spread apart arms 438 and stabilize them in place.

FIGS. 61A-B illustrates an exemplary stabilizing portion 440 including body 441 that is adapted to deform about locations 442 and 443 so the device assumes the deformed configuration shown in FIG. 61A. For expansion, the location 443 can deform such that the lateral bending portions 442 extend further laterally to stabilize portion 440 in place.

FIGS. 62A and 62B illustrates an exemplary stabilizing portion 450 including a threaded joint 451. By rotating an actuation member, the distance between point A and B on body 451 is increased, and lateral portions 453 are widened.

FIGS. 63A and 63B illustrate an exemplary stabilizing portion 460 that includes first end 461 with ratcheting teeth, and a second end 462 with ratcheting teeth. The teeth are adapted to ratchet to widen the lateral span of the anterior portion.

FIGS. 64A and 64B illustrate an exemplary stabilizing portion that includes a hinge joint upon which arms 471 and 472 can be rotated. FIG. 64B illustrates an exploded view. A braking mechanism can be used to press the hinged joint together such that angular movement between the arms is minimized, in other words fixing the configuration of the device after it has been adjusted. In the exploded view, the 473 are shown in a non-braking orientation (i.e. not pressing the hinged joint together).

FIG. 65 illustrates an exemplary device 480 including occluding portion 481. Stabilizing portion 482 includes arms 483 that are adapted to pivot around pivot point 485. For delivery, the arms are moved closer towards one another in the direction of arrows. For deployment the arms are moved further apart to the configuration in FIG. 65. The arms have bulbous or rounded ends 484 to assist in anchoring the arms against the inferior pubic ramus. This embodiment is similar to the torsion spring embodiment, but the pivot point is moved closer to the anterior portion of the device. This pivot point can be, for example, spring-loaded, adjustable, or even freely pivoting. This embodiment includes a pivot point on a device that utilizes a central rod to span the distance between the occluding portion and the adjustable stabilizing arms.

In some embodiments the occluding portion includes an extension member that extends below and above the general plane of the stabilizing portion, at least where the stabilizing portion is secured to the occluding portion. FIGS. 66A and 66B illustrate an exemplary device 490 that includes stabilizing portion 491 occluding portion 493. Stabilizing portion also includes portion 492 of extendable member 494. Extendable member 494 is in this embodiment an inflatable material, and can comprise one or more layers. Portions 492 and 493 are part of the same chamber and thus are in fluid communication. They could also be two different chambers that are in fluid communication. It is also possible for the separate chambers to not be in fluid communication, wherein the chambers communicate with separate systems of valves and tubes. Finally, it is possible for the chambers to be reversibly in communication with each other via a valve or system of valves. Portion 492 acts similar to the cushioning members described above, but are part of the extendable member. Stabilizing portion 491 is disposed completely around the substantial middle of the posterior end of extendable member 494. In some embodiments the extendable member 494 is two section of elastic material that are secured together by a generally inelastic material around its middle. The stabilizing portion can be secured to the inelastic bridging material without interfering with the extension of the elastic material on either side of the inelastic material.

FIG. 67 illustrates an exemplary device 500 that includes stabilizing portion 501 and occluding portion 502. The stabilizing portion also includes extendable portion 503. Extendable member 504 forms a part of the occluding portion and a part of the stabilizing portion, even though the two portions are in fluid communication. Portion 503 is adapted to provide the benefits of the cushioning members described herein.

FIG. 68 illustrates an exemplary device 510 that includes stabilizing body 511 and occluding portion 512. Device 510 is similar to device 500, but the device also includes annular cushioning member 513 secured to extendable member 514. Cushioning member 531 better accommodates a cervix or other vaginal tissue and/or provides the device with an effectively flatter end.

The expandable members described above as extending below, at, or above the plane of the stabilizing body are shown in this disclosure attached to a stabilizing body of arbitrary shape. The characteristics of the expandable members described above are equally applicable to other stabilizing body structures contained or referenced herein.

In some embodiments the device is adapted such that the occluding portion extends away from the stabilizing portion but is in substantial alignment with the stabilizing portion. Exemplary device 530 shown in FIGS. 70A and 70B includes stabilizing portion 531 and occluding portion 532 in an extended configuration. Occluding portion 532 is secured to stabilizing portion 531 and when extended is in substantial alignment with stabilizing portion 531. The relative positions of the stabilizing portion and occluding portions may have some advantages in certain anatomies. This design can also limit torque applied around axis 533 by forces "F" on the expandable member as shown. Axis 533 extends from the anterior end of the device to the proximal end of the device. Axis 534 is shown and is generally orthogonal to axis 533. Force F shown acting on occluding portion 532 does not cause a rotation around the longitudinal axis 533. This design exemplifies the effect of shifting the alignment between the occluding portion and the stabilizing portion. In this embodiment the two portions are in substantial alignment, and thus the relative angle between this is substantially 180 degrees. The angle could be, in some embodiments, between about 90 degrees and 180 degrees depending on the degree to which rotation or translation is an issue.

In some instances intravaginal devices may be subject to a loss of stability and slip out of the vagina when a portion of the device is dislodged from the stabilization position behind the pubic arch, as described above. Undesired rotation about the devices longitudinal axis may be a contributing factor to the instability of the device.

FIG. 71 illustrates an exemplary device 542 in which the device is adapted such that occluding portion 541 is disposed at an angle greater than 90 degrees relative to stabilizing portion 542. FIG. 71 also illustrates how even though stabilizing portion 542 is not completely planar, occluding portion is considered to be disposed at an angle relative to a region of the stabilizing member directly adjacent occluding portion 541. For example, the anterior end of stabilizing portion curved upward relative to a region of the stabilizing portion disposed more posteriorly.

FIG. 72A illustrates stabilizing portion 551 stabilized in the pubic notch 550. In some instances, in response to a torque applied to the device, the stabilizing portion can be dislodged from its stabilized position, as is shown in FIG. 72B.

The stabilizing portion can take on a variety of configurations, some of which will not be described. FIGS. 73A-D illustrate an exemplary device 560 with stabilizing portion 561 and occluding portion 562. FIGS. 73A-D are perspective, side, front, and top views, respectively. Stabilizing portion 561 has an annular configuration and is not completely planar. However, the device shape is relatively flat in any given cross section along the device's length, and therefore meets the descriptions for stabilizing body width/length/thickness relationships described above. Stabilizing portion 561 includes first portion 564 and second portion 565 that is not in the plane generally defined by first portion 564. Line 563 is connected to occluding portion 562. This configuration may be able to stabilize the stabilizing portion better against bones in the pubic notch.

Stabilizing portions in which there is some flexibility built in can enhance the stability and comfort for the patient. For example, if a patient bears down, a device that can flex can be less likely to be become dislodged, the "give" in the device may allow the device to conform more to the anatomy without causing discomfort. A stabilizing body with more flexibility may have benefits over a stiffer device for stability. A flexible device lessens the transmission of a potentially dislodging force from one portion of the device to another. An exemplary material that can be incorporated into one or more portions of the device is ethylene vinyl acetate or other thermoplastics that has good elasticity and biocompatibility. Additionally, a flexible device may impart less tension on the vaginal walls, or impart less tension than can be overcome by the occluding portion force, so that rectal occlusion is not inhibited. The devices still preferable have enough strength and stiffness to keep the occluding portion in the right position against the recto-vaginal septum. For example, as the occluding portion extends, the occluding portion may try to push itself out of the vagina. Having some stiffness in the device therefore keeps the occluding back above the perineal body.

Figure 74B:
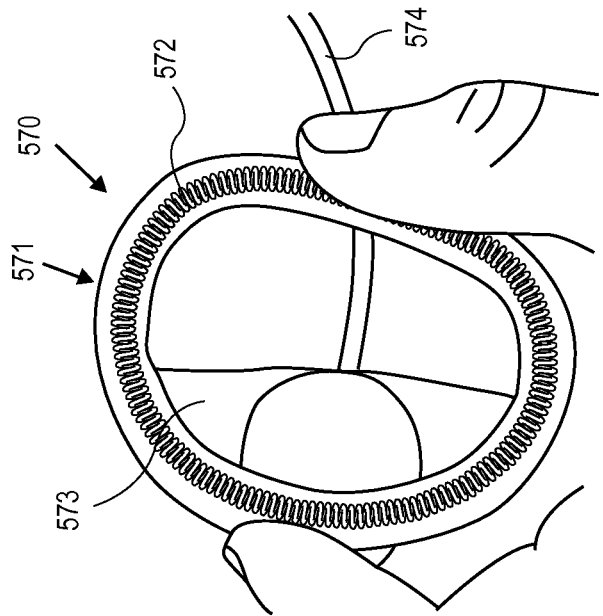
Figure 74A:
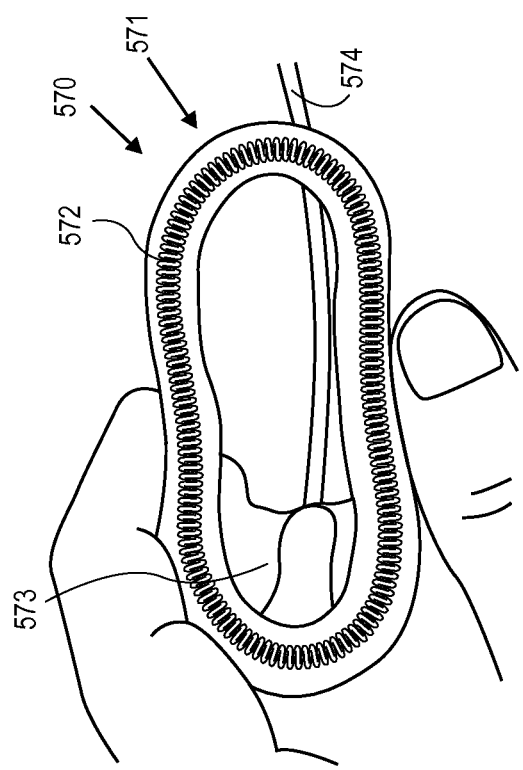
Figure 75B:
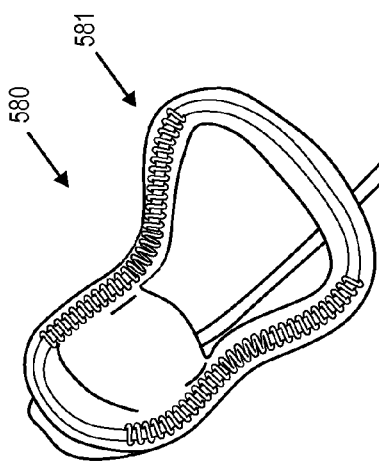
Figure 75E:
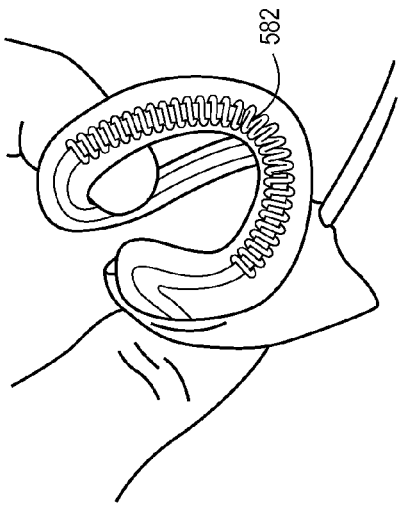
Figure 75D:
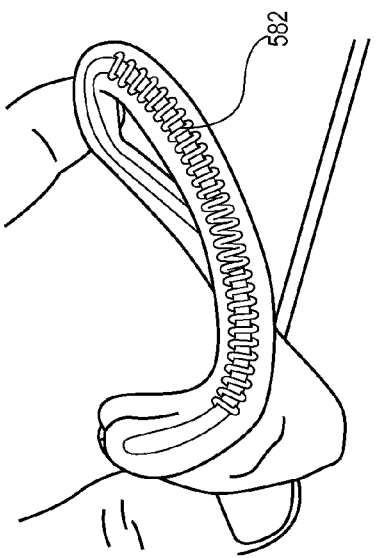
Figure 75A:
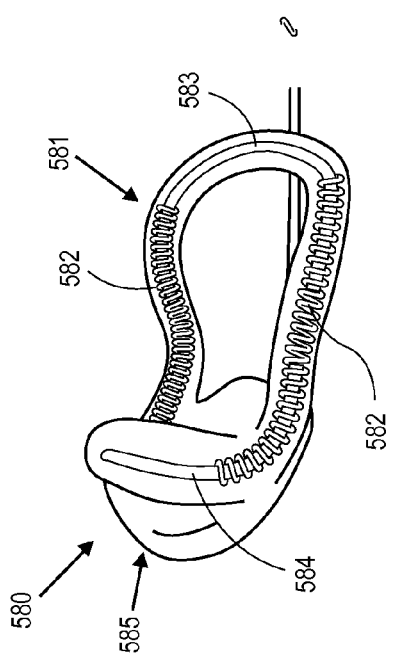
Figure 75C:
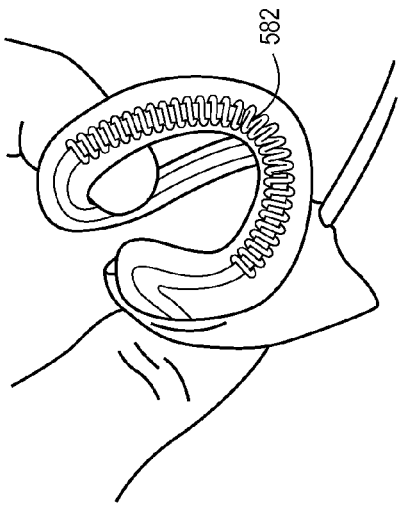

FIGS. 74A and B illustrate top views of an exemplary device 570 including stabilizing portion. Device 570 includes generally annular shaped stabilizing portion 571 and an occluding portion. FIG. 74A illustrates stabilizing portion 571 compressed along the longitudinal axis, illustrating the flexibility of the stabilizing portion. FIG. 74B illustrates the stabilizing portion compressed in an axis that is substantially orthogonal to the longitudinal axis of the device. Device 570 also includes securing member 573, to which the occluding portion is secured as is the stabilizing body. Stabilizing portion 571 includes a tubular stabilizing body, in which reinforcing member 572 is disposed. The tubular stabilizing body has a lumen extending therethrough adapted to house spring reinforcing member 572 therein. Reinforcing member 572 is in the form of a spring, similar to a portion of the reinforcing member in the embodiment in FIGS. 38A-F. The device shown in FIGS. 74A-B could also have a dedicated cushioning member as does the embodiment in FIGS. 38A-F.

FIGS. 75A-E illustrate an exemplary device 580 with a flexible stabilizing portion 581. The stabilizing portion includes a tubular body with spring 581 and 582 extending through the lateral portions of the tube to provide for anterior-to-posterior flexibility, which is illustrated in the difference between FIGS. 75D and 75E. Wireforms 583 and 585 are disposed at the anterior and posterior portions, respectively, and are secured to the springs. Device 580 also includes occluding portion 585. The anterior portion the stabilizing body extends upward relative to the posterior portion of the stabilizing portion.

Figure 76:
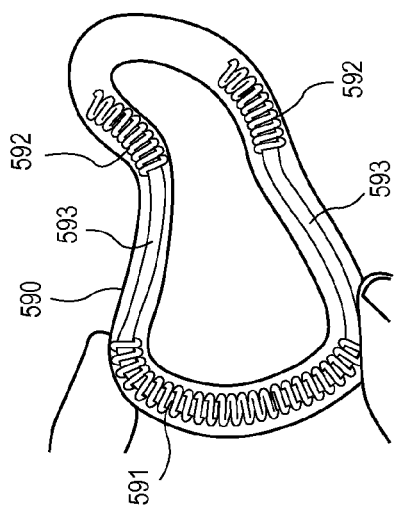

FIG. 76 illustrates exemplary stabilizing body 590 that has anterior spring 591 and lateral springs 592 therein. The springs are coupled by wireforms 593. The posterior portion of stabilizing body 590 does not have a reinforcing member therein, which provides for flexibility in that region. The anterior portion of the stabilizing body extends upwards.

Figure 77B:
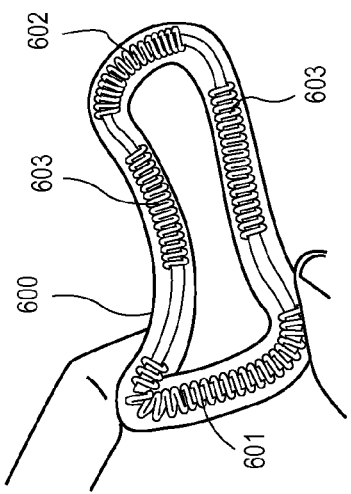
Figure 77A:
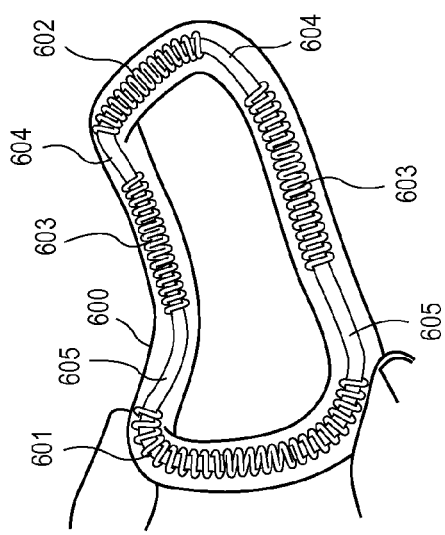

FIGS. 77A and 77B illustrate stabilizing body 600 that has anterior spring 601, posterior spring 602, and lateral springs 603 springs. The springs are coupled by wireforms 604 and 605. FIG. 77B illustrates the body being flexed along the longitudinal axis of the device. The anterior portion of the device extends upwards. A device with flexibility as shown in FIGS. 77A and 77B can also be flexed by bringing the lateral sides together, without necessarily folding the device as shown in FIGS. 44A-C.

Figure 78:
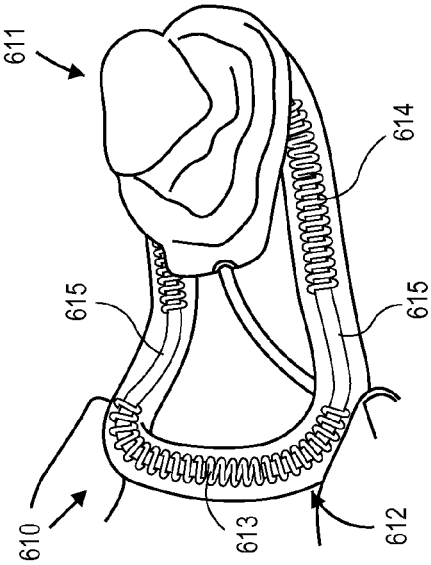

FIG. 78 illustrates exemplary device 610 wherein occluding portion 611 extends in the superior direction relative to the stabilizing body. Stabilizing portion 612 includes anterior spring 613 and lateral springs 614 (only one shown) disposed with a stabilizing body. The springs are coupled by wireforms 615. By extending in the superior direction, the stabilizing body itself applies the force to the rectum, thereby controlling the passage of stool. This embodiment additionally utilizes lateral springs to facilitate the deflection of the stabilizing body around the occluding portion, as it deflects towards the rectum.

Figure 79B:
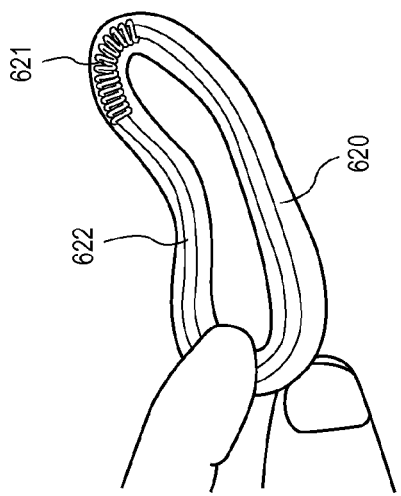
Figure 79A:
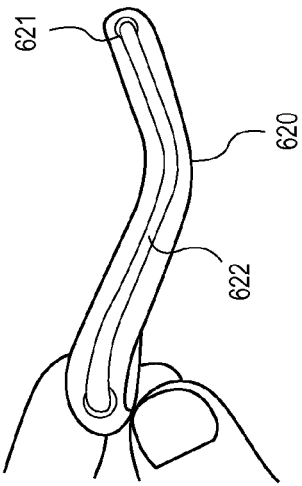

FIGS. 79A-B illustrate an exemplary stabilizing body 620, wherein a posterior spring 621 is disposed therein. Wireform 622 is disposed through the remainder of the stabilizing body, and is coupled to either end of spring 621. The stabilizing body has a configuration that is generally curved upwards in the anterior region.

Figure 80:
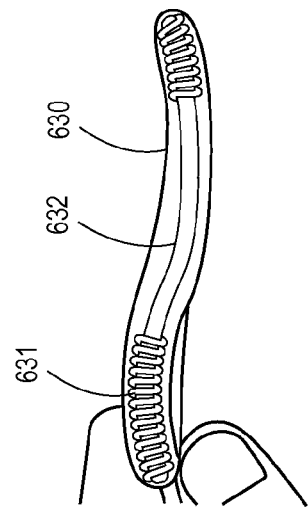
Figure 82A:
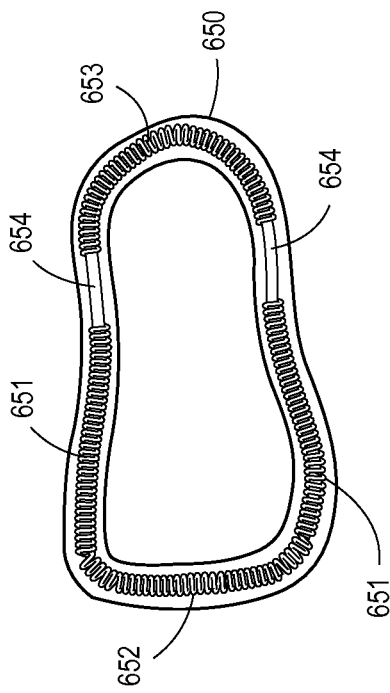
Figure 82B:
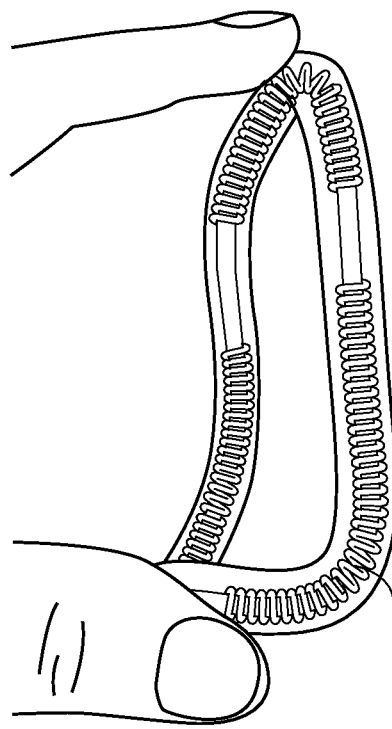
Figure 82C:
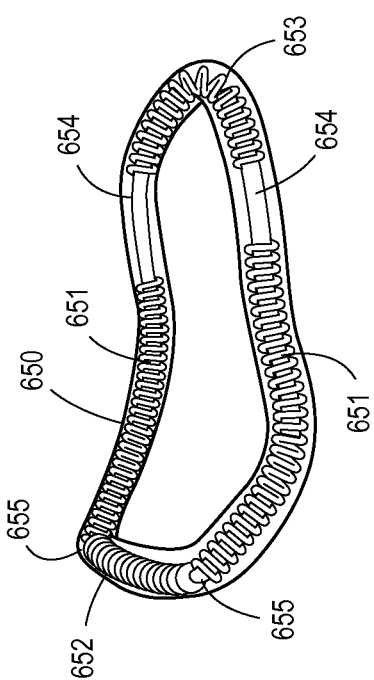
Figure 82D:
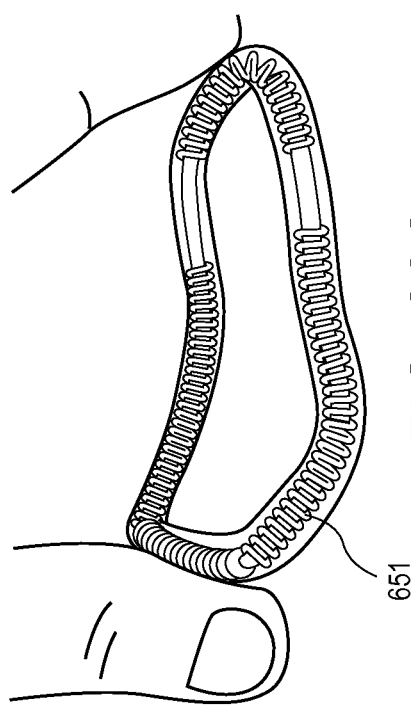

FIG. 80 illustrates exemplary stabilizing body 630 with a general S-curve configuration. Spring 631 and wireform 632 are disposed within body 630.

Figure 81B:
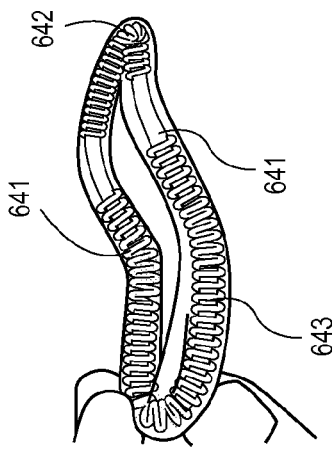
Figure 81A:
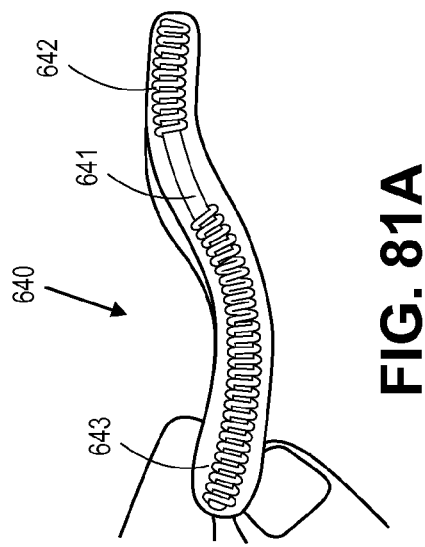

FIGS. 81A-B illustrate exemplary body 640 that has a general S-curve configuration. The reinforcing member includes lateral springs 641 and anterior spring 642. Wireforms couple the different spring sections.

FIGS. 82A-D illustrate an exemplary stabilizing body 650 that has a configuration in which the anterior portion is positioned upwards relative to the remainder of the body. The reinforcing member includes anterior spring 652, lateral springs 651, and posterior spring 653. The springs are coupled by the four wireforms 654 and 655. The springs provide for flexibility in the anterior to posterior direction, as well as foldability along the longitudinal axis, as is shown by the difference between FIGS. 82C and 82D.

Figure 83:
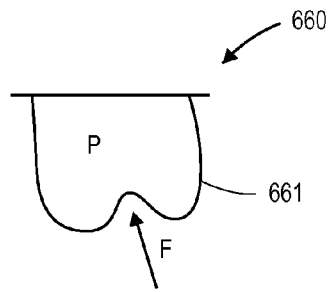
FIGS. 83-84 illustrate an exemplary occluding portion.
Figure 84:
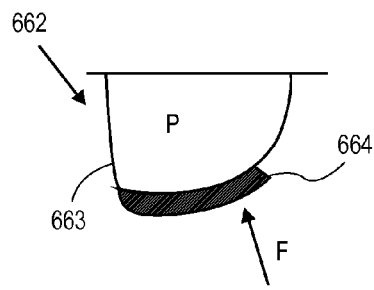

In some embodiments the occluding portion includes a force distributing feature to distribute the forces applied to the extendable member over a greater area of the extendable member. In use, when the occluding portion is extended, the septum tissue applies a force to the occluding member. In general, as an object pushes into a fixed-air-mass expandable structure, the "reaction pressure" is proportional to the area of the object/expandable structure interface. A narrow object will thus push in further in the expandable structure than a wide object to reach the same reaction pressure. FIG. 83 illustrate the concept in which occluding portion 660 includes expandable member 661, wherein force F is being applied by a relatively narrow object. FIG. 84 illustrates an exemplary occluding portion 662 including expandable member 663 and cap 664 secured to the expandable member 664. The cap material is stiffer than the expandable member material, and thus when force F is applied to the cap, the force applied to the expandable member is distributed over the interface between the cap and the expandable structure. The interface between the cap and the expandable member is greater than the interface would have been between the object and the expandable member. This can improve the extendable member's ability to apply a force against vaginal tissue to occlude the rectum in the presence of objects pressing against the force. The cap creates a more defined force-applying surface.

Figure 85A:
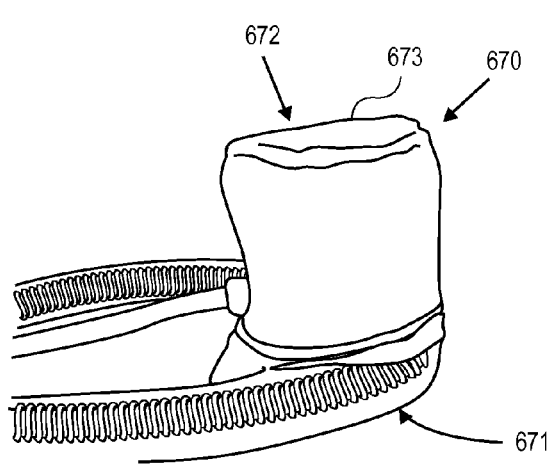
FIGS. 85A-85B illustrate an exemplary occluding portion.
Figure 85B:
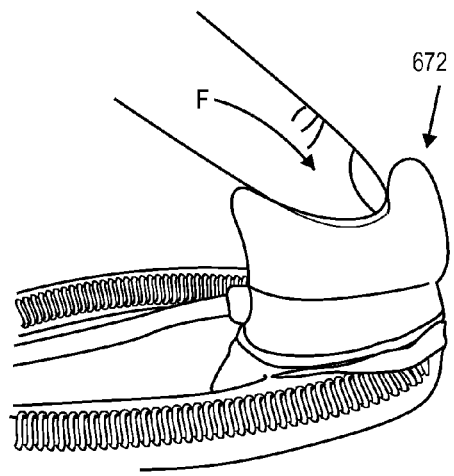
Figure 86A:
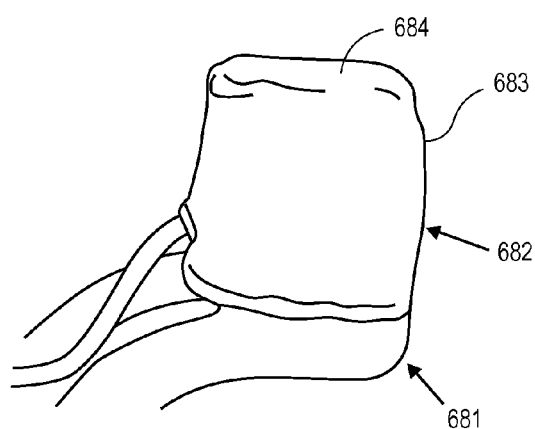
FIGS. 86A-86B illustrate an exemplary occluding portion.
Figure 86B:
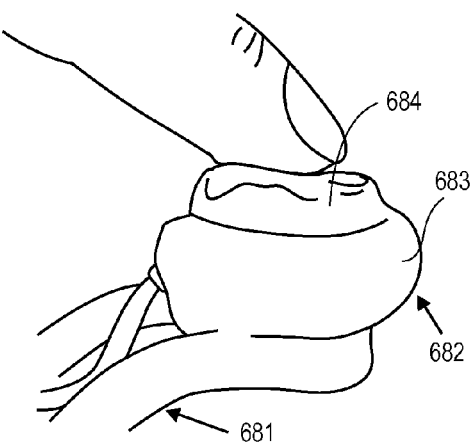

FIG. 85A illustrates exemplary device 670 including occluding portion 672 and stabilizing portion 671. Occluding portion 672 includes extendable member 673, upon which force F is applied in FIG. 85B. The extendable member is deformed, as is shown. The force is essentially localized at the location of application of the F. FIGS. 86A-B illustrate device 680 that includes stabilizing portion 681 and occluding portion 682. Occluding portion 682 includes extendable member 683 and cap 684. Cap 684 is a stiffer material than extendable member 683, which can be, for example, a soft silicone material or any other exemplary extendable member material as set forth herein. As shown in FIG. 86B, when a force is applied to cap 684, the force is distributed over the interface between extendable member 683 and cap 684. This results in a more well-defined force applying surface on the occluding portion.

In some embodiments the cap is the same material as the extendable member but has a thickness greater than thinner portions of the extendable material.

Figure 87A:
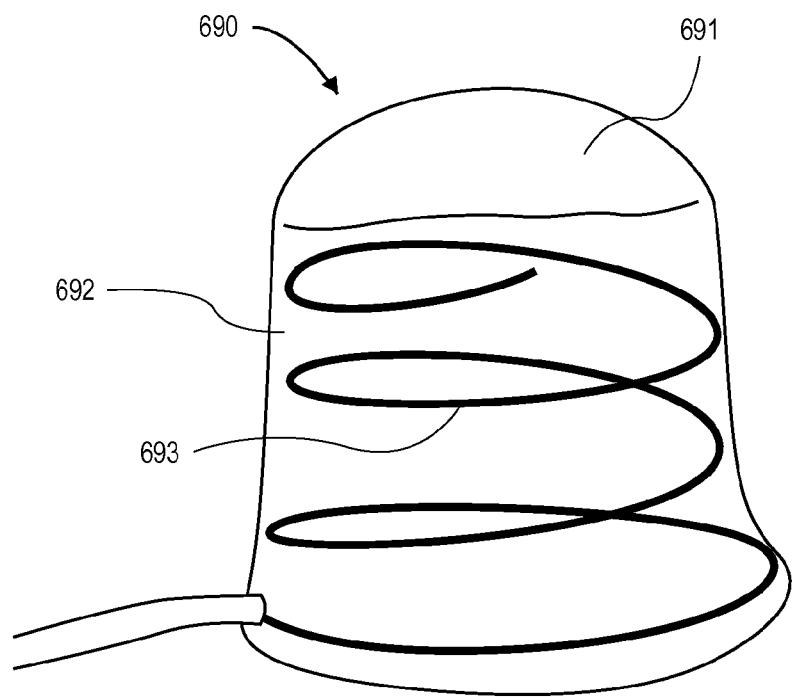
FIGS. 87A-87B illustrate an exemplary occluding portion.
Figure 87B:
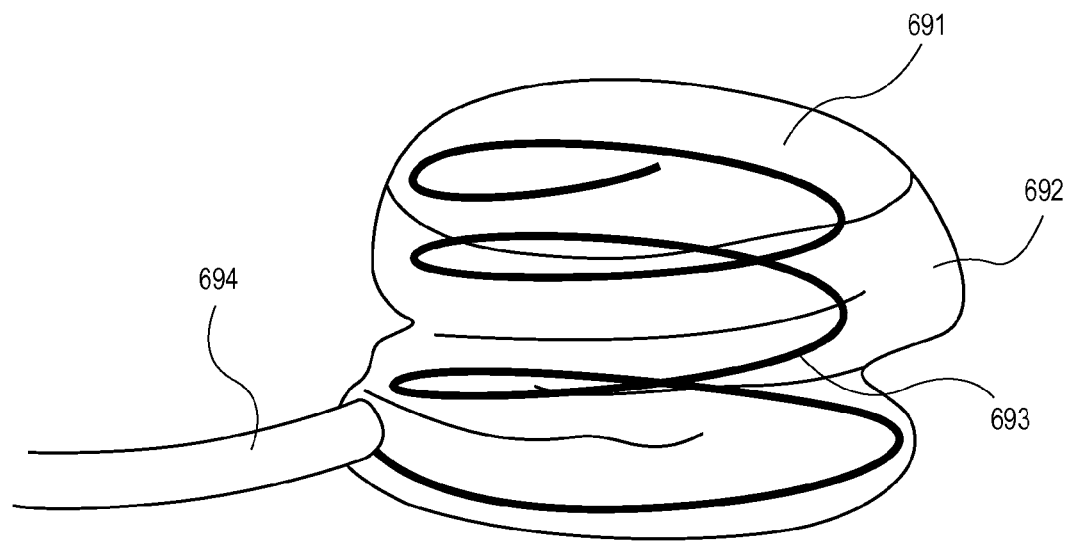

FIGS. 87A-B illustrate an exemplary occluding portion 690 that includes extendable member 692 and cap 691, which in this embodiment is a thickened portion of the same or substantially similar material as extendable member 692 material. For example, both the extendable member 692 and the cap can be made from a soft silicone, wherein the cap is a thickened region of the soft silicone. Occluding portion also includes spring 693 disposed within the chamber formed by extendable member 692 and cap 691. Extendable member 692 can have one or more layers as set forth herein. Cap 691 allows the spring to exert a force against the septum in a uniform manner over a larger surface. Tube 694 provides fluid communication between the occluding portion and a region outside the occluding portion. Tube 694 allows air to escape the occluding portion as it is compressed, which also deforms the spring as shown in FIG. 87B. Once compressed, the tube is closed, preventing air from returning to the occluding portion, and the spring remains compressed. The occluding portion can then be reinflated to allow the spring, and the occluding portion, to return to an extended state. The device can be inserted into the vaginal with the occluding portion in the non-extended state shown in FIG. 87B.

FIGS. 88A and 88B illustrate an exemplary device 700 that includes stabilizing portion 701 and occluding portion 702. Occluding portion 702 has spring 703 therein that applies a force to the recto-vaginal septum via the extendable member, or a cap as in the embodiment in FIGS. 87A-B. To compress the device from the extended state shown in FIG. 88A, a vacuum is pulled on the occluding portion via line 704 to remove the fluid (e.g., air) from the occluding portion. This causes spring 703 to compress to the configuration shown in FIG. 88B, and stool is allowed to pass out of the rectum. Fluid can be reintroduced into the occluding portion to inflate the occluding portion to an extended state, which allows the spring to revert to an extended state. In this embodiment the device is actively compressed to allow stool to pass.

A spring may be included in an occluding portion to help ensure that the extendable member collapses in a reproducible manner. Some extendible members can fold and collapse into a number of different configurations. It may be advantageous for the extendable member to return to the non-extended state in a substantially consistent manner each time. FIGS. 89A-B illustrate this concept. FIG. 89A shows exemplary occluding portion 710 including extendable member 711 and spring 712 therein. In the non-extended configuration shown in FIG. 89B, extendable member 711 collapses consistently to form plicated sections 713 of extendable member 711. An extendable member that collapses in a substantially consistent manner can make easier the determining of dimensions of the occluding portion in non-extended states.

FIGS. 90A-C illustrate an exemplary device 720 that includes occluding portion 722 and stabilizing portion 721. Stabilizing portion 721 includes a stabilizing body with a first portion 723 that has a substantially half-ring configuration, and a second portion with a generally linear configuration 724. The first portion 723 has an outer arc that subtends an angle of about 180 degrees. Occluding portion 722 extends posteriorly from the posterior end of the stabilizing manner. FIG. 90A is a top view, FIG. 90B is a perspective view, and FIG. 90C is a side view. In this embodiment stabilizing portion 721 can be sized and configured such that the proximal end of stabilizing portion 721 does or does not extend into the posterior formix. In embodiments in which it does not, the half-ring portion 723 and occluding portion 722 provide sufficient structural support to stabilize the device and maintain occluding portion against the septum in extended and non-extended states. Additionally, it may be possible with a device in this embodiment to reconfigure the occluding portion to a configuration between an extended state and a non-extended state such that the rectum is not occluded, yet the occluding portion is maintained in position due to, at least in part, forces applied to the septum from the partially extended occluding portion.

Figure 91:
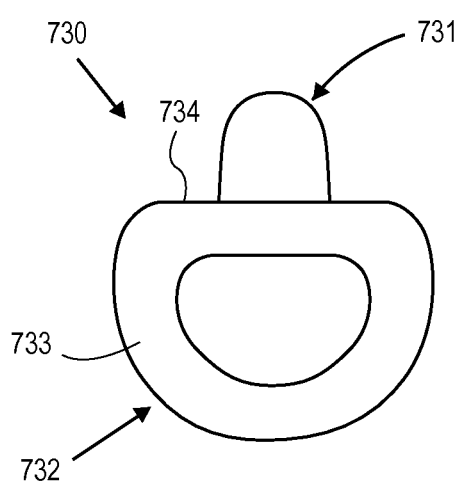
FIGS. 91 and 92 illustrate an exemplary intra-vaginal device for the control of stool passage.

FIG. 91 illustrate an exemplary device 730 whose stabilizing portion 732 is not a complete ring, but is more ring shaped than the embodiment in FIG. 90A-C. Portion 733 has an outer arc that subtends an angle greater than 180 degrees. The device includes occluding portion 731 and linear portion 734 of the stabilizing portion.

Figure 92:
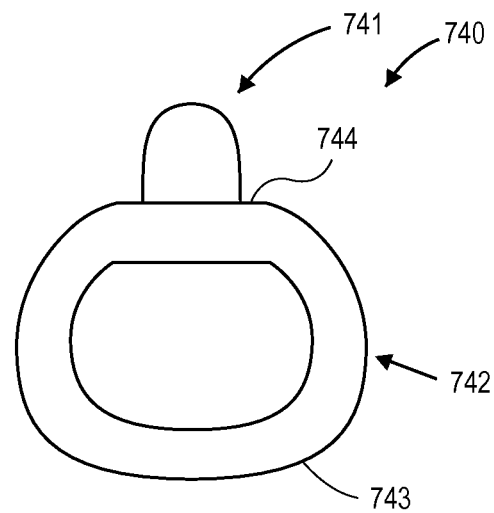

FIG. 92 illustrates an exemplary device 740 whose stabilizing portion 724 is not a complete ring but has a general ring configuration and more closely approximates a complete ring than the configuration of the stabilizing body in the embodiment in FIG. 91. First portion 743 of the stabilizing portion has an outer curve that subtends an angle between about 270 degrees. The device includes occluding portion 741 and linear portion 744 of the stabilizing portion.

In these embodiments the first portion can have an arc that subtends an angle between 180 and 360 degrees. In some embodiments the angle can be between about 90 and about 180 degrees.

Figure 93A:
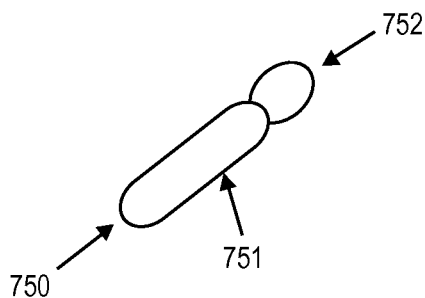
FIGS. 93A and 93B illustrate an exemplary intra-vaginal device for the control of stool passage.
Figure 93B:
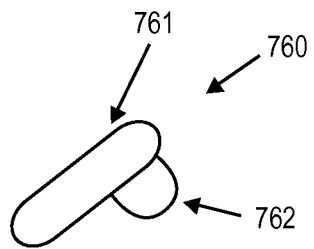

FIGS. 93A-B illustrate conceptually how device 750, which has a more superior and posterior occluding portion 752 relative to stabilizing portion 751 may be less effected by lateral tension than a similar device 760 that includes occluding portion 762 that is more inferior relative to stabilizing portion 761.

In some embodiments the occluding portion is adapted to be inflated and/or deflated using a fluid inflation device that is adapted to be disposed outside of the patient's vagina. FIG. 94 illustrates system 850 including stool control device 851 and inflation device 852. Device 851 can be any of the stool control devices herein. Device 851 includes inflation line 857 in fluid communication with occluding portion 858. The pump has a fluid inflow end 860 and an outflow end 855. Inflation device 852 also includes relief valve 853. Inflation device 852 includes pump 854 that, upon compression, pulls fluid from inflow end 860 and pumps it out of outflow end 855, in the direction of the arrows shown.

In an exemplary method of use, when the occluding portion is non-extended, the outflow end 855 is reversibly coupled to inflow end 859 of line 857, as shown in FIG. 95. The can be secured by a friction fit where outflow end 855 is sized to fit within inflow end 859. The connection could also include a luer lock or any other way to reversibly secure the two components. The pump is squeezed by the user and air is pumped from the inflow end 860 towards the occluding portion. Relief valve 853 is adapted to prevent over-pressurization. Including relief valve 853 allows the maximum allowed pressure for the occluding portion to be established at the relief pressure valve. If the pressure in the occluding portion exceeds the relief valve pressure, inflow air is diverted through the relief valve rather than being pumped into the occluding portion. The system can be modified such that there is an indication provided to user (e.g., an audible, visual, or tactile) when the air is being released from the relief valve. The user then knows to cease the pumping. Alternatively, the user can simply pump many times, knowing that the relief valve will prevent the occluding portion from overextension. Inflation device 852 can be easily held by the user to inflate the occluding portion. Once the occluding portion is adequately extended, inflation device 852 is decoupled from device 851.

Inflation device 852 is also used to pump fluid out of the occluding portion. FIG. 96 illustrates that to remove the fluid from occluding portion to move it to a non-extended state, inflation device 852 is again reversibly coupled to end of line 859, but inflow end 860 is secured to device end 859. The direction of flow in this orientation is shown in the direction of the arrow in the figure. The pump is repeatedly compressed by the user, which pumps air from the occluding portion and out outflow end 855. The user can compress the pump many times, known that after a few pumps essentially all of the fluid will be removed from the occluding portion and in a non-extended state. An indication (audible, visual or tactile) can also be provided to indicate when the occluding portion is in a sufficiently non-extended state.

At least one of the two ends of inflation device 852 can have an indicator associated with it to indicate to the user which end should be coupled to line 857 to inflate the occluding portion and which end should be coupled to line 857 to deflate the occluding portion. For example, in one embodiment one end has a color to indicate that it is the inflating end.

Figure 97:
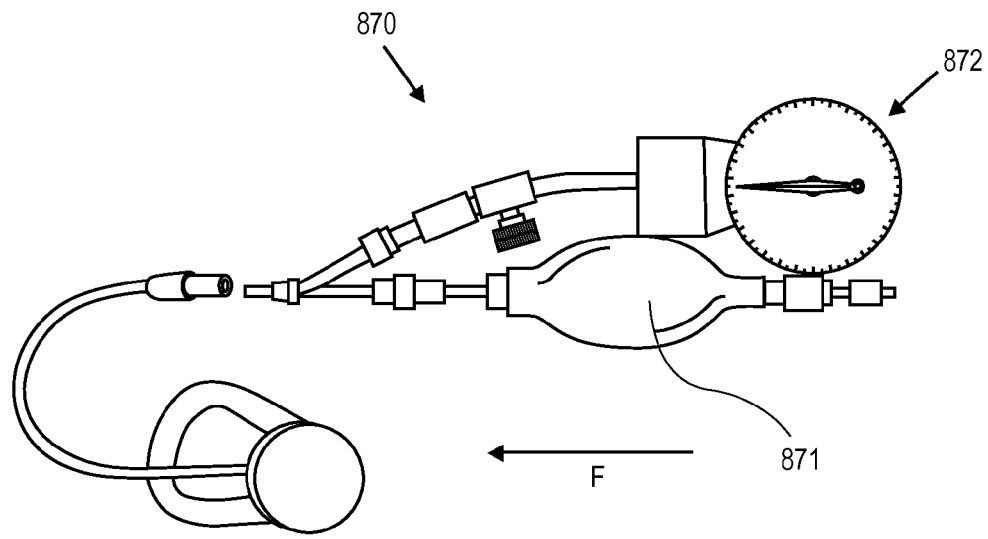
FIG. 97 illustrates an exemplary occlusion control device and its method of use.

In FIG. 97, exemplary inflation device 870 is reversibly secured to device 851, and includes pressure gauge 872 that is adapted to display the pressure within the occluding portion.

In some embodiments the inflation device includes an indicator to the user that the occluding portion has been inflated sufficiently to occlude the rectum, and/or that the occluding portion has been deflated sufficiently to allow stool to pass. In some embodiments there can be a visual indication, such as a green light to indicate passage (i.e., sufficient deflation) and a red light to indicate occlusion (sufficient inflation).

In some embodiments the pump is electronically controlled and does not require human compression. For example, in some embodiments the inflation device includes an electronically controlled pump that, upon turning on the device, pumps air through the line in one of two directions. The inflation device is coupled to the stool control device, and a user interface on the inflation device allows the user to depress a first button for inflation (flow into the device) or a second button for deflation (flow out of the device). There can also be a single trigger and a switch to indicate whether the trigger instigates inflation or deflation. The inflation device could be programmed to determine if the pressure in the occluding exceeded a maximum allowed pressure, which would result in the pump stopping. The inflation device could also be programmed to determine when the pressure was low enough that the occluding portion was sufficiently deflated, which would also result in the pump stopping. Alternatively, the power supplied to the pump can be regulated such that it can only move fluid across a pressure differential of a given magnitude, beyond which the inflation device fails to move more fluid.

In another embodiment, there is only one interface trigger and the inflation device has two connections, similar to the manual pump described above. For this embodiment, the inflation device can be connected to the stool control device via one fitting to inflate the device, and a second fitting to deflate the device.

One aspect of the disclosure is a system for the control of passage of stool, the system including an intra-vaginal device sized and configured to be inserted into an adult human user's vagina, wherein said device comprises an adjustably occlusive element adapted to reversibly apply a force that at least partially occludes the user's rectum, and an occlusion control mechanism that is adapted to control the amount of occlusion.

In some embodiments the occlusion control mechanism is adapted to adjust the amount of occlusion to an amount set by the user. The amount of occlusion can be controlled by a volume of fluid introduced into said occlusive element. The amount of occlusion can be controlled by a pressure of fluid introduced into said occlusive element. The amount of occlusion can be controlled by either a volume of fluid or a pressure of fluid present in the intra-vaginal device. The occlusion control mechanism can include a mechanism for limiting the pressure or volume of the fluid. The limiting mechanism can be adapted to vent fluid when the set amount of pressure or volume is present in the occlusive element. The occlusion control mechanism is adapted to remove fluid from the intra-vaginal device, thereby controlling the amount of occlusion.

In some embodiments the occlusion control mechanism controls the amount of occlusion by controlling the amount of force applied to the rectovaginal septum.

In some embodiments the occlusion control mechanism is adapted to provide the user with at least one indication of the amount of occlusion. The amount of occlusion can be controlled by a pressure of fluid within the occlusive element, and the indication can indicate the amount of pressure in the occlusive element.

One aspect of the disclosure is a method of use for an intravaginal rectal occlusion device, the method comprising inserting the intravaginal device into a user's vagina; coupling to the intravaginal device a device for controlling the amount of occlusion; actuating the controlling device to increase occlusion when passage of stool is not desired; and actuating the controlling device to decrease occlusion when passage of stool is desired. In some embodiments the increasing occlusion step includes the step of increasing the amount of fluid in the occlusion device until there is an excess of fluid and then allowing the excess of fluid to escape through at least one relief valve.

One aspect of the disclosure is a method for controlling the amount of rectal occlusion provided by an intravaginal device, the method comprising inserting the intravaginal device into a user's vagina; introducing fluid into the intravaginal device to extend the occlusive portion of the device; measuring the amount of extension of the occlusive portion; measuring the amount of occlusion of the user's rectum to determining an appropriate amount of occlusion; and configuring an occlusion control mechanism to repeatably extend the occlusive portion of the device to the amount of occlusion determined to be appropriate.

In some embodiments the step of measuring the amount of extension of the occlusive portion includes the step of measuring the pressure of the fluid in the intravaginal device. The measuring step can include using a pressure gauge or pressure transducer.

In some embodiments the step of measuring the amount of extension of the occlusive portion includes the step of measuring the volume of the fluid introduced into, or removed from, the intravaginal device.

In some embodiments measuring the amount of occlusion of the user's rectum includes the step of performing a rectal exam.

In some embodiments measuring the amount of occlusion of the user's rectum includes the step of visualizing the rectum via ultrasound.

In some embodiments the configuring step includes the step of adjusting a relief valve coupled to the occlusion control mechanism.

In some embodiments the configuring step includes the step of coupling a pre-set relief valve to the occlusion control mechanism.

In some embodiments the configuring step includes the step of adjusting a relief valve coupled to the intravaginal device.

In some embodiments the configuring step includes the step of coupling a pre-set relief valve to the intravaginal device.

In some embodiments measuring the amount of occlusion includes using anorectal manometry or defecography.

In some embodiments, the fluid in the occluding portion can be released through a fitting that allows for the natural release of the fluid rather than the fluid being pumped out. Some embodiments may comprise an elastic or spring member that facilitates collapse of the occluding portion, helping to force fluid out of the occluding portion.

Figure 98:
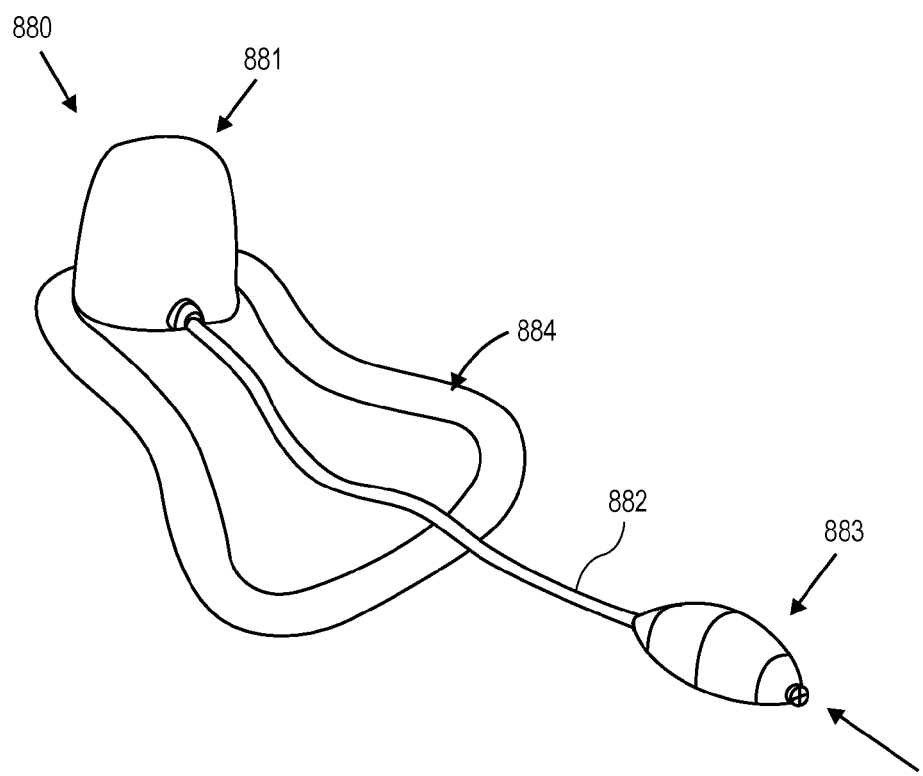
FIG. 98 illustrates an exemplary occlusion control device and its method of use.

FIG. 98 illustrate an exemplary stool control device 880 which includes occluding portion 881, stabilizing portion 884, fluid line 882, and finger pump 883. Finger pump 883 is sized such that it can be squeezed between two average adult fingers. Pump 883 is adapted to pump fluid in the direction of F. It may be beneficial to have the small pump 833 irreversibly fixed at the end of tube 882. This can alleviates the need to carry a larger pump. It can also allow for on-the-fly adjustment of the pressure or discrete periodic re-inflation. Pump 883 can also be adapted to be reversibly attached. Pump 883 can be reversed in direction to remove fluid from the occluding portion as well. Or a pump such as the pump in FIGS. 94-97 can be used when fluid is to be removed. Pump 883 can also be removed to allow for a pump such as in FIGS. 94-97 to inflate the occluding portion.

Figure 99:
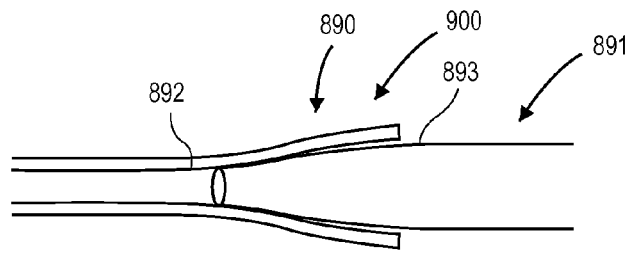
FIGS. 99 and 100A-B illustrate an exemplary way to release fluid from within an occluding portion.
Figure 100A:
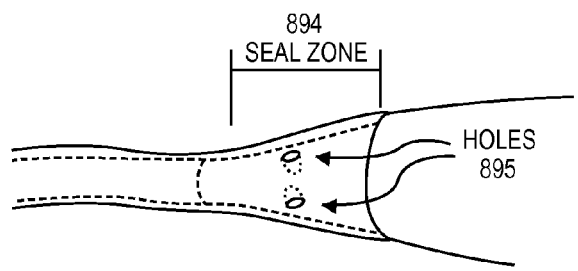
Figure 100B:
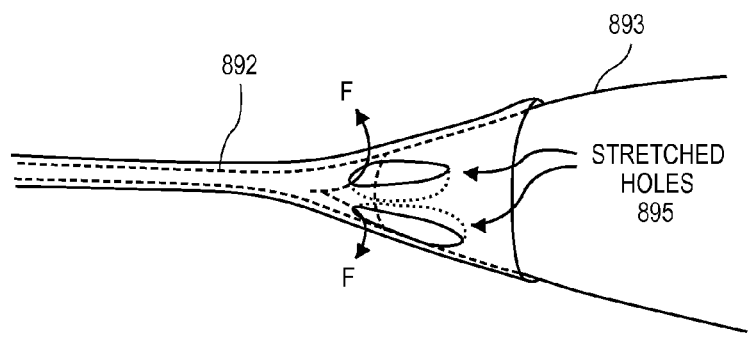

FIGS. 99 and 100A-B illustrate an additional way to release fluid (e.g., air) from within the occluding portion. It is more generally a way to release air from a tube. It could be particularly useful if the pump or valve does not have a way to release the air from the occluding portion. The device includes coupling 900 between line 890 and fitting 891 that is secured within the proximal end of line 890. The proximal end of fitting 893 is closed to ambient air. Coupling 900 can be used in the finger pump in FIG. 98, or it can simply be a fitting that is coupled to the inflation line that in fluid communication with the occluding portion. Fitting 891 can be considered a valve, a cap, nozzle, etc.

FIGS. 100A and 100B illustrate coupling 900 showing apertures 895 in the line 890 that all the way through line 890. Line 890 is an elastomeric material, or other type of material with similar properties. When it is fit over nozzle fitting 891, seal 894 (see FIG. 100A) is created between the inner diameter 892 of line 890 and the outer surface 893 of fitting 891. Due to the seal, air cannot escape from inside line 890 apertures 895. When tension is applied to fitting 891, as shown in FIG. 100B, line 890 is stretched, including apertures 895, as shown in FIG. 100B. When the distal end of fitting 891 clears at least a portion of the apertures, as shown in FIG. 100B, fluid is released from within line 890 out through the apertures 895 in the direction of arrows F.

A device similar to finger pump can act as the fitting, but rather than be squeezed to release air, it is tensioned as set forth above. This can allow for convenient and easy fluid release from the occluding portion.

An alternate embodiment may include a separate or integral valve that is manually operated to allow the release of fluid.

In some embodiments the device, or system components secured thereto (such as an externally disposed inflation control device), are adapted to control the amount of occlusion in the occluding portion. For example, in some embodiments the inflation device includes safety features (e.g., the relief valve described above) adapted to prevent over extension of the occluding portion. In some embodiments the system includes an adjustable interface mechanism that is pre-set to different extension amounts. For example, in some embodiments the interface has an adjustable setting that allows the user to select if they want to inflate or deflate the occluding portion. Once selected, the interface automatically inflates or deflates to pre-set limits. Alternatively, in some embodiments the interface has different levels of occlusion that can be selected. For example, the interface could be pre-set with completely occluded, half-occluded, and minimally occluded settings. The user can select which they desire, and the system will automatically fill the occluding portion to a pre-set limit. Alternatively, once the user selects the desired level of occlusion, the user then manually inflates the occluding portion but the interface prevents the user from inflating the occluding portion more than the pre-set limit.

In some embodiments an interface mechanism includes an indicator that is adapted to alert the user (e.g., audio, visual, tactile) when the device is at a certain level of expansion. For example, the interface can be adapted to indicate to the user when the occluding portion is fully extended, or completely non-extended. The interface mechanism may also alert the user if the occlusion has fallen over time to a level below a certain threshold.

In some embodiments the system includes a display adapted to display at least one value related to the degree of occlusion (e.g., a pressure gauge, a volume meter, a displacement gauge, etc.).

The system can also be tailored to the comfort level of a particular patient. A volume of the occluding portion, pressure, length of extension, or other parameter, that produces an optimum combination of occlusion and patient comfort can be tailored determined and programed into the system. In some instances an initial "fitting" takes place which includes a digital rectal exam. For example, as the occluding portion is extended, the pressure, volume or length is displayed or otherwise made available for the user or physician. The control device is then programmed or otherwise adapted to repeatedly extend the device to one or more of these settings. Ultrasound or other imaging techniques can also be used to determine occlusion, as can balloons and manometers.

In some uses a fitting tool is used to size the patient's vaginal dimensions to help select the right size for the device, or for individual portions or components of the device. The fitting tool can be expandable device that is inserted into the vaginal vault in an unexpanded configuration, and is then expanded inside the vagina.

Figure 101:
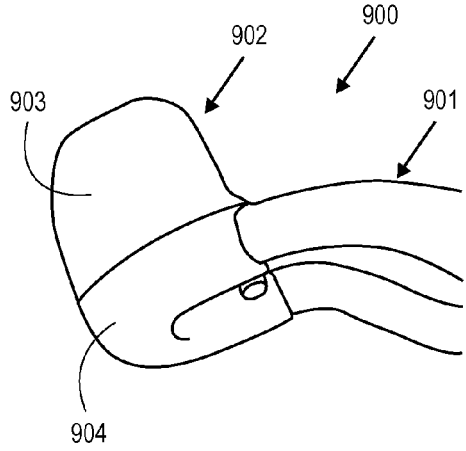
FIGS. 101-103 illustrate an exemplary modular device.
Figure 102:
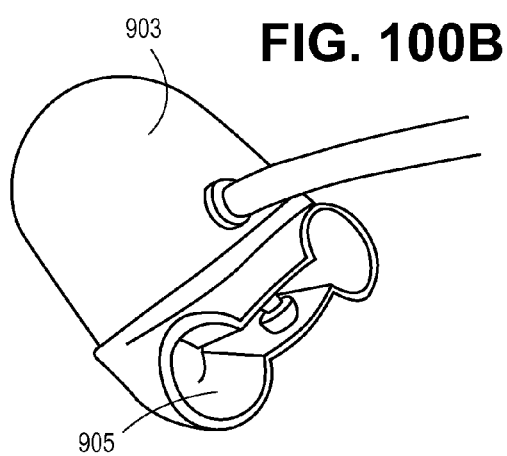
Figure 103:
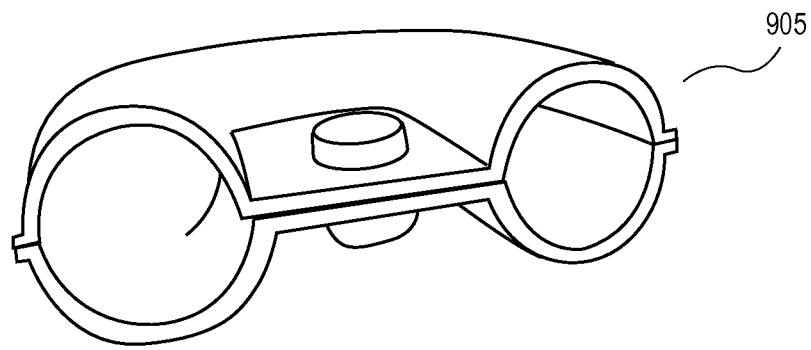

FIGS. 101-103 illustrate an exemplary modular design for an intra-vaginal stool control device. Modular designs can be used to interchange components of the device. For example, a variety of occluding portion can be coupled to a variety of stabilizing portions to find the best fit for a patient. For example, a balloon that fits most optimally for a given patient can be combined with a stabilizing body that fits optimally for that patient. In addition, a modular design allows for the replacement of a component that needs to be replaced, such as when an occluding portion wears out and needs to be replaced. Because the devices are so easily removed from the vagina, modular designs make is easy to replace only a portion of the device.

There may be kit of occluding portions with different dimensions (e.g., width, height) and a kit of stabilizing portions with different dimensions or shapes (e.g., width, length), and an optical selection of two components can be made.

FIG. 101 illustrates device 900 including stabilizing portion 901 that is controllably detached from occluding portion 902. Occluding portion 902 includes extendable member 903, button 904, and sleeve 905, which that is adapted to open to allow the release of stabilizing portion 901.

One aspect of the disclosure includes rectal occlusion devices that are passive in that they do not require external actuation to allow stool to pass. The devices include an occluding member that has a pre-set amount of strength (e.g., pressure, spring force, etc.). The strength amount prevents small amounts of stool from passing. However, when sufficient stool pressure is generated against the passive occluding member, the occluding member is deformed out of an occluding position and the stool forces its way past the occlusion and is expelled.

Alternatively, a device, static or not, can be utilized by the user in conjunction with her control over various muscles in her pelvis and abdomen. In this use embodiment, the device can prevent the passage of stool until the user changes her musculature (relaxes or tightens) in a way that then allows the device to be deflected by the stool. Similarly, a device, static or passively extendable, meeting the general requirements related to dimensions, geometrical configurations and protective elements established herein may apply sufficient force to prevent the passage of unwanted stool, but when sufficient stool is present, or sufficient defecatory reflexes are triggered in the user's bowel, stool is allowed to pass by either passing around the occlusive portion or displacing the occlusive portion (and possibly the entire device) temporarily to a different position as the stool passes. In this embodiment, extension control mechanisms such as inflation tubing need not be necessary.

Figure 104A:
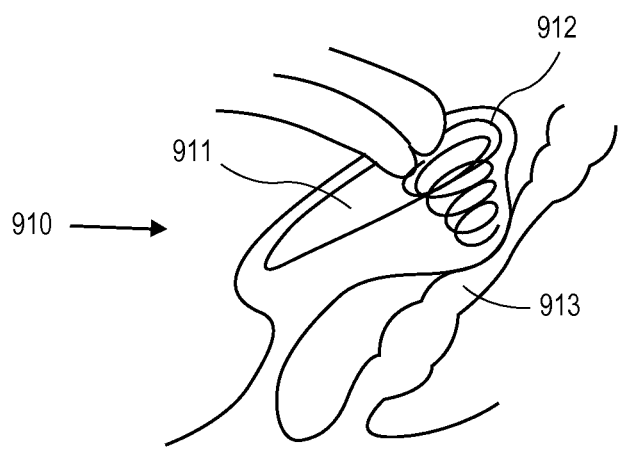
FIGS. 104A-B illustrate an exemplary passive occluding device.
Figure 104B:
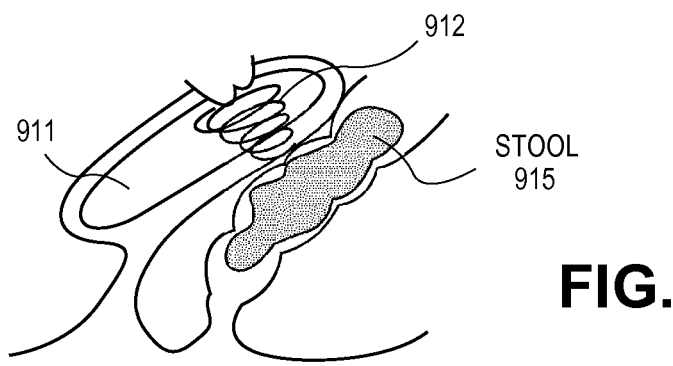

FIG. 104A illustrates passive occluding device 910 that includes stabilizing portion 911 and passive occluding member 912. Passive occluding member 912 is in a fully extended state in FIG. 104A and is occluding rectum 103. Alternatively, the occluding portion could also include an extendable member surrounding spring 912 like in the embodiment in FIGS. 87A-B. In FIG. 104B, when stool 916 has enough mass, it compresses the spring away from the rectum, allowing the stool to pass. Once the stool passes, the spring extends back towards an at-rest configuration and again occludes the rectum.

In alternative embodiment the passive occluding portion could be adapted to deflect in the inferior direction rather than being compressed. For example, the spring could be forced towards the stabilizing portion rather than being compressed.

In some embodiments the device or system includes a stool sensing device. In general, the stool sensing device notifies the patient if there is stool that needs to be evacuated. Some patients may have decreased sensation in their rectum as a result of the conditions that also lead to FI. Alternately, the device may prohibit stool from building up in an area of the rectum that is sensitive to filling. In either case, the user may not be able to determine, at least for sure, if there is accumulated stood that needs to be evacuated. In these situations it could be helpful to notify the user when stool is present and needs to be evacuated.

FIGS. 105A-B illustrate exemplary device 920 that includes pressure gauge 925. Device 920 also includes stabilizing portion 921 and occluding portion 922. Pressure gauge 925 is coupled to fluid line 924. When the stool mass is small (FIG. 105A), there is little pressure on the occluding portion and the pressure gauge gives a low reading. When the stool mass increases (FIG. 105B), the mass applies greater pressure to occluding portion 922, which results in a higher gauge reading. The pressure sensing mechanism is connected to an alarm, a visual display, or a tactile indicator. FIGS. 106A-B illustrate an exemplary tactile indicator 930, which is in fluid communication with occluding portion 922 via line 931. Indicator balloon 930 increases in size as pressure increases in the occluding portion and more fluid is driven to the indicating balloon.

When the device includes a stool sensing device, the sensing device can be sensitive to pressure from the body if the user assumes certain positions, such as bearing down, even though there may not be any stool in the rectum. To eliminate high pressure reading from body movement, a spring or other damping mechanism can be incorporated into the device to reduce pressure changes based on body movements. Alternatively, an electrical interface can be used and programed to distinguish between pressure increases due to stool versus pressure increases from changing body positions.

One aspect of the disclosure is a stool control device that utilizes two magnets to bring regions of tissue together to occlude the rectum. A magnetic force is created between a pole positioned in the vagina and a pole in the rectum to create the occlusive force.

FIG. 107A illustrates an intravaginal device 940 that includes a body 941 and a magnet 942 secured thereto. A second magnet 943 is positioned posterior to the rectal lumen. The magnet is shown implanted in this location, but the magnet can be disposed there using a sling (see FIG. 110). Device 940 is inserted into vaginal vault 944, and the magnetic attraction between the magnets urges the walls of the rectum together, occluding the rectum, as is shown in FIG. 107B.

FIG. 108 illustrates intra-vaginal magnetic device 950 with handling string 951 attached thereto for easy handling and removal from the vagina. FIG. 109 illustrates diaphragm-like device 961 with magnet 962 secured thereto.

To allow stool to pass, the magnetic attraction can be disrupted mechanically, or by electromagnetic control. Or, in some instances, it can be displaced by a sufficient amount of stool or pressure. The size of the magnets can be modified to control the amount of desired magnetic force. Cushioning elements can surround the magnets to prevent erosion when opposite walls are held together.

FIG. 110 illustrates an alternative way to secure the second magnet in place. Sling 971 with magnetic portion 970 secured thereon is wrapped around the rectum with the magnetic portion 970 in place as shown in FIG. 110. The pubic symphsis 974, anal canal 973, and coccyx 972 are shown.

Potential benefits of increasing the contact surface between the occluding and adjacent material in response to a force on the occluding portion can similarly apply to the stabilizing portion and how it is stabilized against boney tissue. FIG. 111A is a side view of exemplary device stabilizing portion 980 that includes anterior portion 982 and posterior portion 981. Anterior portion 982 and lateral portions are stabilized proximal to the pubic notch as set forth above. Anterior portion 982 has maximum thickness T1 that is greater than a maximum thickness T2 of posterior portion 981. The increased thickness in the anterior portion increases the interface area between anterior portion 982 and the vagina in the area of the pubic notch. The forces applied by anterior portion 982 on the vagina in that area are distributed over a larger surface area than they would be if anterior portion 982 had the same thickness as posterior portion 981.

FIG. 111B illustrates exemplary stabilizing portion 990 that includes anterior portion 992 and posterior portion 991 that substantially equal thicknesses T1 and T2, respectively.

FIG. 112 illustrates an exemplary stabilizing portion 1000 that includes a distal end 1001 that extends upwards relative to proximal end 102 to help stabilize it relative to boney structure 1003.

One or more components of the device can be made from a shape memory material that is adapted to revert to a shape memory configuration upon being heated above the materials transition temperature (the material can also have superelastic properties as well). For example, the stabilizing member can be adapted to revert to a stabilizing configuration from a delivery configuration when elevated towards body temperature. In some embodiments one or more components becomes more or less rigid when exposed to body temperature compared to room temperature or other temperature less than body temperature. For example, the stabilizing portion could have one or more shape memory material therein that are adapted to become more or less rigid when exposed to the body temperature.

Figures 113A, 113B, 113C:
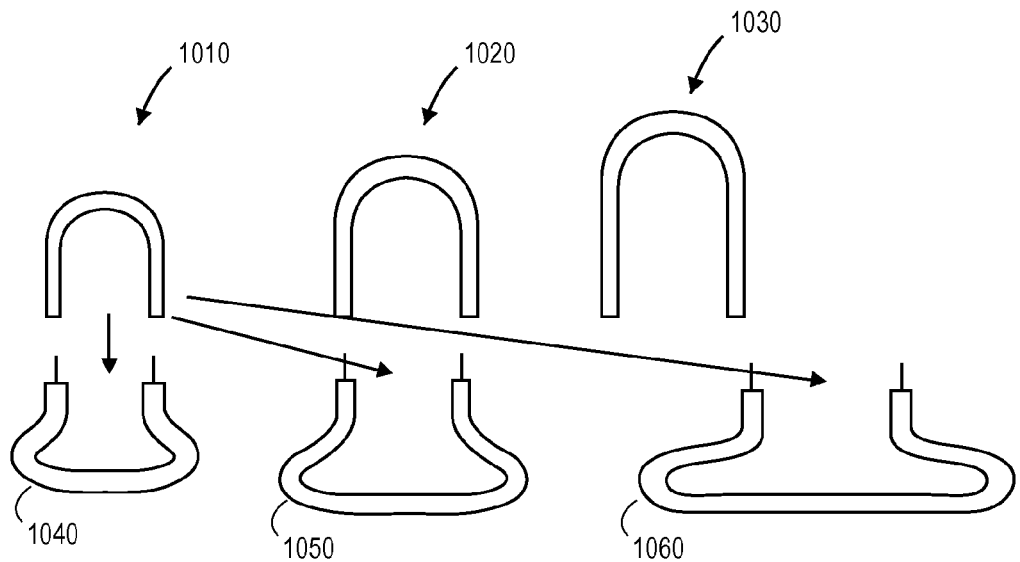
FIGS. 113A-C illustrate exemplary modular designs.

FIGS. 113A-C illustrate how the stabilizing portion can have two (or more) modular components that be disengaged from one another and secured to other components. In this embodiment there are three possible posterior portions 1010, 1020, and 1030, any one of which can be combined with any one of the three possible anterior portions 1040, 1050, and 1060. This allows for the mixing and matching of anterior and posterior portions of the stabilizing body, which allows for a greater variety of possible width, length, and thickness combinations. This can assist in obtaining a device fit optimized for a particular patient. There can be a kit of any possible number of anterior portions and posterior portions that can be selected from. The length of members 1010, 1020, and 1030 increases, respectively, from member 1010 to member 1030. The widths are shown to vary slightly. The width of members 1040, 1050, and 1060 increases, respectively, from member 1040 to member 1060. Any of these members can be adapted to mate with a modular occluding portion, examples of which are set forth herein.

Figure 114:
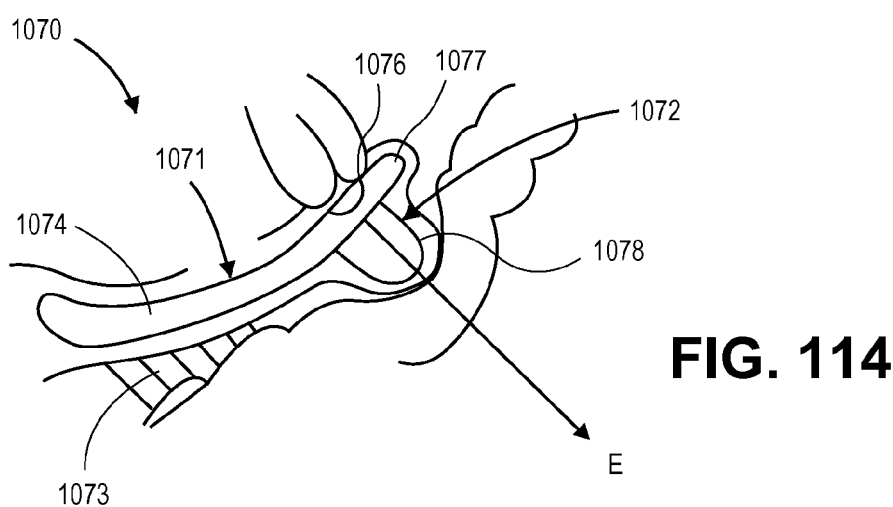
FIG. 114 illustrates an exemplary intra-vaginal device for controlling stool.

FIG. 114 illustrates an exemplary intravaginal device 1070 for controlling stool. The posterior end 1078 of occluding portion 1072 is slightly offset from the posterior end of stabilizing portion 1071. Specifically, the posterior end of stabilizing body 1074 extends further posteriorly than the posterior end of extendable member 1078. Stabilizing portion 1071 is sized and configured to stabilize occluding portion 1072 in the area of the pubic notch as set forth above. Stabilizing body 1074 extends upwards towards the anterior end of the body. Stabilizing portion 1071 includes optional cushioning member 1076, examples of which are provided herein. When the extendable member 1078 is extended, cushioning member 1076 (or simply the properties of the stabilizing portion in that area) prevent trauma to the anterior portion of the vagina in the posterior end of the vaginal vault. Cushioning member 1076 is disposed substantially opposite to the direction of extension of occluding portion, designated generally as direction "E" in FIG. 114.

Figure 115:
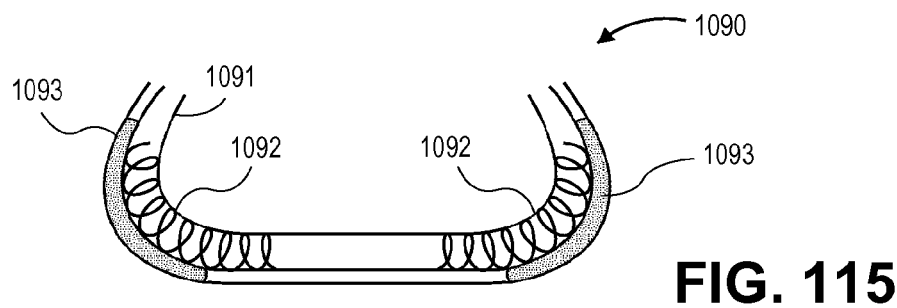
FIG. 115 illustrate a portion of an exemplary stabilizing portion.

FIG. 115 illustrate a top view of an anterior portion of exemplary stabilizing portion 1090. Stabilizing portion 1090 includes body 1091 with springs 1092 disposed therein. The stabilizing portion also includes bumpers 1093 on an outer portion of the body 1091. Bumpers could be separate components secured to body 1091. In some embodiments they are a polymeric material melted to body 1091 using a heat shrink tubing technique. Bumpers could be the same material as body 1091, but are a thickened portion of body 1091. In these cases bumpers can be considered part of body 1091. Bumpers 1093 can also be incorporated in embodiments in which the stabilizing portion does not have a stabilizing member therein. In this embodiment bumpers have a length that is about the same as the length of springs 1092, although the bumpers can be shorter or longer.

The bumpers can reduce the forces applied from the springs onto vaginal tissue, and can thus minimize trauma to vaginal tissue. Also, if bumpers are used on corners, as is this embodiment, the bumpers prevent the springs from forming acute edge, which can also help prevent discomfort or tissue damage. Bumpers 1093 can provide similar functionality to cushioning member described herein. It is thus contemplated that the devices herein can have cushioning elements where they are expected apply the most force to bodily structures, thus preventing discomfort and possible tissue damage.

Any of the components from any of the embodiments herein can be incorporated into any of the other embodiments or replaced with similar components from other embodiments unless it is specifically stated to the contrary.

What is claimed is:

1. A method of selectively occluding a rectum to inhibit stool passage in a female user, the method comprising:
   inserting an intravaginal device into the user's vagina, the device comprising an occluding portion;
   engaging vaginal anatomy to stably support the occluding portion proximal to the vagina's perineal body;
   extending the occluding portion against a recto-vaginal septum of the vagina proximal to the vagina's perineal body during the engaging step to at least partially occlude the user's rectum, the extending step comprising extending the occluding portion during the engaging step from a first state in which the intravaginal device has a first height to a second state in which the intravaginal device has a second height to at least partially occlude the user's rectum; and retracting the occluding portion during the engaging step to permit stool to pass through the rectum; the retracting step comprising retracting the occluding portion from the second state to the first state during the engaging step to permit stool to pass through the rectum, the ratio of the first height to the second height being less than about 0.5.

2. The method of claim 1 wherein the engaging step comprises engaging internal vaginal anatomy to stably support the occluding portion against a recto-vaginal septum of the vagina proximal to the perineal body.

3. The method of claim 1 wherein the engaging step comprises engaging internal vaginal anatomy proximal to the inferior pubic ramus to stably support the occluding portion against a recto-vaginal septum of the vagina.

4. The method of claim 1 wherein the engaging step comprises engaging a distal portion of the intravaginal device on an anterior side of the vagina adjacent the pubic symphysis to stably support the occluding portion against a recto-vaginal septum of the vagina.

5. The method of claim 1 wherein the extending step comprises inflating the occluding portion to a pressure of 40-150 mm Hg.

6. The method of claim 1 wherein the extending step comprises applying a pressure of 40-150 mm Hg to the recto-vaginal septum.

7. The method of claim 1 wherein the extending step comprises inflating the occluding portion with 10-60 cc of fluid.

8. The method of claim 1 wherein the engaging step comprises engaging internal vaginal anatomy to stably support the occluding portion proximal to the vagina's perineal body while maintaining slack in the vagina wall.

9. The method of claim 1 wherein the engaging step comprises distending lateral walls of the vagina proximate to the occluding portion less than in areas not proximate to the occluding portion.

10. The method of claim 1 wherein the extending step comprises actuating the occluding portion from outside the vagina and limiting force applied to the recto-vaginal septum by the occluding portion.

11. The method of claim 1 wherein the retracting step comprises actively retracting the occluding portion.

12. The method of claim 11 wherein the extending step comprises inflating the occluding portion and the retracting step comprises actively removing fluid from the occluding portion.

13. The method of claim 1 wherein the intravaginal device further comprises a stabilizing portion having a cushioning member that is more flexible than another part of the stabilizing portion, the engaging step comprising engaging vaginal tissue with the cushioning member.

14. The method of claim 1 wherein the extending step comprises extending a 20-60 mm wide surface of the occluding portion against the recto-vaginal septum.

15. The method of claim 1 wherein the engaging step comprises distributing device support forces evenly on an anterior wall of the user's vagina.

16. The method of claim 1 further comprising maintaining engagement with the vaginal anatomy to stably support the occluding portion proximal to the vagina's perineal body during the retracting step and, after the retracting step, extending the occluding portion against a recto-vaginal septum of the vagina proximal to the vagina's perineal body to at least partially occlude the user's rectum.

* * * * *